US006251639B1

(12) United States Patent
Kurn

(10) Patent No.: US 6,251,639 B1
(45) Date of Patent: Jun. 26, 2001

(54) METHODS AND COMPOSITIONS FOR LINEAR ISOTHERMAL AMPLIFICATION OF POLYNUCLEOTIDE SEQUENCES, USING A RNA-DNA COMPOSITE PRIMER

(75) Inventor: Nurith Kurn, Palo Alto, CA (US)

(73) Assignee: Nugen Technologies, Inc., San Carlos, CA (US)

( * ) Notice: Subject to any disclaimer, the term of this patent is extended or adjusted under 35 U.S.C. 154(b) by 0 days.

(21) Appl. No.: 09/660,877

(22) Filed: Sep. 13, 2000

Related U.S. Application Data
(60) Provisional application No. 60/175,780, filed on Jan. 12, 2000, and provisional application No. 60/153,604, filed on Sep. 13, 1999.

(51) Int. Cl.$^7$ .............................. C12Q 1/68; C12P 19/34; C07H 21/02; C07H 21/04; G01N 33/53

(52) U.S. Cl. ........................... 435/91.2; 435/6; 435/7.1; 435/91.1; 536/22.1; 536/23.1; 536/24.3; 536/24.31; 536/24.32; 536/24.33

(58) Field of Search ................................ 435/6, 7.1, 91.1, 435/91.2; 536/22.1, 23.1, 24.3, 24.31, 24.32, 24.33

(56) References Cited

U.S. PATENT DOCUMENTS

| | | |
|---|---|---|
| 4,582,788 | 4/1986 | Erlich . |
| 4,683,194 | 7/1987 | Saiki et al. . |
| 4,786,600 | 11/1988 | Kramer et al. . |
| 5,130,238 | 7/1992 | Malek et al. . |
| 5,169,766 | 12/1992 | Schuster et al. . |
| 5,194,370 | 3/1993 | Berninger et al. . |
| 5,399,491 | 3/1995 | Kacian et al. . |
| 5,427,911 | 6/1995 | Ruano . |
| 5,427,929 | 6/1995 | Richards et al. . |
| 5,437,990 | 8/1995 | Burg et al. . |
| 5,480,784 | 1/1996 | Kacian et al. . |
| 5,508,178 | 4/1996 | Rose et al. . |
| 5,554,516 | 9/1996 | Kacian et al. . |
| 5,554,517 | 9/1996 | Davey et al. . |
| 5,595,891 | 1/1997 | Rose et al. . |
| 5,648,211 | 7/1997 | Fraiser et al . |
| 5,654,142 | 8/1997 | Kievits et al. . |
| 5,665,545 * | 9/1997 | Malek et al. ............................. 435/6 |
| 5,665,845 | 9/1997 | Allman . |
| 5,679,512 | 10/1997 | Laney et al. . |
| 5,683,879 | 11/1997 | Laney et al. . |
| 5,710,028 | 1/1998 | Eyal et al. . |
| 5,744,308 | 4/1998 | Guillou-Bonnici et al. . |
| 5,744,312 | 4/1998 | Mamone et al. . |
| 5,766,849 | 6/1998 | McDonough et al. . |
| 5,824,517 | 10/1998 | Cleuziat et al. . |
| 5,824,518 | 10/1998 | Kacian et al. . |
| 5,846,710 | 12/1998 | Bajaj . |
| 5,871,697 | 2/1999 | Rothberg et al. . |
| 5,876,976 | 3/1999 | Richards et al. . |
| 5,882,867 | 3/1999 | Ullman et al. . |
| 5,888,779 | 3/1999 | Kacian et al. . |
| 5,888,819 | 3/1999 | Goelet et al. . |
| 5,962,272 | 10/1999 | Chenchik et al. . |
| 6,004,744 | 12/1999 | Goelet et al. . |
| 6,004,745 | 12/1999 | Arnold, Jr. et al. . |
| 6,013,431 | 1/2000 | Soderlund et al. . |
| 6,027,889 | 2/2000 | Barany et al. . |
| 6,027,923 | 2/2000 | Wallace . |
| 6,030,774 | 2/2000 | Laney et al. . |
| 6,037,152 | 3/2000 | Richards et al. . |
| 6,107,032 | 8/2000 | Kilger et al. . |

FOREIGN PATENT DOCUMENTS

| | | |
|---|---|---|
| 0 237 362 A1 | 9/1887 | (EP) . |
| 0 050 424 Al | 4/1982 | (EP) . |
| 0 084 796 A2 | 8/1983 | (EP) . |
| 0 201 184 A2 | 12/1986 | (EP) . |
| 0 258 017 A2 | 3/1988 | (EP) . |
| 0 320 308 B1 | 6/1989 | (EP) . |
| 0 505 012 B1 | 9/1992 | (EP) . |
| 07023799 A2 * | 1/1995 | (JP) . |
| WO 88/02746 A1 | 4/1988 | (WO) . |
| WO 88/10315 A1 | 12/1988 | (WO) . |
| WO 89/01050 A1 | 2/1989 | (WO) . |
| WO 98/28443 | 7/1998 | (WO) . |
| WO 99/18241 A1 | 4/1999 | (WO) . |
| WO 99/42618 A1 | 8/1999 | (WO) . |
| WO 00/28082 A1 | 5/2000 | (WO) . |

OTHER PUBLICATIONS

Ausubel, F.M. et al. eds. (1995). *Current Protocols in Molecular Biology*. John Wiley & Sons, Inc., pp. iii–xii (Table of Contents).

Flanagan, W. M. et al., (Mar., 1999). "A Cytosine Analog That Confers Enhanced Potency to Antisense Oligonucleotides," *Proc. Natl. Acad. Sci. USA* 96(7):3513–3518.

Freshney, R.I., ed (1987). *Animal Cell Culture*. IRL Press: Oxford, pp. vii–xii (Table of Contents).

(List continued on next page.)

Primary Examiner—Kenneth R. Horlick
Assistant Examiner—Jeffrey Siew
(74) Attorney, Agent, or Firm—Morrison & Foerster LLP

(57) ABSTRACT

The present invention provides novel isothermal, single primer linear nucleic acid amplification methods. Methods for amplifying complementary DNA using a composite primer, primer extension, strand displacement, and optionally a termination sequence, are provided. Methods for amplifying sense RNA using a composite primer, primer extension, strand displacement, optionally template switching, a propromoter oligonucleotide and transcription are also provided. The invention further provides compositions and kits for practicing said methods, as well as methods which use the amplification products.

116 Claims, 18 Drawing Sheets-

OTHER PUBLICATIONS

Gait, M.J., ed. (1984), *Oligonucleotide Synthesis: A Practical Approach*. IRL Press: Oxford, pp. vii–xii (Table of Contents).

Gasparini et al. (1996). "Scanning the first part of the neurofibromatosis type 1 gene by RNA–SSCP: identification of three novel mutations and of two new polymorphisms," *Hum. Genet.* 97:492–495.

Guatelli et al. (Mar., 1990). "Isothermal, In Vitro Amplification of Nucleic Acids by a Multienzyme Reaction Modeled After Retroviral Replication," *Proc. Natl. Acad. Sci. USA* 87:1874–1878.

Kumar et al. (1998). "The First Analogues of LNA (Locked Nucleic Acids): Phosphorothioate–LNA and 2'–Thio–LNA," *Bioorg. Med. Chem. Lett.* 8:2219–2222.

Kwoh et al. (1989). "Transcription–Based Amplification System and Detection of Amplified Human Immunodeficiency Virus Type 1 with a Bead–Based Sandwich Hybridization Format," *Proc. Natl. Acad. Sci. USA* 86:1173.

Lishanski, A. et al. (2000). "Branch Migration Inhibition in PCR–Amplified DNA: Homogeneous Mutation Detection," *Nucl. Acids Res.* 28(9):E42.

Mullis et al. (1986). "Specific Enzymatic Amplification of DNA In Vitro: the Polymerase Chain Reaction," *Cold Spring Harbor Symp. Quant. Bio.* 51:263–273.

Mullis, K.B. et al., eds. (1994). *PCR: The Polymerase Chain Reaction*. Birkhäuser: Boston, pp. xv–xvii (Table of Contents).

Orita M., et al. (1989). "Detection of Polymorphisms of Human DNA by Gell Electrophoresis as Single–Strand Conformation Polymorphisms," *Proc. Natl. Acad. Sci. USA* 86(8):2766–2770.

Patel et al. (Apr., 1996). "Formation of Chimeric DNA Primer Extension Products by Template Switching Onto an Annealed Downstream Oligonucleotide," *Proc. Natl. Acad. Sci. USA* 93:2969–2974.

Saiki, et al. (1988). "Primer–Directed Enzymatic Amplification of DNA with a Thermostable DNA Polymerase," *Science* 239:487.

Sambrook, J. et al., eds. (1989). *Molecular Cloning: A Laboratory Manual*. 2nd Edition, Cold Spring Harbor Laboratory Press, pp. xi–xxxviii (Table of Contents).

Sarkar et al. (1992). "Screening for Mutations by RNA Single–Strand Conformation Polymorphism (rSSCP): Comparison with DNA–SSCP," *Nucl. Acids Res.* 20(4):871–878.

Sasaki, N. et al. (Mar., 1998). "Transcriptional Sequencing: A Method for DNA Sequencing Using RNA Polyhmerase" *Proc. Natl. Acad. Sci. USA* 95:3455–3460.

Scaringe, S.A. (2000). "Advanced 5'3silyl–2'–orthoester approach to RNA oligonucleotide synthesis," *Meth. Enzymol.* 317:3–18.

Suzuki, Y. et al. (1990). "Detection of Ras Gene Mutations in Human Lung Cancers by Single–Strand Conformation Polymorphism Analysis of Polymerase Chain Reaction Products," *Oncogene* 5(7):1037–1043.

Wahlestedt et al. (May 9, 2000). "Potent and Nontoxic Antisense Oligonucleotides Containing Locked Nucleic Acids," *Proc. Natl. Acad. Sci. USA* 97(10):5633–5638.

Walker et al. (Jan., 1992). "Isothermal In Vitro Amplification of DNA by a Restriction Enzyme/DNA Polymerase System," *Proc. Natl. Acad. Sci. USA* 89:392–396.

Wu et al. (1989). "The Ligation Amplification Reaction (LAR)—Amplification of Specific DNA Sequences Using Sequential Rounds of Template–Dependent Ligation," *Genomics* 4:560–569.

* cited by examiner

X denotes a mutation on the target DNA at a site complementary to the 5' RNA portion of the primer.
As shown, amplification of the target NA is blocked when a mutation is present.

METHODS AND COMPOSITIONS FOR LINEAR ISOTHERMAL AMPLIFICATION OF POLYNUCLEOTIDE SEQUENCES, USING A RNA-DNA COMPOSITE PRIMER

CROSS-REFERENCE TO RELATED APPLICATIONS

This application claims the priority benefit of the provisional patent applications U.S. Ser. No. 60/153,604, filed Sep. 13, 1999, and U.S. Ser. No. 60/175,780, filed Jan. 12, 2000, both of which are incorporated by reference in their entirety.

TECHNICAL FIELD

The invention relates to the field of polynucleotide amplification. More particularly, the invention provides methods, compositions and kits for amplifying (i.e., making multiple copies) target polynucleotide sequences which employ a single RNA/DNA composite primer, with the amplification optionally involving transcription.

BACKGROUND

The developments of methods for nucleic acid amplification and detection of amplification products have advanced the detection, identification, quantification and sequence analyses of nucleic acid sequences in recent years.

Nucleic acid analysis is useful for detection and identification of pathogens, detection of gene alteration leading to defined phenotypes, diagnosis of genetic diseases or the susceptibility to a disease, assessment of gene expression in development, disease and in response to defined stimuli, as well as the various genome projects. Other applications of nucleic acid amplification method are the detection of rare cells, detection of pathogens, and the detection of altered gene expression in malignancy, and the like. Nucleic acid amplification is potentially useful for both qualitative analysis, such as the detection of the presence of defined nucleic acid sequences, and quantification of defined gene sequences. The latter is useful for assessment of and amount of pathogenic sequences as well as the determination of gene multiplication or deletion, as often found in cell transformation from normal to malignant cell type.

The detection of sequence alterations in a nucleic acid sequence is important for the detection of mutant genotypes, as relevant for genetic analysis, the detection of mutations leading to drug resistance, pharmacogenomics, etc. Various methods for the detection of specific mutations include allele specific primer extension, allele specific probe ligation, and differential probe hybridization. See, for example, U.S. Pat. Nos. 5,888,819; 6,004,744; 5,882,867; 5,710,028; 6,027,889; 6,004,745; and WO US88/02746. Methods for the detection of the presence of sequence alterations in a define nucleic acid sequence, without the specific knowledge of the alteration, were also described. Some of these methods are based on the detection of mismatches formed by hybridization of a test amplification product to a reference amplification product. The presence of mismatches in such heteroduplexes can be detected by the use of mismatch specific binding proteins, or by chemical or enzymatic cleavage of the mismatch. A method for detection of sequence alteration which is based on the inhibition of branch migration in cruciform four stranded DNA structures was recently described. See, for example, Lishanski, A. et al. *Nucleic Acids Res* 28(9):E42 (2000). Other methods are based on the detection of specific conformations of single stranded amplification products. The secondary structure of a single stranded DNA or RNA is dependent on the specific sequence. Sequence alterations in a test nucleic acid target relative to a reference sequence leads to altered conformation. Altered conformation of a single stranded amplification product can be detected by a change in the electrophoretic mobility of the test amplification product as compared to that of a reference amplification product. Single stranded conformation polymorphism, SSCP, is widely used for the detection of sequence alterations. See, for example, Orita M., et al. *Proc Natl Acad Sci USA* 86(8):2766–70 (1989); Suzuki, Y. et al. *Oncogene* 5(7):1037–43 (1990); and U.S. Pat. No. 5,871,697. This method is also used in microbial identification that is based on the defined changes in a specific nucleic acid sequence in different strains or species. Mutation detection using the SSCP methods mostly employs DNA amplification products, however, RNA-SSCP methods have also been described. Sequence dependent conformation of a single stranded RNA is well-documented and was shown to lead to a defined electrophoretic mobility pattern. See, for example, Sarkar et al. *Nucleic Acid Research* 20(4):871–878 (1992) and Gasparini et al. *Hum. Genet.* 97:492–495 (1996).

Although detection of the presence of a defined nucleic acid sequence, and its sequence analysis, can be carried out by probe hybridization, the method generally lacks sensitivity when low amounts of the nucleic acid sequence is present in the test sample, such as a few molecules. One solution to this obstacle was the development of methods for generation of multiple copies of the defined nucleic acid sequence, which are suitable for further analysis. The methods for generation of multiple copies of a specific nucleic acid sequence are generally defined as target amplification methods. Other methods for increasing the sensitivity of detection of hybridization analysis are based on the generation of multiple products from the hybridized probe, or probes, for example cleavage of the hybridized probe to form multiple products or the ligation of adjacent probes to form a unique hybridization dependent product. Similarly, increased sensitivity of hybridization reaction was achieved by methods for amplification of signals generated by the hybridization event, such as the method based on hybridization of branched DNA probes.

There are many variations of nucleic acid amplification, for example, exponential amplification, linked linear amplification, ligation-based amplification, and transcription-based amplification. An example of exponential nucleic acid amplification method is polymerase chain reaction (PCR) which has been disclosed in numerous publications. See, for example, Mullis et al. *Cold Spring Harbor Symp. Quant. Biol.* 51:263–273 (1986); Mullis K. EP 201,184; Mullis et al. U.S. Pat. No. 4,582,788; Erlich et al. EP 50,424, EP 84,796, EP 258,017, EP 237,362; and Saiki R. et al. U.S. Pat. No. 4,683,194. Linked linear amplification is disclosed by Wallace et al. in U.S. Pat. No. 6,027,923. Examples of ligation-based amplification are the ligation amplification reaction (LAR), disclosed by Wu et al. in *Genomics* 4:560 (1989) and the ligase chain reaction, disclosed in EP Application No. 0320308B1. Various methods of transcription-based amplification are disclosed in U.S. Pat. Nos. 5,766,849 and 5,654,142; and also by Kwoh et al. *Proc. Natl. Acad. Sci. U.S.A.* 86:1173 (1989) and Ginergeras et al. WO 88/10315.

The most commonly used target amplification method is the polymerase chain reaction, PCR, which is based on multiple cycles of denaturation, hybridization of two oligonucleotide primers, each to opposite strand of the target strands, and primer extension by a nucleotide polymerase to produce multiple double stranded copies of the target sequence. Many variations of PCR have been described, and the method is being used for amplification of DNA or RNA nucleic acid sequences, sequencing, mutation analysis and others. Thermocycling-based methods that employ a single primer, have also been described. See, for example, U.S. Pat. Nos. 5,508,178; 5,595,891; 5,683,879; 5,130,238; and 5,679,512. The primer can be a DNA/RNA chimeric primer, as disclosed in U.S. Pat. No. 5,744,308. Other methods that are dependent on thermal cycling are the ligase chain reaction (LCR) and the related repair chain reaction (RCR).

Target nucleic acid amplification may be carried out through multiple cycles of incubations at various temperatures, i.e. thermal cycling, or at one temperature (an isothermal process). The discovery of thermostable nucleic acid modifying enzymes has contributed to the fast advances in nucleic acid amplification technology. See Saiki, et al. *Science* 239:487 (1988). Thermostable nucleic acid modifying enzymes, such as DNA and RNA polymerases, ligases, nucleases and the like, are used in both methods dependent on thermal cycling and isothermal amplification methods. Isothermal methods such as strand displacement amplification (SDA) is disclosed by Fraiser et al. in U.S. Pat. No. 5,648,211; Cleuziat et al. in U.S. Pat. No. 5,824,517; and Walker et al. *Proc. Natl. Acad. Sci. U.S.A.* 89:392–396 (1992). Other isothermal target amplification methods are the transcription-based amplification methods, in which an RNA polymerase promoter sequence is incorporated into primer extension products at an early stage of the amplification (WO 89/01050), and further target sequence, or target complementary sequence, is amplified by transcription steps and digestion of an RNA strand in a DNA/RNA hybrid intermediate product. See, for example, U.S. Pat. Nos. 5,169,766 and 4,786,600. These methods include transcription mediated amplification (TMA), self-sustained sequence replication (3SR), Nucleic Acid Sequence Based Amplification (NASBA), and variations there of. See, for example, Guatelli et al. *Proc. Natl. Acad. Sci. U.S.A.* 87:1874–1878 (1990); U.S. Pat. No. 5,766,849 (TMA); and U.S. Pat. No. 5,654,142 (NASBA). Other amplifications methods use template switching oligonucleotides (TSOs) and blocking oligonucleotides. For example, the template switch amplification in which chimeric DNA primer are utilitized is disclosed in U.S. Pat. No. 5,679,512 and by Patel et al. *Proc. Natl. Acad. Sci. U.S.A.* 93:2969–2974 (1996) and blocking oligonucleotides are disclosed by Laney et al. in U.S. Pat. No. 5,679,512.

The isothermal target amplification methods do not require a thermocycler, and are thus easier to adapt to common instrumentation platform. However the previously described isothermal target amplification methods have several drawbacks. Amplification according to the SDA methods requires the presence of sites for defined restriction enzymes, which limits its applicability. The transcription base amplification methods, such as the NASBA and TMA, on the other hand, are limited by the need for incorporation of the polymerase promoter sequence into the amplification product by a primer, a process prone to result in non-specific amplification. Moreover, the mechanism of amplification of a DNA target by these transcription based amplification methods is not well-established.

Another drawback of the current amplification methods is the potential contamination test samples by amplification products of prior amplification reactions, resulting in non-target specific amplification in samples. This drawback is a well-known problem, which is the result of the power of target amplification technology, and the formation of amplification products, which are substrates for amplification. Various means for decontamination of test samples either at the end of the amplification reaction, or prior to the initiation of target amplification have been described. In additions, method for containment of the test solution by physical means, were also described. All of these solutions are cumbersome and add to the complexity of nucleic acid testing in the common laboratory setting.

Furthermore, amplification methods that use thermocycling process have an added disadvantage of long lag times which are required for the thermocycling block to reach the "target" temperature for each cycle. Consequently, amplification reactions performed using thermocycling processes require a significant amount of time to reach completion.

Therefore, there is a need for improved nucleic acid amplification methods that overcome these drawbacks. The invention provided herein fulfills this need and provides additional benefits.

All references cited herein, including patent applications and publications, are incorporated by reference in their entirety.

DISCLOSURE OF THE INVENTION

The invention provides methods and compositions for polynucleotide amplification, as well as applications of the amplification methods.

Accordingly, in one aspect, the invention provides methods for amplifying a polynucleotide sequence complementary to a target polynucleotide sequence comprising: (a) hybridizing a single stranded DNA template comprising the target sequence with a composite primer, said composite primer comprising an RNA portion and a 3' DNA portion; (b) optionally hybridizing a polynucleotide comprising a termination polynucleotide sequence to a region of the template which is 5' with respect hybridization of the composite primer to the template; (c) extending the composite primer with DNA polymerase; (d) cleaving the RNA portion of the annealed composite primer with an enzyme that cleaves RNA from an RNA/DNA hybrid such that another composite primer can hybridize to the template and repeat primer extension by strand displacement, whereby multiple copies of the complementary sequence of the target sequence are produced.

In another aspect, the invention provides methods for amplifying a target polynucleotide sequence comprising: (a) hybridizing a single stranded DNA template comprising the target sequence with a composite primer, said composite primer comprising an RNA portion and a 3' DNA portion; (b) hybridizing a polynucleotide comprising a termination polynucleotide sequence to a region of the template which is 5' with respect hybridization of the composite primer to the template; (c) extending the composite primer with DNA polymerase; (d) cleaving the RNA portion of the annealed composite primer with an enzyme that cleaves RNA from an RNA/DNA hybrid such that another composite primer can hybridize to the template and repeat primer extension by strand displacement to produce displaced primer extension product; (e) hybridizing a polynucleotide comprising a pro-promoter and a region which hybridizes to the displaced primer extension product under conditions which allow transcription to occur by RNA polymerase, such that RNA transcripts are produced comprising sequences complementary to the displaced primer extension products, whereby multiple copies of the target sequence are produced.

Various embodiments of the composite primer used in the methods of the invention are described herein. For example, in some embodiments, the RNA portion of the composite primer is 5' with respect to the 3' DNA portion. In still other embodiments, the 5' RNA portion is adjacent to the 3' DNA portion. For the methods described herein, one or more composite primers can be used.

Various exemplary embodiments of polynucleotides comprising a termination sequence are also described herein. In some embodiments, the polynucleotide comprising a termination sequence is a template switch oliognucleotide (TSO), which may (but not necessarily) contain one or more modifications to enhance binding to template. Accordingly, in some embodiments, the TSO comprises a modification in the region which hybridizes to the template, wherein, under a given set of conditions, the TSO binds more tightly to the region as compared to a TSO without the modification. Examples of suitable modifications are provided herein. In some embodiments, the polynucleotide comprising a termination sequence is a blocking sequence, which, like the TSO, may contain one or more modifications to enhance binding to template. Accordingly, in some embodiments, the blocker sequence comprises a modification in the region which hybridizes to the template, wherein, under a given set of conditions, the blocker binds more tightly to the region as compared to a blocker without the modification. Examples of suitable modifications are provided herein.

The enzymes which may be used in the methods and compositions are described herein. For example, the enzyme that cleaves RNA may be an RNaseH.

In some aspects, a TSO provides propromoter function and also comprises a region (which may or may not be adjacent to the promoter) which hybridizes to the displaced primer extension product. In other embodiments, the polynucleotide comprising the propromoter comprises a region at the 3' end which hybridizes to the displaced primer extension product, whereby DNA polymerase extension of displaced extension product produces a double stranded promoter from which transcription occurs. In some embodiments, the polynucleotide comprising the propromoter is a PTO.

The methods are applicable to amplifying any DNA target, including, for example, genomic DNA and cDNA. One or more steps may be combined and/or performed sequentially (often in any order, as long as the requisite product(s) are able to be formed).

The invention also provides methods which employ (usually, analyze) the products of the amplification methods of the invention, such as sequencing and detection of sequence alteration(s).

Accordingly, in one aspect, the invention provides methods of sequencing a target nucleotide sequence comprising: (a) hybridizing a single stranded DNA template comprising the target sequence with a composite primer, said composite primer comprising an RNA portion and a 3' DNA portion; (b) optionally hybridizing a polynucleotide comprising a termination polynucleotide sequence to a region of the template which is 5' with respect hybridization of the composite primer to the template; (c) extending the composite primer with DNA polymerase and a mixture of dNTPs and DNTP analogs (which may be labelled or unlabelled), such that primer extension is terminated upon incorporation of a dNTP analog which may be labelled or unlabelled; (d) cleaving the RNA portion of the annealed composite primer with an enzyme that cleaves RNA from an RNA/DNA hybrid such that another composite primer can hybridize to the template and repeat primer extension by strand displacement, whereby multiple copies of the complementary sequence of the target sequence are produced of varying lengths; (e) analyzing the product of steps (a) through (d) to determine sequence.

In another aspect, the invention provides methods for sequencing a target nucleotide sequence comprising (a) hybridizing a single stranded DNA template comprising the target sequence with a composite primer, said composite primer comprising an RNA portion and a 3' DNA portion; (b) hybridizing the template with a polynucleotide comprising a termination polynucleotide sequence to a region of the template which is 5' with respect to hybridization of the composite primer to the template; (c) extending the composite primer with DNA polymerase; (d) cleaving the RNA portion of the annealed composite primer with an enzyme that cleaves RNA from an RNA/DNA hybrid such that another composite primer can hybridize to the template and repeat primer extension by strand displacement to produce displaced primer extension product; (e) hybridizing a polynucleotide comprising a propromoter at the 5' end and a region which hybridizes to the displaced primer extension product under conditions such that transcription occurs from the extension product by RNA polymerase, using a mixture of rNTPs and rNTP analogs (which may be labelled or unlabelled), such that RNA transcripts are produced comprising sequences complementary to the displaced primer extension products, and such that transcription is terminated upon incorporation of an rNTP analog which may be labelled or unlabelled, whereby multiple copies of the target sequence are produced of varying lengths; (f) analyzing the product of steps (a) through (e) to determine sequence.

In some aspects, the invention provides methods of characterizing, or analyzing, sequence of a target. Some aspects are based on the RNA portion of the composite primer and accordingly the results reflect information regarding the corresponding region of the target which, if complementary or of sufficient complementarity, hybridizes to the RNA portion of the composite primer. The amount of product as compared to amount of product from performing the same amplification reaction on a reference target sequence indicates the presence or absence of a sequence, which may in turn indicate presence or absence of wildtype, mutant, or allelic variants. Various sequence detection embodiments are described herein. Thus, for example, the invention provides methods of detecting a mutation in a region of a target polynucleotide sequence, comprising conducting an amplification method described herein, wherein the region of the target polynucleotide sequence corresponds to the RNA portion of the composite primer, and wherein a mutation in the target polynucleotide results in detectably fewer amplification products as compared to the amount of amplification products produced from a reference template comprising region corresponding to the RNA portion of the composite primer which does not comprise a mutation. In these embodiments, amplification by strand displacement is decreased as compared to production from a reference template which comprises a region corresponding to the RNA portion of the composite primer which does not contain the mutation (as compared to the RNA portion of the composite primer).

Thus, the invention provides methods of characterizing a sequence of interest in a target polynucleotide, said methods comprising conducting the amplification methods of the invention wherein the sequence of an RNA portion of the composite primer is known, and wherein (a) production of detectably fewer amplification products from the template as compared to the amount of amplification products from a reference template which comprises a region complementary to the RNA portion of the composite primer indicates that the target polynucleotide does not comprise a sequence complementary to the RNA portion of the composite primer and is a sequence variant with respect to the sequence complementary to the RNA portion of the composite primer; or (b) production of detectably more amplification products from the template as compared to the amount of amplification products from a reference template which does not comprise a region which is complementary to the RNA portion of the composite primer indicates that the target polynucleotide comprises a sequence complementary to the RNA portion of the composite primer and is not a sequence variant with respect to the sequence complementary to the RNA portion of the composite primer. In one embodiment, the sequence of an RNA portion of the composite primer comprises a wild type sequence, and the sequence of interest is characterized in determining the presence or absence of the wild type sequence. In another embodiment, the sequence of an RNA portion of the composite primer comprises a mutant sequence, and the sequence of interest is characterized in determining the presence or absence of the mutant sequence. In yet another embodiment, the sequence of an RNA portion of the composite primer comprises an allelic sequence, and the sequence of interest in characterized in determining the presence or absence of the allelic sequence.

In other aspects, the invention provides methods of detecting a mutation (or, in some aspects, characterizing a sequence) in a target polynucleotide, comprising (a) conducting an amplification method described herein; and (b) analyzing the amplified products of the method for single stranded conformation, wherein a difference in conformation as compared to a reference single stranded polynucleotide indicates a mutation in the target polynucleotide. In other embodiments, the invention provides methods of detecting a mutation (or, in some aspects, characterizing a sequence) in a target polynucleotide comprising analyzing amplified products of any of the methods described herein for single stranded conformation, wherein a difference in conformation as compared to a reference single stranded polynucleotide indicates a mutation in the target polynucleotide (or, in some aspects, characterizes the target sequence).

In other aspects, the invention provides methods of producing a microarray, comprising (a) conducting an amplification method described herein; and (b) attaching the amplified products onto a solid substrate to make a microarray of the amplified products. In other embodiments, microarrays are produced by attaching amplified products by any of the methods describd herein onto a solid substrate to make a microarray of amplified products.

Any of these applications can use any of the amplification methods (including various components and various embodiments of any of the components) as described herein. For example, the composite primer used may have a 5' RNA portion, which may be adjacent to the 3' DNA portion.

The invention also provides compositions, kits, complexes, reaction mixtures and systems comprising various components (and various combinations of the components) used in the amplification methods described herein. In one aspect, for example, the invention provides compositions comprising a composite primer, said composite primer comprising a 3' DNA portion and a 5' RNA portion. In some embodiments, the 5' RNA portion is adjacent to the 3' DNA portion. In still other embodiments, the 5' RNA portion is about 5 to about 20 nucleotides and the 3' DNA portion is about 5 to about 15 nucleotides. In another aspect, the invention provides compositions comprising a TSO, wherein the TSO comprises a modification in the region which hybridizes to the template, wherein, under a given set of conditions, the TSO binds more tightly to the region as compared to a TSO without the modification.

In some embodiments, the compositions of the invention comprise any composite primer described herein and a TSO. In still other embodiments, the invention provides compositions comprising any of the composite primers described herein and any blocking sequences described herein, including those containing modifications which enhance binding to template. In other embodiments, the invention provides compositions comprising any of the composite primers described herein and a PTO.

In another aspect, the invention provides compositions comprising any of the complexes (which are generally considered as intermediates with respect to the final amplification products) described herein (see also the figures for schematic depictions of these various complexes). For example, the invention provides compositions comprising a complex of (a) a template strand; and (b) a composite primer, said composite primer comprising a 3' DNA portion and an RNA portion. The RNA portion may be 5' as well as adjacent to the DNA portion. In some embodiments, the complex further comprises a polynucleotide comprising a termination sequence (which may be, for example, a TSO or a blocking sequence). In some embodiments, the complex further comprises a PTO.

In another aspect, the invention provides reaction mixtures (or compositions comprising reaction mixtures) which contain various combinations of components described herein. For example, the invention provides reaction mixtures comprising (a) a polynucleotide template; (b) a composite primer comprising a 3' DNA portion and an RNA portion; and (c) DNA polymerase. As described herein, any of the composite primers may be in the reaction mixture (or a plurality of composite primers), including a composite primer comprises a 5' RNA portion which is adjacent to the 3' DNA portion. The reaction mixture could also further comprise an enzyme which cleaves RNA from an RNA/DNA hybrid, such as RNase H. A reaction mixture of the invention can also comprise any of the polynucleotides comprising termination sequences described herein, as well as a polynucleotide comprising a propromoter and a region which hybridizes to displaced primer extension product, and an RNA polymerase. A reaction mixture of the invention can also comprise a PTO.

In another aspect, the invention provides kits for conducting the methods described herein. These kits, in suitable packaging and generally (but not necessarily) containing suitable instructions, contain one or more components used in the amplification methods. For example, the invention provides kits that comprise a composite primer comprising a 3' DNA portion and an RNA portion (which may be 5' and may further be adjacent to the 3' DNA portion). The composite primer in the kits can be any described herein. The kits can contain further components, such as any of (a) a polynucleotide comprising a termination polynucleotide sequence; (b) a polynucleotide comprising a propromoter; (c) any of the enzymes described herein, such as an enzyme which cleaves RNA from an RNA/DNA hybrid (for example, RNaseH); and (d) a polynucleotide comprising a propromoter and a region which hybridizes to displaced primer extension product.

In another aspect, the invention provides systems for effecting the amplification methods described herein. For example, the invention provides systems for amplifying a target polynucleotide sequence or its complement, comprising (a) a composite primer comprising a 3' DNA portion and an RNA portion; (b) DNA polymerase; and (c) an enzyme which cleaves RNA from an RNA/DNA hybrid (such as RNaseH). The composite primer may be any (one or more) described herein, including a composite primer which comprises a 5' RNA portion which is adjacent to the 3' DNA portion.

MODES FOR CARRYING OUT THE INVENTION

Figure 1A:
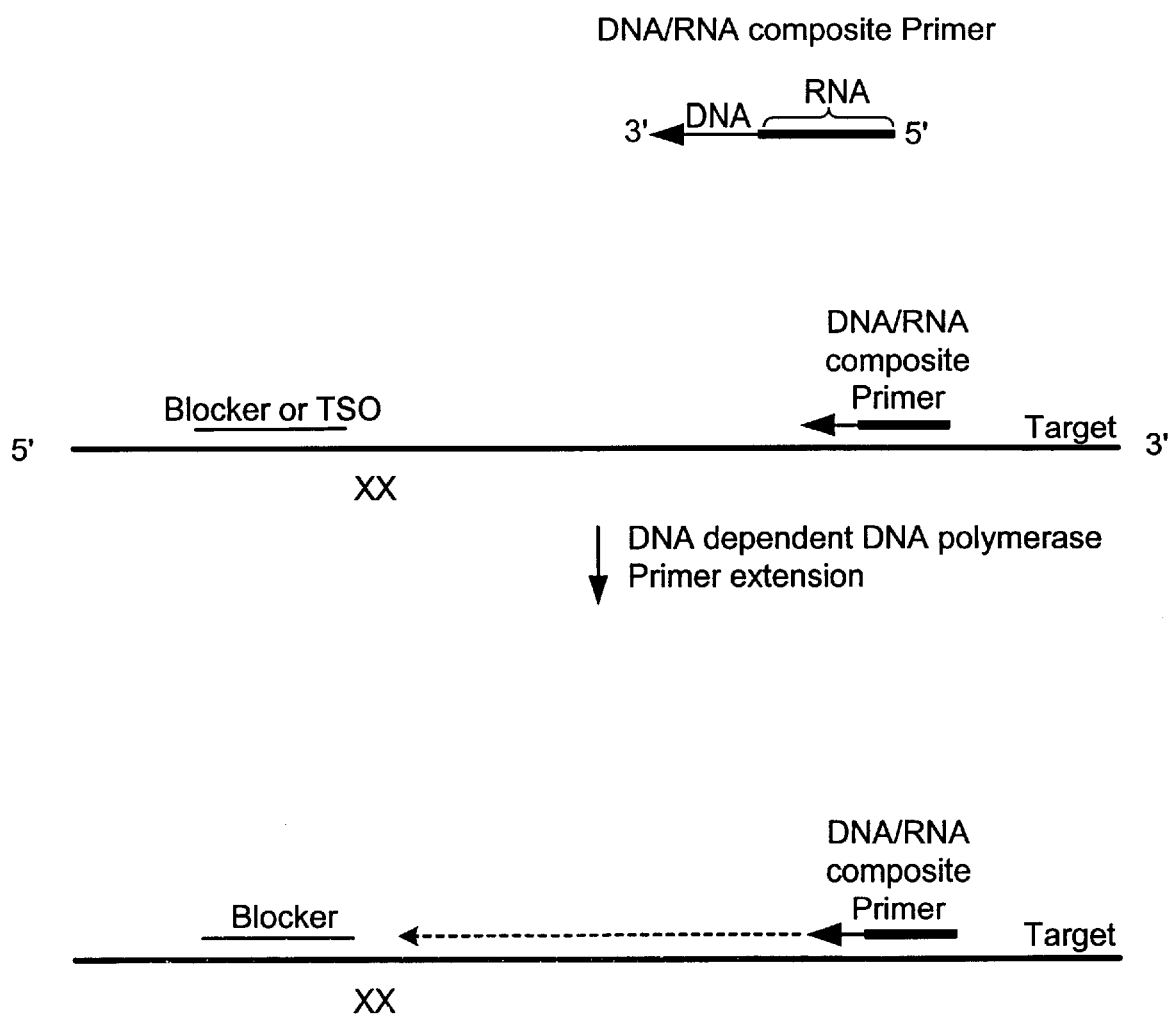
FIGS. 1A–C is a diagrammatic representation of a single composite primer isothermal linear amplification process.

The invention provides methods, compositions and kits for amplifying polynucleotide sequences. The methods generally comprise using an RNA/DNA composite primer, optionally a termination sequence, and, in embodiments in which transcription is used, a propromoter oliognucleotide sequence.

As a general summary, the amplification methods work as follows: a composite RNA/DNA primer forms the basis for replication of target sequence. In some embodiments, a termination sequence provides the basis for an endpoint for the replication by either diverting or blocking further replication along the target strand. As described below, in some embodiments, the polynucleotide comprising a termination sequence is a template switch oligonucleotide (TSO), which contains sequences that are not of sufficient complementarity to hybridize to the template strand (in addition to sequences which are of sufficient complementary to hybridize); in other embodiments, the termination sequence comprises primarily sequences that are of sufficient complementarity to hybridize to the template strand. DNA polymerase effects copying of the target sequence from the primer. An enzyme which cleaves RNA from an RNA/DNA hybrid (such as RNaseH) cleaves (removes) RNA sequence from the hybrid, leaving sequence on the template strand available for binding by another composite primer. Another strand is produced by DNA polymerase, which displaces the previously replicated strand, resulting in displaced extension product. Optionally, a polynucleotide comprising a propromoter and a region which hybridizes to the displaced primer extension product (which can be, for example, a template switch oligonucleotide or propromoter template oligonucleotide), which contains sequences of sufficient complementarity to hybridize to the 3' end of the displacement extension product, binds to the displaced primer extension product. The promoter drives transcription (via DNA-dependent RNA polymerase) to produce sense RNA products.

Accordingly, the invention provides methods of producing at least one copy of a target polynucleotide sequence (generally, methods of amplifying target polynucleotide sequence) comprising combining and reacting the following: (a) a single-stranded target polynucleotide comprising a target sequence; (b) a composite primer comprising an RNA portion and a 3' DNA portion; (c) a DNA polymerase; (d) deoxyribonucleoside triphosphates or suitable analogs; (e) an enyzme, such as RNaseH, which cleaves RNA from an RNA/DNA duplex; and (f) generally, but optionally, a polynucleotide comprising a termination sequence, such as any of those described herein, which comprises a portion (or region) which hybridizes to the template polynucleotide. A termination sequence is used if transcription-based amplification (see below) is also used. The combination is subjected to suitable conditions such that (a) the composite primer (and, optionally, a polynucleotide comprising a termination sequence) hybridizes to the template; (b) primer extension occurs from the composite primer, to form a duplex; (c) RNaseH cleaves RNA of the composite primer from the RNA/DNA duplex; (d) another composite primer hybridizes to the template, and another round of primer extension (mediated by DNA polymerase) occurs, displacing the strand already copied from the template.

Optionally, the following is also included in the amplification reaction (either at the same time as those components listed above or added separately): (e) a polynucleotide comprising a propromoter sequence (which can be in any of a number of forms, as described herein) and a region which hybridizes to the displaced primer extension product; (f) ribonucleoside triphosphates or suitable analogs; and (g) RNA polymerase, under conditions such that transcription of the displaced strand can occur. Details regarding the various components of the methods of the present invention are provided below.

In some embodiments, the invention provides methods of sequencing nucleic acids (DNA or RNA). For the sequencing methods, the appropriate dNTPs (or, when embodiments which rely on transcription-based amplifications are used, appropriate rNTPs), which may be labelled or unlabelled, are used. Accordingly, the invention provides methods of sequencing a target nucleotide sequence comprising the methods described above, wherein dNTPs and dNTP analogs which are primer elongation terminators, which may be labelled or unlabelled, and/or rNTPs and rNTP analogs, which are primer elongation terminators, which may be labelled or unlabelled, are used, and the amplification product is analyzed for sequence information, as described below.

In other embodiments, the invention provides methods of detecting nucleic acid sequence mutations and/or characterizing target sequence(s). In one embodiment, the presence or absence of a mutation in a target polynucleotide is detected based on the ability to amplify the target polynucleotide using a composite primer whose RNA portion either contains or lacks the mutated sequence using the methods of the invention. In another embodiment, the amplified products are used for detection of mutations by hybridization with specific probes. In yet another embodiment, the amplified products are used to detect and/or identify single strand conformation polymorphisms in a target polynucleotide.

In yet other embodiments, the invention provides methods for generating microarrays of nucleic acids (DNA or RNA) using the amplified products of the linear or enhanced linear nucleic acid amplification methods of the present invention.

Other methods which use the amplified products described herein are provided below.

Advantages of the Amplification Methods of the Invention

The amplification methods of the invention provide several significant advantages over other methods of nucleic acid amplification. The formation of primed template, primer extension and displacement of the previously generated extension product is dependent on the cleavage of the RNA portion of the hybridized primer by a ribonuclease activity. Thus, the primer extension product is lacking the 5'-most portion of the primer. Consequently, the RNA transcription product generated from the complex of the extension product and the template switch oligonucleotide, or the promoter template oligonucleotide, does not contain at its 3' end the sequence complementary to this portion of the primer. Thus, the amplification products are not capable of hybridizing to the primer for productive amplification, making the amplification methods of the invention resistant to non-specific amplification due to contamination with products generated by prior amplifications reactions. This feature clearly distinguishes it from other known target amplification methods, such as PCR, NASBA and the like, and renders the methods of the invention suitable for open tube platforms commonly used in clinical laboratories, high throughput testing sites, and the like.

The unique requirement of cleavage of the RNA portion of the composite primer in the hybridized and extended form, by a ribonuclease such as RNase H, for further progression of the amplification of the target nucleic acid sequence, results in the exclusive amplification of DNA target. Thus, it is possible to use the methods of the invention for amplification of genomic DNA targets in the presence of excess mRNA. This feature is useful for accurate quantification of gene dosage. When the test target nucleic acid sequence is RNA, the target is first transcribed to produce cDNA which can be amplified using the methods of the invention.

The methods of the invention also provide for amplification of target nucleic acids with high accuracy with respect to the template. Each amplification product is a direct copy of the target sequence in the input template DNA (in the linear amplification methods), or the input template DNA and the primer extension products of the input template DNA (in the enhanced linear amplification methods).

The methods of the invention do not require thermocycling in that amplification can be performed isothermally. This feature provides numerous advantages, including facilitating automation and adaptation for high throughput amplification and/or analysis of nucleic acids. For example, sequencing methods based on the amplification methods of the invention are simplified by the ability to perform the reactions isothermally. Other methods that have been reported require thermal cycling for the separation of primer extension products from the target sequence. The isothermal reaction is faster than that afforded by thermal cycling and is suitable for performing sequencing of a target nucleic acid in miniaturized devices.

Another advantage of the methods of the invention is that only a single primer is required. A single primer is utilized to provide unidirectional primer extension that results in amplification of template nucleic acid. This obviates the numerous drawbacks associated with having to use primer pairs, for example cost of designing and making two sets of primers, the need to have prior knowledge of an additional sequence region within the template nucleic acid, and the increased probability that amplified products are the result of non-specific priming.

The linear isothermal amplification methods of the invention are also suitable for use for detection of nucleic acid targets, quantification of defined nucleic acid sequences, and the production of probes for defined nucleic acid sequences. The methods of the invention are useful for qualitative detection of a nucleic acid sequence, quantitative determination of the amount of the target nucleic acid sequence, detection of the presence of defined sequence alterations, as needed for genotyping, and sequencing. The products of the amplification according to the methods of the invention are single stranded and are readily detectable by various known nucleic acid detection methods.

The methods of the invention are further useful for multiplex analysis of nucleic acid sequences. That is to say, various target sequences may be amplified simultaneously in a single reaction mixture. The various target sequences may be part of a single genomic DNA, or may represent specific sequences of various nucleic acid targets, which may be present in a single test sample. For example, the methods of the invention are useful for the detection of the presence of various pathogens in a single biological sample. Similarly, the determination of various polymorphic sites in a single genomic DNA sample can be determined simultaneously in a single reaction.

It is understood that, with respect to all embodiments described herein, as generally "comprising" components or aspects, the invention also includes embodiments which "consist essentially of" these components or aspects. The invention also includes embodiments which "consist of" these components or aspect. This applies to all embodiments described herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Definitions

A "target sequence," as used herein, is a polynucleotide sequence of interest, for which amplification is desired. The target sequence may be known or not known, in terms of its actual sequence. Generally, a "template," as used herein, is a polynucleotide that contains the target nucleotide sequence. In some instances, the terms "target sequence," "template DNA," "template polynucleotide," "target nucleic acid," "target polynucleotide," and variations thereof, are used interchangeably.

"Amplification," as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1–20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. Oligonucleotides in the present invention include the composite primer, TSO, PTO and blocker sequence. The terms "oligonucleotide" and "polynucleotide" are not mutually exclusive. The description above for polynucleotides is equally and fully applicable to oligonucleotides.

A "primer" is generally a short single stranded polynucleotide, generally with a free 3'-OH group, that binds to a target potentially present in a sample of interest by hybridizing with a target sequence, and thereafter promotes polymerization of a polynucleotide complementary to the target.

A "termination polynucleotide sequence" or "termination sequence," as used interchangeably herein, is a polynucleotide sequence which effects cessation of DNA replication by DNA polymerase with respect to the template comprising the target sequence. A termination sequence comprises a portion (or region) that generally hybridizes to the template at a location 5' to the termination point (site). The hybridizable portion may or may not encompass the entire termination sequence. Examples of suitable termination polynucleotide sequences (such as blocker sequences and TSOs) are provided herein.

"Blocker sequence," or "blocking sequence" as used interchangeably herein, is an example of a termination sequence, and refers. to an oligonucleotide that binds, generally with high affinity, to the template nucleic acid at a location 5' to the termination site and effects cessation of DNA replication by DNA polymerase with respect to the template comprising the target sequence. Its 3' end may or may not be blocked for extension by DNA polymerase.

"Termination site," or "termination point," as used interchangeably herein, refers to the site, point or region of the template that is last replicated by the DNA polymerase before termination of polymerization (generally, primer extension) or template switch. For example, with respect to a TSO, it is the position or region in the target sequence that is complementary to the 3' end of the primer extension product prior to switching template from the template polynucleotide to the unhybridized portion of the TSO.

"Protopromoter sequence," and "propromoter sequence," as used herein, refer to a single-stranded DNA sequence region which, in double-stranded form is capable of mediating RNA transcription. In some contexts, "protopromoter sequence," "protopromoter," "propromoter sequence," "propromoter," "promoter sequence," and "promoter" are used interchangeably.

"Template switch oligonucleotide (TSO)," as used herein, refers to an oligonucleotide that comprises a portion (or region) that is hybridizable to a template at a location 5' to the termination site of primer extension and that is capable of effecting a template switch in the process of primer extension by a DNA polymerase. TSOs are generally known in the art. "Template switch" refers to a change in template nucleic acid, generally from the target nucleic acid to the unhybridized portion of a TSO, during the course of a single round of primer extension.

"Propromoter template oligonucleotide (PTO)," as used herein, refers to an oligonucleotide that comprises a propromoter sequence and a portion, generally a 3' portion, that is hybridizable to the 3' region of a primer extension product. The propromoter sequence and the hybridizable portion may be the same, distinct or overlapping nucleotides of an oligonucleotide.

A first sequence which "corresponds" to second sequence, such as an RNA portion of a composite primer, means that the first sequence has significant sequence identity with respect to the second sequence. This term is generally used in the context of detecting mutations, or characterizing sequences of a target.

To "inhibit" is to decrease or reduce an activity, function, and/or amount as compared to a reference.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s).

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence. For example, an RNA portion which is adjacent to a 5' DNA portion of a composite primer directly abuts that region. For an illustration of this example, see FIGS. 1A–C.

A "reaction mixture" is an assemblage of components, which, under suitable conditions, react to form a complex (which may be an intermediate) and/or a product(s).

"A", "an" and "the", and the like, unless otherwise indicated include plural forms.

"Comprising" means including.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, deletion or insertion. Single nucleotide polymorphism (SNP) is also a sequence mutation as used herein.

"Single stranded conformation polymorphism," and "SSCP," as used herein, generally refer to the specific conformation of a single stranded nucleic acid as is affected by its specific nucleic acid sequence. Alteration of the sequence of the single stranded polynucleotide, such as single nucleotide substitution, deletions or insertions, result in change, or polymorphism, of the conformation of the single stranded polynucleotide. The conformation of the polynucleotide is generally detectable, identifiable and/or distinguishable using methods known in the art, such as electrophoretic mobility as measured by gel electrophoresis, capillary electrophoresis, and/or susceptibility to endonuclease digestion.

"Microarray" and "array," as used interchangeably herein, refer to an arrangement of a collection of nucleotide sequences in a centralized location. Arrays can be on a solid substrate, such as a glass slide, or on a semi-solid substrate, such as nitrocellulose membrane. The nucleotide sequences can be DNA, RNA, or any permutations thereof.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 20, more preferably from about 3 to about 18, even more preferably from about 5 to about 15 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 20, more preferably from about 3 to about 18, even more preferably from about 5 to about 15 nucleotides.

"Detection" includes any means of detecting, including direct and indirect detection. For example, "detectably fewer" products may be observed directly or indirectly, and the term indicates any reduction (including no products). Similarly, "detectably more" product means any increase, whether observed directly or indirectly.

Components and Reaction Conditions Used in the Methods of the Invention

Template Nucleic Acid

The nucleic acid (NA) target to be amplified includes nucleic acids from any source in purified or unpurified form, which can be DNA (dsDNA and ssDNA) or RNA, including TRNA, mRNA, rRNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof Otaining and purifying nucleic acids use standard techniques in the art. Amplification of an RNA target will require initial cDNA synthesis, as known in the art. Amplification of a DNA-RNA hybrid would require denaturation of the hybrid to obtain a ssDNA, or denaturation followed by reverse transcription to obtain a cDNA. The target nucleic acid can be only a minor fraction of a complex mixture such as a biological sample and can be obtained from various biological material by procedures well known in the art.

The initial step of the amplification of a target nucleic acid sequence is rendering the target single stranded. If the target nucleic acid is a double stranded (ds) DNA, the initial step is target denaturation. The denaturation step may be thermal denaturation or any other method known in the art, such as alkali treatment. If the target is RNA, the initial step may be the synthesis of a single stranded cDNA. Techniques for the synthesis of cDNA from RNA are known in the art.

Composite Primer

The amplification methods of the invention employ a single composite primer that is composed of RNA and DNA portions. The composite design of the primer is critical for subsequent displacement of the primer extension product by binding of a new (additional) composite primer and the extension of the new primer by the polymerase. In addition, cleavage of the RNA portion of the primer extension product leads to generation of amplification product which is not a substrate for amplification by the composite primer, as described below.

Composite primers for use in the methods and compositions of the present invention comprise at least one RNA portion that is capable of (a) binding (hybridizing) to a sequence on the target nucleic acid (template) independent of hybridization of the DNA portion(s) to a sequence on the target nucleic acid; and (b) being cleaved with a ribonuclease when hybridized to the target DNA. The composite primers bind to the target nucleic to form a partial heteroduplex in which only the RNA portion of the primer is cleaved upon contact with a ribonuclease such as RNase H, while the target strand remains intact, thus enabling annealing of another composite primer.

The composite primers also comprise a 3' DNA portion that is capable of hybridization to a sequence on the target nucleic acid (template) such that its hybridization to the target sequence (template) is favored over that of the nucleic acid strand that is displaced from the target nucleic acid by the DNA polymerase. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the target nucleic acid is favored over the hybridization of the homologous sequence in the 5' end of the displaced strand to the target nucleic acid.

Generation of primers suitable for extension by polymerization is well known in the art, such as described in PCT Pub. No. WO99/42618 (and references cited therein). The composite primer comprises a combination of RNA and DNA (see definition above), with the 3'-end nucleotide being a nucleotide suitable for nucleic acid extension. The 3'-end nucleotide can be any nucleotide or analog that when present in a primer, is extendable by a DNA polymerase. Generally, the 3'-end nucleotide has a 3'-OH. Suitable primers include those that comprise at least one portion of RNA and at least one portion of DNA. As shown in Example 5 (showing the relative performance of the various primers used for amplification of *E. coli* J gene) for one gene, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the present invention comprises a 3'-DNA portion and at least one intervening RNA portion (i.e., an RNA portion between DNA portions).

The length of an RNA portion in a composite primer comprising a 3'-DNA portion and an RNA portion can be preferably from about 1 to about 25, more preferably from about 3 to about 20, even more preferably from about 4 to about 15, and most preferably from about 5 to about 10 nucleotides. In some embodiments of a composite primer comprising a 3'-DNA portion and an RNA portion, an RNA portion can be at least about any of 1, 3, 4, 5 nucleotides, with an upper limit of about any of 10, 15, 20, 25, 30 nucleotides.

The length of the 5'-RNA portion in a composite primer comprising a 5'-RNA portion and a 3'-DNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In other embodiments of a composite primer comprising a 5'-RNA portion and a 3'-DNA portion, the 5'-RNA portion can be at least about any of 3, 5, 7, 8, 10 nucleotides, with an upper limit of about any of 15, 17, 18, 20 nucleotides.

In embodiments of a composite primer comprising a 5'-RNA portion and a 3'-DNA portion further comprising non-5'-RNA portion(s), a non-5'-RNA portion can be preferably from about 1 to about 7 nucleotides, more preferably from about 2 to about 6 nucleotides, and most preferably from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10 nucleotides.

In embodiments of a composite primer comprising a 5'-RNA portion and a 3'-DNA portion, in which the 5'-RNA portion is adjacent to the 3'-DNA portion, the length of the 5'-RNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10 nucleotides, with an upper limit of about any of 15, 17, 18, 20 or nucleotides.

The length of an intervening RNA portion in a composite primer comprising 5'- and 3'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 5'- and 3'-DNA portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 3'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 3'-DNA portion and at least one intervening RNA portion, further comprising a 5'-RNA portion, the 5'-RNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20 nucleotides.

The length of the 3'-DNA portion in a composite primer comprising a 3'-DNA portion and an RNA portion can be preferably from about 1 to about 20, more preferably from about 3 to about 18, even more preferably from about 5 to about 15, and most preferably from about 7 to about 12 nucleotides. In some embodiments of a composite primer comprising a 3'-DNA portion and an RNA portion, the 3'-DNA portion can be at least about any of 1, 3, 5, 7, 10 nucleotides, with an upper limit of about any of 10, 12, 15, 18, 20, 22 nucleotides.

The length of the 3'-DNA portion in a composite primer comprising a 5'-RNA portion and a 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 5'-RNA portion and a 3'-DNA portion, the 3' DNA portion can be at least about any of 1, 3, 5, 7, 1 0 nucleotides, with an upper limit of about any of 10, 12, 15, 18, 20, 22 nucleotides.

In embodiments of a composite primer comprising a 5'-RNA portion and a 3'-DNA portion, further comprising non-3'-DNA portion(s), a non-3'-DNA portion can be preferably from about 1 to about 10 nucleotides, more preferably from about 2 to about 8 nucleotides, and most preferably from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12 nucleotides.

In embodiments of a composite primer comprising a 5'-RNA portion and a 3'-DNA portion in which the 5'-RNA portion is adjacent to the 3'-DNA portion, the length of the 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion in a composite primer comprising 5'-and 3'-DNA portions with at least one intervening RNA portion can be preferably from about I to about 10 nucleotides, more preferably from about 2 to about 8 nucleotides, and most preferably from about 3 to about 6 nucleotides. In some embodiments of a primer comprising 5'- and 3'-DNA portions with at least one intervening RNA portion, a non-3'-DNA portion can be at least about any of 1, 2, 3, 5 nucleotides, with an upper limit of about any of 6, 8, 10, 12 nucleotides.

The length of the 3'-DNA portion in a composite primer comprising 5'- and 3'-DNA portions with at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion (i.e., any DNA portion other than the 3'-DNA portion) in a composite primer comprising a 3'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12 nucleotides. The length of the 3'-DNA portion in a composite primer comprising a 3'-DNA portion and at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 20, 22 nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer).

The total length of the composite primer can be preferably from about 10 to about 40 nucleotides, more preferably from about 15 to about 30 nucleotides, and most preferably from about 20 to about 25 nucleotides. In some embodiments, the length can be at least about any of 10, 15, 20, 25 nucleotides, with an upper limit of about any of 25, 30, 40, 50 nucleotides. It is understood that the length can be greater or less, as appropriate under the reaction conditions of the methods of this invention.

To achieve hybridization (which, as is well known and understood in the art, depends on other factors such as, for example, ionic strength and temperature), composite primers for use in the methods and compositions of the present invention are preferably of at least about 60%, more preferably at least about 75%, even more preferably at least about 90%, and most preferably at least about 95% complementarity to the target nucleic acid. The individual DNA and RNA portions of the composite primers are preferably of at least about 60%, more preferably at least about 75%, even more preferably at least about 90%, and most preferably at least about 95% complementarity to the target nucleic acid.

As described herein, one or more composite primers may be used in an amplification reaction.

A Polynucleotide Comprising a Termination Polynucleotide Sequence

In some embodiments of the methods of the present invention, especially if transcription-based amplification is used, a polynucleotide comprising a termination sequence is included, examples of which are provided below.

Template Switch Oligonucleotide

A second oligonucleotide that can be used in the amplification methods of the invention is a termination switch oligonucleotide (TSO). In one embodiment, the TSO functions as a termination sequence. In another embodiment, the TSO functions as a termination sequence and provides a propromoter sequence.

Previously described amplification methods based on template switch oligonucleotide were restricted in the concentration of this oligonucleotide due to inhibition of hybridization of the second primer, or the second hybridization step of the same primer when the method is designed to utilize a single primer species. The methods of the invention are free of this limitation. In contrast to previously described methods using TSOs, the template switch oligonucleotide can be used at high concentration for amplification according to the methods of the present invention. This feature ensures efficient hybridization of the oligonucleotide to the target strand, and maximizes the yield of the tri molecular complex, the substrate for primer extension and template switch. An additional attribute of this feature is the efficient hybridization of the displaced primer extension product to the template switch oligonucleotide to form a substrate for the RNA polymerase, as described.

Figure 2A:
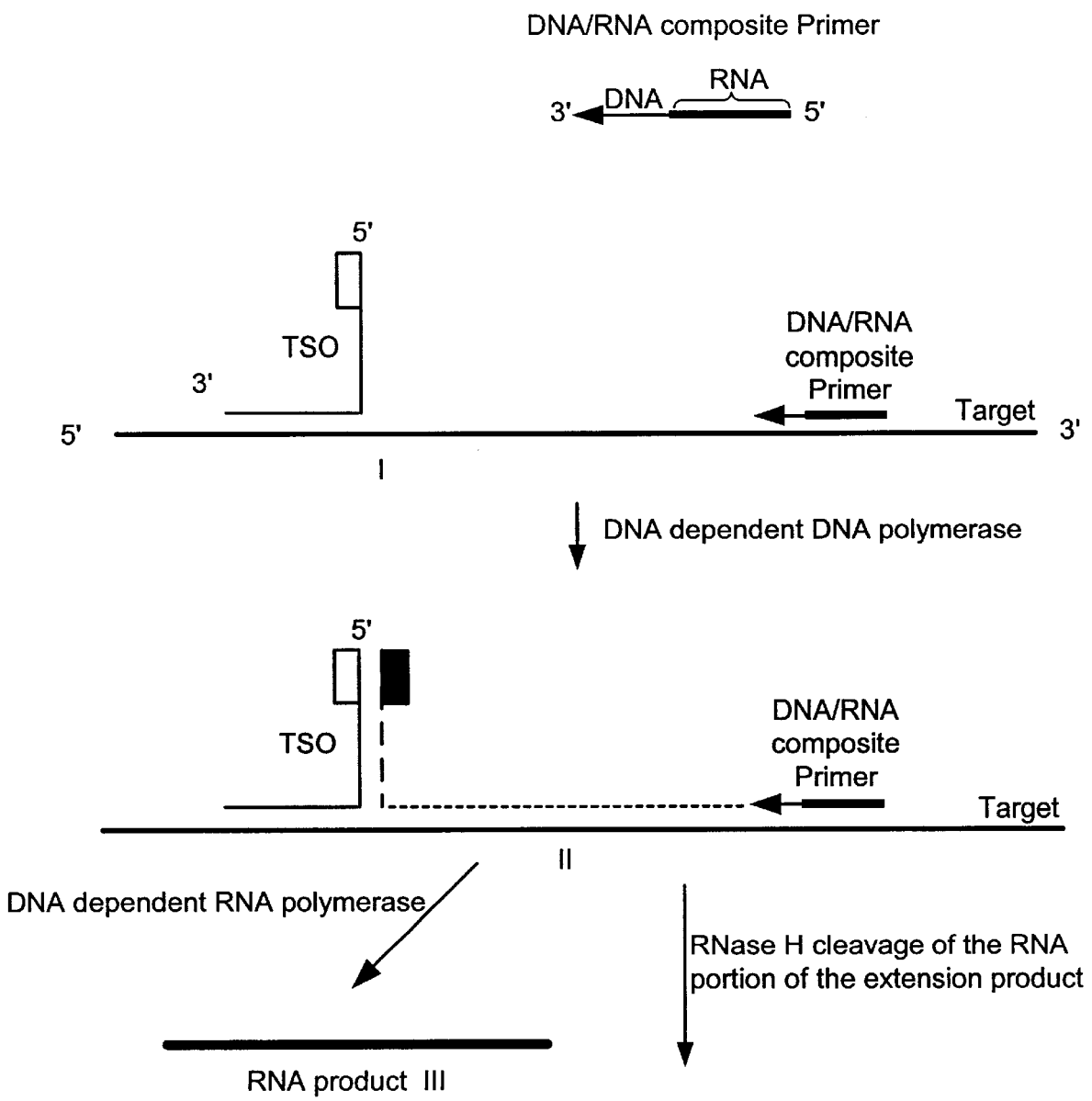
FIGS. 2A–2C is a diagrammatic representation of an enhanced single primer isothermal linear nucleic acid amplification process involving transcription, using a template switch oligonucleotide sequence.
Figure 2B:
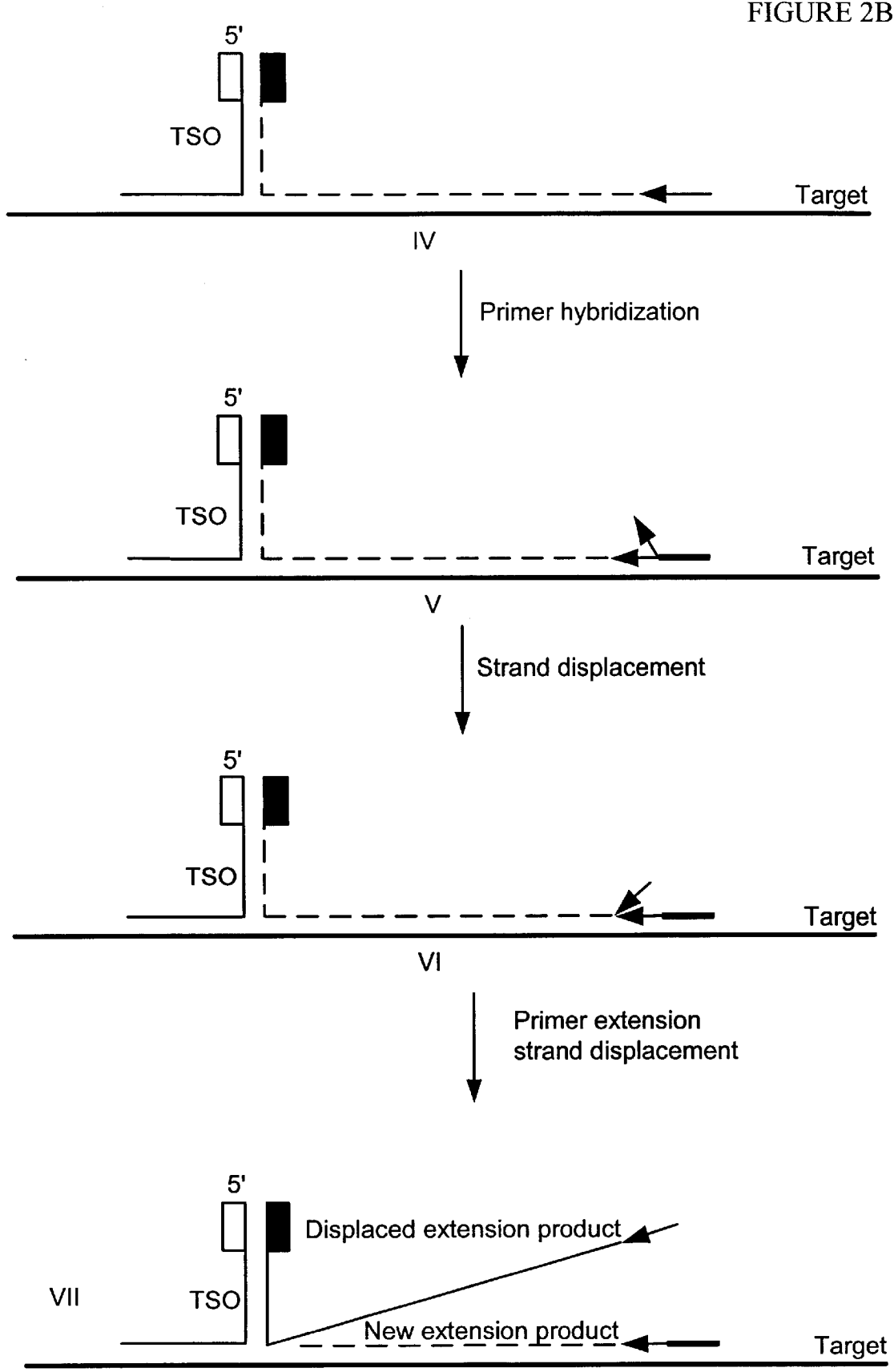
Figure 2C:
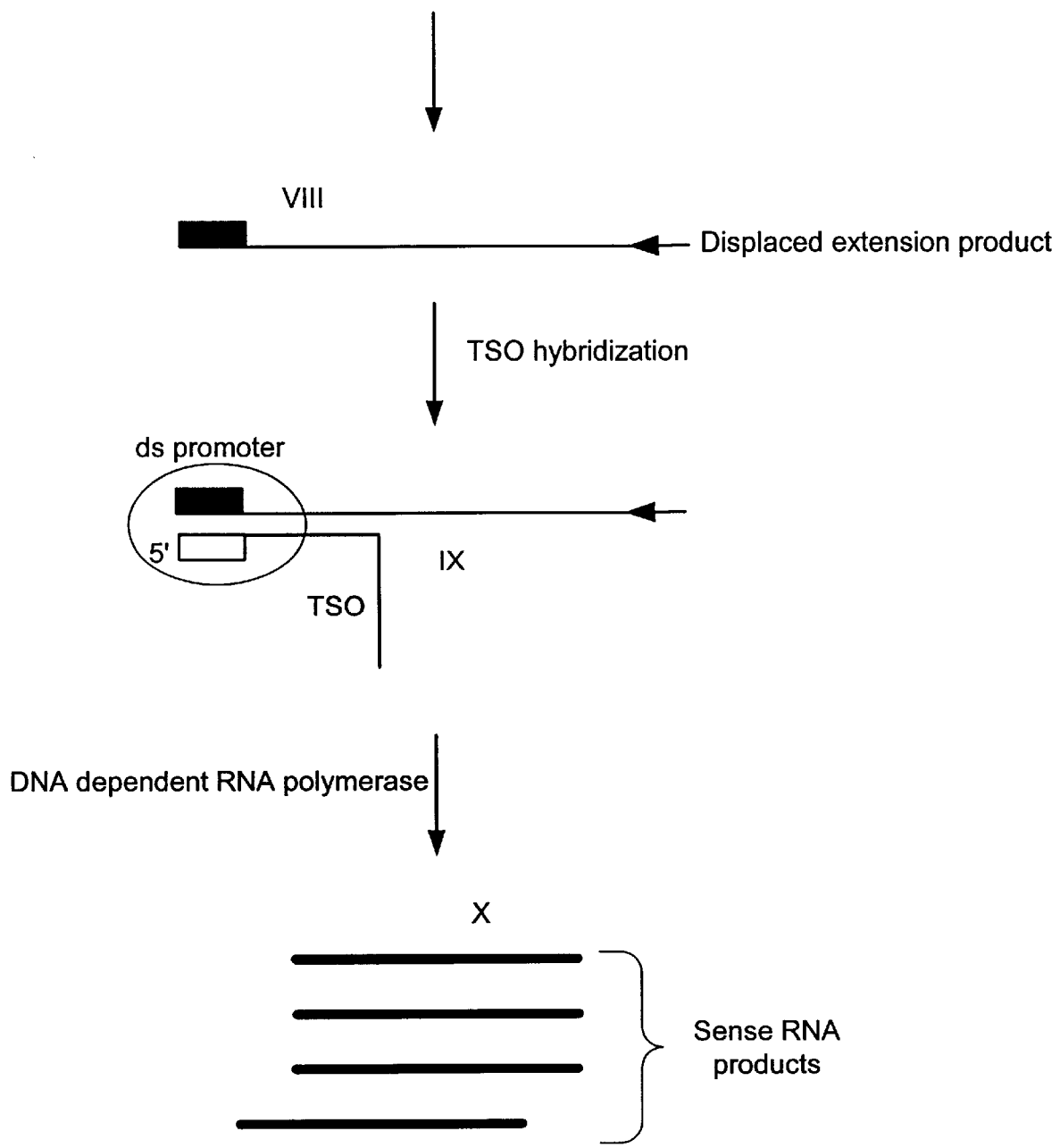
Figure 3A:
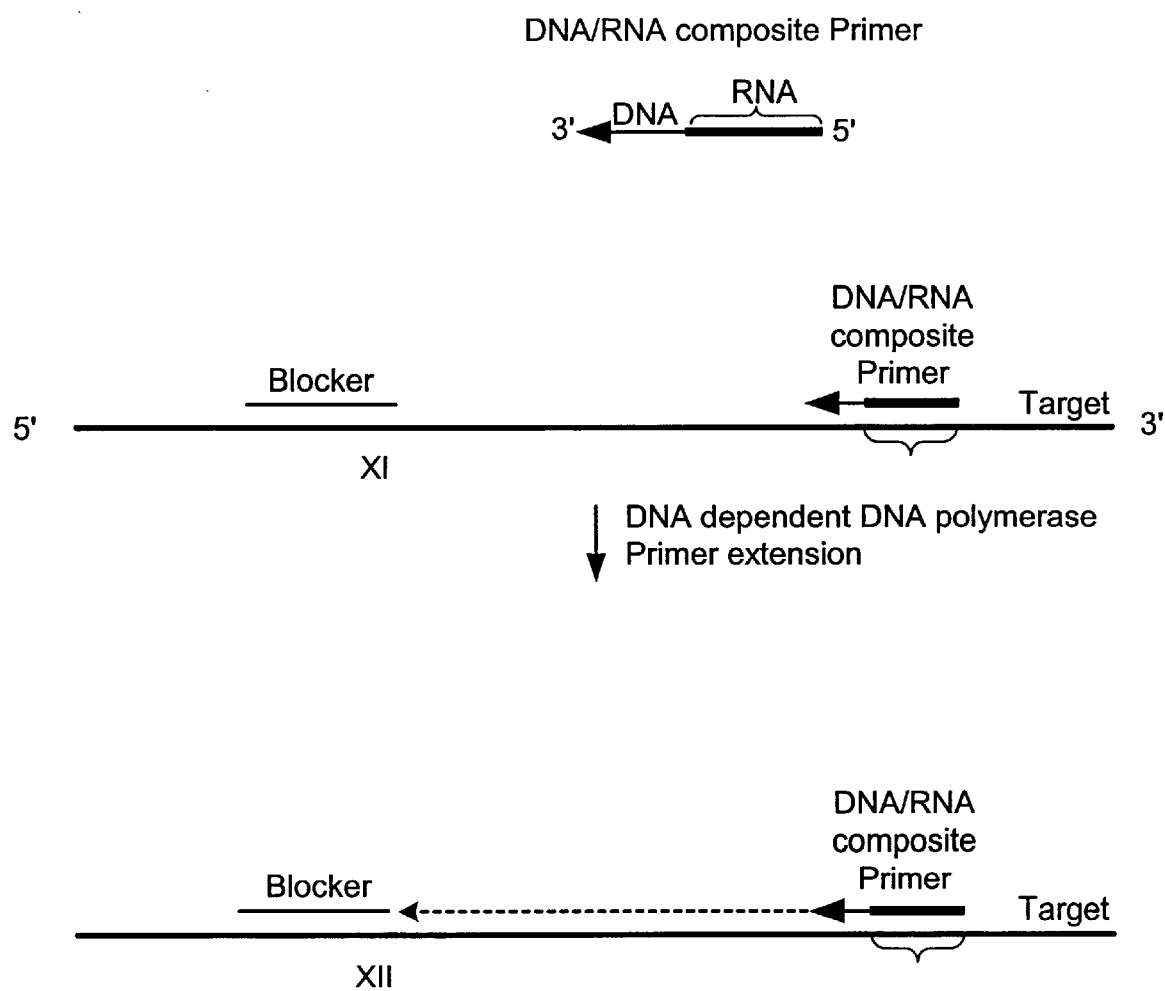
FIGS. 3A–3D is a diagrammatic representation of an enhanced single composite primer isothermal linear nucleic acid amplification process involving transcription, using a blocker sequence component.
Figure 3B:
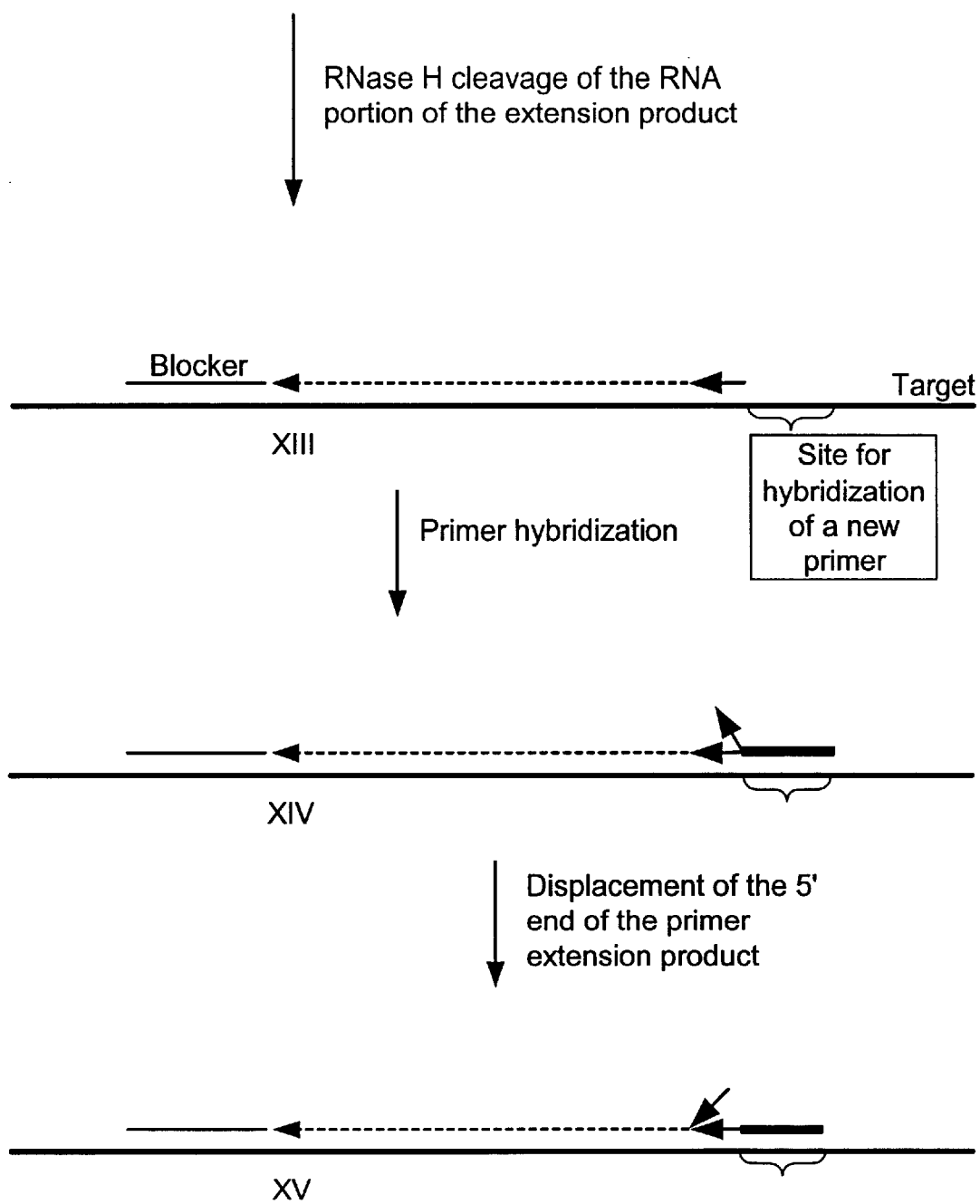
Figure 3C:
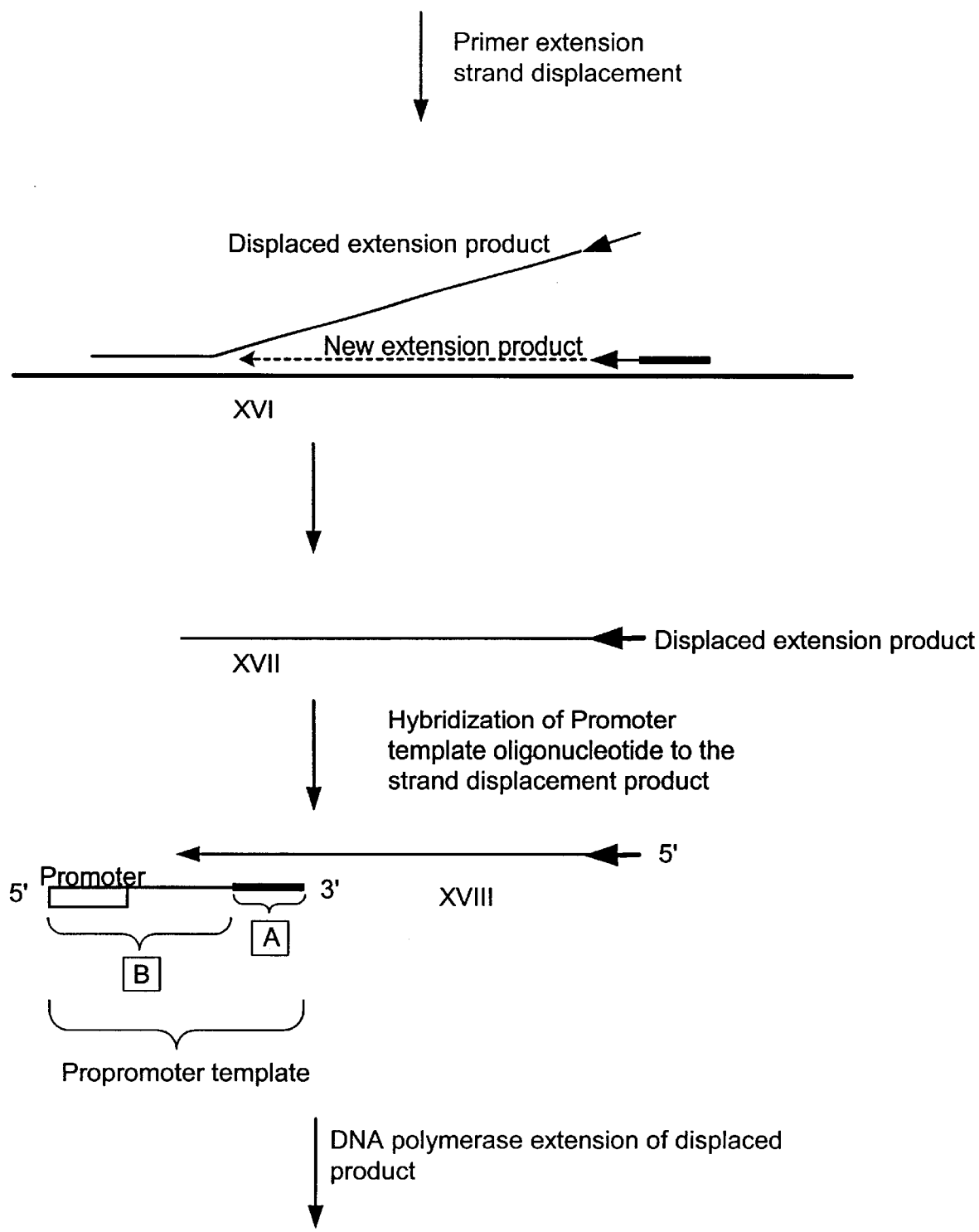
Figure 3D:
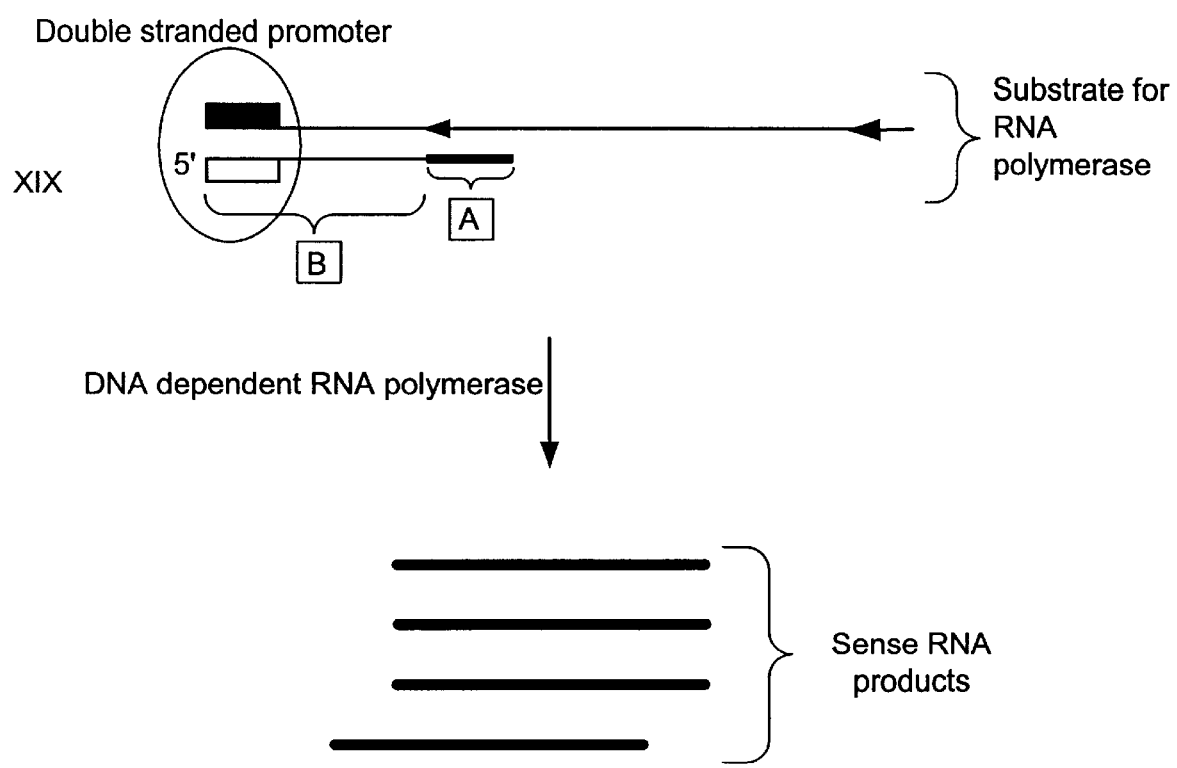

A TSO comprises a 3' portion that can hybridize to the target and a 5' portion which is designed for strand switch during polymerization (see FIGS. 2A–C). Design of a TSO that would effect strand switch is known in the art, such as was previously described in Patel et al., Proc. Nat'l Acad. Sci. USA 1996, 93:2969–2974.

The 3' portion hybridizes to the template at a location 5' to the position or region in the template polynucleotide that is complementary to the 3' end of the primer extension product prior to switching template from the template polynucleotide to the unhybridized portion of the TSO ("termination site").

In one embodiment, strand switch is promoted by the presence of mutually complementary short sequences in the TSO segments immediately 5' and 3' to the junction between the hybridized and non-hybridized portions of the TSO. Without intending to be bound by theory, one explanation is that in the event that the primer extension product is extended into the portion of the target nucleic acid that is hybridized to the TSO (through displacement of the hybridized portion of the TSO), the 3' end of the primer extension product would comprise a short sequence that can bind to its complementary short sequence in the segment of the TSO immediately adjacent to the junction between the hybridized and non-hybridized portions of the TSO. This increases the efficiency of template switching by increasing the probability that the primer extension product would switch to the TSO tail portion as a template. The length of the short complementary sequences is preferably from about 3 to about 20 nucleotides, more preferably from about 5 to about 15 nucleotides, and most preferably from about 7 to about 10 nucleotides. In some embodiments, length is at least about any of 1, 3, 5, 7, 10 nucleotides, with an upper limit of about any of 10, 15, 20, 25 nucleotides. It is understood that the length can be greater or less, as appropriate under the reaction conditions of the methods of this invention.

In some embodiments, the 5' portion of the TSO comprises a sequence (hereinafter "propromoter sequence"), that is designed for formation of a double stranded promoter of an RNA polymerase. This embodiment of the TSO would function both as a termination sequence and to provide a promoter template. In this embodiment, the propromoter sequence of the TSO serves as a template for incorporation of a propromoter sequence (generally complementary to the propromoter sequence of the template TSO) into the primer extension product. Subsequent hybridization of a TSO comprising a propromoter sequence that is hybridizable to the propromoter sequence of the primer extension product results in formation of a double stranded promoter capable of effecting transcription by a suitable RNA polymerase. Promoter sequences that allow transcription of a template DNA are known in the art, as are methods of obtaining and/or making them. Preferably, the promoter sequence is selected to provide optimal transcriptional activity of the particular RNA polymerase used. Criteria for such selection, i.e., a particular promoter sequence particularly favored by a particular RNA polymerase, are also known in the art. For example, the sequences of the promoters for transcription by T7 DNA dependent RNA polymerase and SP6 are known in the art. The promoter sequence can be from a prokaryotic or eukaryotic source.

In one embodiment, the promoter sequence is adjacent to a sequence that is designed to provide for enhanced, or more optimal, transcription by the RNA polymerase used. In some embodiments, the sequence is not related (i.e., it does not substantially hybridize) to the target nucleic acid. More optimal transcription occurs when transcriptional activity of the polymerase from a promoter that is operatively linked to said sequence is greater than from a promoter that is not so linked. The sequence requirements for optimal transcription are generally known in the art as previously described for various DNA dependent RNA polymerases, such as in U.S. Pat. Nos. 5,766,849 and 5,654,142.

In a preferred embodiment, a segment of the 3' portion of the TSO (including the entire 3' portion that hybridizes to target) that hybridizes to the template DNA is attached to the template DNA such that displacement of the TSO by the polymerase that effects primer extension is substantially, or at least sufficiently, inhibited. Suitable methods for achieving such attachment includes techniques known in the art, such as using a cytosine analog that contains a G-clamp heterocycle modification (described in Flanagan et al., Proc. Natl. Acad. Sci. USA 1999, 96(7):3513–8); and locked nucleic acids (described, e.g., in Kumar et al., Bioorg. Med. Chem Lett. 1998, 8(16):2219–22; and Wahlestedt et al., Proc. Natl. Acad. Sci. USA 2000, 97(10):5633–8). Other suitable methods include using, where appropriate, sequences with a high GC content and/or cross-linking. Any of these methods for obtaining enhanced attachment may be used alone or in combination. Displacement of the TSO is substantially or sufficiently inhibited if the polymerase switches template from the target nucleic acid strand to the unhybridized portion of the TSO in at least about 25%, preferably at least about 50%, more preferably at least about 75%, and most preferably at least about 90%, of the events of primer extension. Substantially or sufficiently inhibited TSO displacement can also be empirically indicated if the amplification methods lead to a satisfactory result in terms of amount of the desired product. Generally, under a given set of conditions, the "modified" TSO binds more tightly to template as compared to a TSO not so modified.

The length of the TSO portion that hybridizes to the target nucleic acid strand is preferably from about 15 to 50 nucleotides, more preferably from about 20 to 45 nucleotides, and most preferably from about 25 to 40 nucleotides. In other embodiments, the length is at least about any of the following: 10, 15, 20, 25, 30; and less than about any of the following: 35, 40, 45, 50, 55. It is understood that the length can be greater or less, as appropriate under the reaction conditions of the methods of this invention. The complementarity of the TSO portion that hybridizes to the target nucleic acid strand is preferably at least about 25%, more preferably at least about 50%, even more preferably at least about 75%, and most preferably at least about 90%, to its intended binding sequence on the target nucleic acid.

Blocker Sequence

In some embodiments, the primer extension termination sequence is provided by a blocker sequence. The blocker sequence is a polynucleotide, usually a synthetic polynucleotide, that is single stranded and comprises a sequence that is hybridizable, preferably complementary, to a segment of target nucleic acid sequence 5' of the position in the target sequence that is complementary to the 3' end of the primer extension product ("termination site"). The blocker comprises nucleotides that bind to the target nucleic acid with an affinity, preferably a high affinity, such that the blocker sequence resists displacement by DNA polymerase in the course of primer extension, in preferably more than about 30%, more preferably more than about 50%, even more preferably more than about 75%, and most preferably more than about 90%, of primer extension events. The length and composition of the blocker polynucleotide should be such that excessive random non-specific hybridization is avoided under the conditions of the methods of the present invention. The length of the blocker polynucleotide is preferably from about 3 to about 30 nucleotides, more preferably from about 5 to about 25 nucleotides, even more preferably from about 8 to about 20 nucleotides, and most preferably from about 10 to about 15 nucleotides. In other embodiments, the blocker polynucleotide is at least about any of the following: 3, 5, 8, 10, 15; and less than about any of the following: 20, 25, 30, 35. It is understood that the length can be greater or less as appropriate under the reaction conditions of the methods of this invention. The complementarity of the blocker polynucleotide is preferably at least about 25%, more preferably at least about 50%, even more preferably at least about 75%, and most preferably at least about 90%, to its intended binding sequence on the target nucleic acid.

In one embodiment, the blocker sequence comprises a segment that hybridizes to the target DNA is attached to the target DNA such that displacement of the blocker sequence by the polymerase that effects primer extension is substantially, or at least sufficiently, inhibited. Suitable means for achieving such attachment and determining substantial, or sufficient, inhibition of displacement are as described above for TSO used in the methods of the present invention.

In one embodiment, the blocker polynucleotide cannot function efficiently as a primer for nucleic acid extension (i.e., extension from the blocker sequence is reduced, or inhibited). Techniques for blocking the primer function of the blocker polynucleotide include any that prevent addition of nucleotides to the 3' end of the primer by a DNA polymerase. Such techniques are known in the art, including, for example, substitution or modification of the 3' hydroxyl group, or incorporation of a modified nucleotide, such as a dideoxynucleotide, in the 3'-most position of the blocker polynucleotide that is not capable of anchoring addition of nucleotides by a DNA polymerase.

Polynucleotide Comprising a Propromoter and a Region Which Hybridizes to a Displaced Primer Extension Product Some embodiments employ a polynucleotide comprising a propromoter and a region which hybridizes to a displaced primer extension product. In some embodiments, the polynucleotide is a TSO which contains a propromoter sequence, as discussed above. In other embodiments, the propromoter sequence is contained in a PTO, as described below.

Propromoter Template Oligonucleotide

In some embodiments, the methods employ a promoter sequence for transcription which is provided by a propromoter template oligonucleotide (PTO).

A PTO for use in the methods and compositions of the present invention is a single-stranded polynucleotide, generally DNA, comprising a propromoter sequence that is designed for formation of a ds promoter of an RNA polymerase, and a portion capable of hybridizing to the 3' end of the primer extension product. In a preferred embodiment, the propromoter sequence is located in the 5' portion of the oligonucleotide and the hybridizing sequence is located in the 3' portion of the oligonucleotide. In one embodiment, and most typically, the promoter and hybridizing sequences are different sequences. In another embodiment, the promoter and hybridizing sequences overlap in sequence identity. In yet another embodiment, the promoter and hybridizing sequences are the same sequence, and thus are in the same location on the PTO. In the embodiments wherein hybridization of the PTO to the primer extension product results in a duplex comprising an overhang (the 5' end of the PTO that does not hybridize to the displaced primer extension product, typically comprising all or part of the propromoter sequence), DNA polymerase fills in the overhang to create a double stranded promoter capable of effecting transcription by a suitable RNA polymerase.

Promoter sequences that allow transcription of a template DNA are known in the art and have been discussed above. Preferably, the promoter sequence is selected to provide optimal transcriptional activity of the particular RNA polymerase used. Criteria for such selection, i.e., a particular promoter sequence particularly favored by a particular RNA polymerase, is also known in the art. For example, the sequences of the promoters for transcription by T7 DNA dependent RNA polymerase and SP6 are known in the art. The promoter sequence can be from a prokaryotic or eukaryotic source.

In some embodiments, the PTO comprises an intervening sequence between a propromoter sequence and a portion capable of hybridizing to the 3' end of the primer extension product. Suitable length of the intervening sequence can be empirically determined, and can be at least about 1, 2, 4, 6, 8, 10, 12, 15 nucleotides. Suitable sequence identity of the intervening sequence can also be empirically determined, and the sequence is designed to preferably, but not necessarily, enhance degree of amplification as compared to omission of the sequence. In one embodiment, the intervening sequence is a sequence that is designed to provide for enhanced, or more optimal, transcription by the RNA polymerase used. Generally, the sequence is not related (i.e., it does not substantially hybridize) to the target nucleic acid. More optimal transcription occurs when transcriptional activity of the polymerase from a promoter that is operatively linked to said sequence is greater than from a promoter that is not so linked. The sequence requirements for optimal transcription are generally known in the art as previously described for various DNA dependent RNA polymerases, such as in U.S. Pat. Nos. 5,766,849 and 5,654,142, and can also be empirically determined.

In another embodiment, the PTO comprises a sequence that is 5' to the propromoter sequence, i.e., the PTO comprises additional nucleotides (which may or may not be transcriptional regulatory sequences) located 5' to the pro-promoter sequence. Generally, but not necessarily, the sequence is not hybridizable to the primer extension product.

In one embodiment, the PTO cannot function efficiently as a primer for nucleic acid extension. Techniques for blocking the primer function of the PTO include any that prevent addition of nucleotides to the 3' end of the PTO by a DNA polymerase. Such techniques are known in the art, including, for example, substitution or modification of the 3' hydroxyl group, or incorporation of a modified nucleotide, such as a dideoxynucleotide, in the 3'-most position of the PTO that is not capable of anchoring addition of nucleotides by a DNA polymerase. It is also possible to block the 3' end using a label, or a small molecule which is a member of a specific binding pair, such as biotin.

The length of the portion of the PTO that hybridizes to the displaced primer extension product is preferably from about 5 to about 50 nucleotides, more preferably from about 10 to about 40 nucleotides, even more preferably from about 15 to about 35 nucleotides, and most preferably from about 20 to 30 nucleotides. In some embodiments, the hybridizing portion is at least about any of the following: 3, 5, 10, 15, 20; and less than about any of the following: 30,40, 50, 60. The complementarity 5 of the hybridizing portion is preferably at least about 25%, more preferably at least about 50%, even more preferably at least about 75%, and most preferably at least about 90%, to its intended binding sequence on the target nucleic acid.

DNA Polymerase, Ribonuclease and RNA Polymerase

The amplification methods of the invention employs the following enzymes: a DNA polymerase, ribonuclease such as RNase H, and, optionally a DNA dependent RNA polymerase.

DNA polymerases for use in the methods and compositions of the present invention are capable of effecting extension of the composite primer according to the methods of the present invention. Accordingly, a preferred polymerase is one that is capable of extending a nucleic acid primer along a nucleic acid template that is comprised at least predominantly of deoxynucleotides. The polymerase should be able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Preferably, the polymerase has little or no 5'->3' exonuclease activity so as to minimize degradation of primer, termination or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'->3' exonuclease activity has been deleted, are known in the art and are suitable for the amplification methods described herein. Suitable DNA polymerases for use in the methods and compositions of the present invention include those disclosed in U.S. Pat. Nos. 5,648,211 and 5,744,312, which include exo⁻Vent (New England Biolabs), exo⁻Deep Vent (New England Biolabs), Bst (BioRad), exo⁻Pfu (Stratagene), Bca (Panvera), sequencing grade Taq (Promega), and thermostable DNA polymerases from ther-moanaerobacter thermohydrosulfuricus. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as described in U.S. Pat. No. 5,744,312 (and references cited therein). Preferably, the DNA polymerase has little to no proofreading activity.

The ribonuclease for use in the methods and compositions of the present invention is capable of cleaving ribonucleotides in an RNA/DNA hybrid. Preferably, the ribonuclease cleaves ribonucleotides regardless of the identity and type of nucleotides adjacent to the ribonucleotide to be cleaved. It is preferred that the ribonuclease cleaves independent of sequence identity. Examples of suitable ribonucleases for the methods and compositions of the present invention are well known in the art, including ribonuclease H (RNase H).

The DNA-dependent RNA polymerase for use in the methods and compositions of the present invention are known in the art. Either eukaryotic or prokaryotic polymerases may be used. Examples include T7, T3 and SP6 RNA polymerases. Generally, the RNA polymerase selected is capable of transcribing from the promoter sequence provided by the TSO or PTO as described herein. Generally, the RNA polymerase is a DNA dependent polymerase, which is preferably capable of transcribing from a single stranded DNA template so long as the promoter region is double stranded.

In general, the enzymes used included in the methods and compositions of the present invention should not produce substantial degradation of the nucleic acid components of said methods and compositions.

Reaction Conditions and Detection

Appropriate reaction media and conditions for carrying out the methods of the present invention are those that permit nucleic acid amplification according to the methods of the present invention. Such media and conditions are known to persons of skill in the art, and are described in various publications, such as U.S. Pat. No. 5,679,512 and PCT Pub. No. WO99/42618. For example, a buffer maybe Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 10 mM, and most preferably from about I to 5 mM. The reaction medium can also include other salts, such as KCl, that contribute to the total ionic strength of the medium. For example, the range of a salt such as KCl is preferably from about 0 to about 100 mM, more preferably from about 0 to about 75 mM, and most preferably from about 0 to about 50 mM. The reaction medium can further include additives that could affect performance of the amplification reactions, but that are not integral to the activity of the enzyme components of the methods. Such additives include proteins such as BSA, and non-ionic detergents such as NP40 or Triton. Reagents, such as DTT, that are capable of maintaining enzyme activities can also be included. Such reagents are known in the art. Where appropriate, an RNase inhibitor (such as Rnasine) that does not inhibit the activity of the RNase employed in the method can also be included. Any aspect of the methods of the present invention can occur at the same or varying temperatures. Preferably, the reactions are performed isothermally, which avoids the cumbersome thermocycling process. The amplification reaction is carried out at a temperature that permits hybridization of the oligonucleotides (primer, TSO, blocker sequence, and/or PTO) of the present invention to the template polynucleotide and that does not substantially inhibit the activity of the enzymes employed. The temperature can be in the range of preferably about 25° C. to about 85° C., more preferably about 30° C. to about 75° C., and most preferably about 37° C. to about 70° C. In some embodiments that include RNA transcription, the temperature for the transcription steps is lower than the temperature(s) for the preceding steps. In these embodiments, the temperature of the transcription steps can be in the range of preferably about 25° C. to about 85° C., more preferably about 30° C. to about 75° C., and most preferably about 37° C. to about 70° C.

Nucleotide and/or nucleotide analogs, such as deoxyribonucleoside triphosphates, that can be employed for synthesis of the primer extension products in the methods of the invention are provided in the amount of from preferably about 50 to about 2500 $\mu$M, more preferably about 100 to about 2000 $\mu$M, even more preferably about 500 to about 1700 $\mu$M, and most preferably about 800 to about 1500 $\mu$M. In some embodiments, a nucleotide or nucleotide analog whose presence in the primer extension strand enhances displacement of the strand (for example, by causing base pairing that is weaker than conventional AT, CG base pairing) is included. Such nucleotide or nucleotide analogs include deoxyinosine and other modified bases, all of which are known in the art. Nucleotides and/or analogs, such as ribonucleoside triphosphates, that can be employed for synthesis of the RNA transcripts in the methods of the invention are provided in the amount of from preferably about 0.25 to about 6 mM, more preferably about 0.5 to about 5 mM, even more preferably about 0.75 to about 4 mM, and most preferably about 1 to about 3 mM.

The oligonucleotide components of the amplification reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Composite primers, TSO, PTO and the blocker sequence can each be provided at about or at least about any of the following concentrations: 50 nM, 100 nM, 500 nM, 1000 nM, 2500 nM, 5000 nM.

In one embodiment, the foregoing components are added simultaneously at the initiation of the amplification process. In another embodiment, components are added in any order prior to or after appropriate timepoints during the amplification process, as required and/or permitted by the amplification reaction. Such timepoints, some of which are noted below, can be readily identified by a person of skill in the art. The enzymes used for nucleic acid amplification according to the methods of the present invention can be added to the reaction mixture either prior to the nucleic acid denaturation step, following the denaturation step, or following hybridization of the primer and/or blocker sequence to the target DNA, as determined by their thermal stability and/or other considerations known to the person of skill in the art.

The amplification reactions can be stopped at various timepoints, and resumed at a later time. Said timepoints can be readily identified by a person of skill in the art. Methods for stopping the reactions are known in the art, including, for example, cooling the reaction mixture to a temperature that inhibits enzyme activity. Methods for resuming the reactions are also known in the art, including, for example, raising the temperature of the reaction mixture to a temperature that permits enzyme activity. In some embodiments, one or more of the components of the reactions is replenished prior to, at, or following the resumption of the reactions. Alternatively, the reaction can be allowed to proceed (i.e., from start to finish) without interruption.

The detection of the amplification product is indicative of the presence of the target sequence. Quantitative analysis is also feasible. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the present invention can also be extended to analysis of sequence alterations and sequencing of the target nucleic acid. Further, detection could be effected by, for example, examination of translation products from RNA amplification products.

Amplification Methods of the Present Invention

The following are examples of the amplification methods of the invention. It is understood that various other embodiments may be practiced, given the general description provided above. For example, reference to using a composite primer means that any of the composite primers described herein may be used.

In one aspect of the present invention, a method for amplifying a nucleotide sequence complementary to a target nucleotide sequence is provided. In this method, isothermal linear nucleic acid sequence amplification is achieved. In another aspect, a method for amplifying a target polynucleotide sequence wherein the amplified product is sense RNA is provided, which is sometimes referred to herein as an "enhanced" linear amplification method. In one embodiment, a method of enhanced isothermal linear nucleic acid sequence amplification which is TSO-based is provided (hereinafter "Method 1"). In another embodiment, a method of enhanced isothermal linear nucleic acid sequence amplification which is blocker sequence and PTO-based is provided (hereinafter "Method 2").

Linear Nucleic Acid Sequence Amplification Resulting in Complementary DNA Product When not linked to transcription, the amplification method of the invention provides for isothermal linear amplification of a target nucleic acid sequence. The method utilizes a single composite primer. In one embodiment, the method also employs a termination sequence, such as a blocker sequence as described in Method 2, or a TSO, as described in Method 1. Methods 1 and 2 are described below. Insofar as the linear amplification is not linked to transcription, the components and steps leading to formation of a complex comprising a promoter sequence for a DNA dependent RNA polymerase, are not included.

The termination sequence (either TSO or blocker sequence component, if used) is added for producing a product of defined 3'-end. In some embodiments, natural sequence(s) within the template 5' of the primer binding site inhibits nucleic acid polymerization such that termination of primer extension is achieved. Such natural sequences are known in the art, for example, GC rich sequences, or can be empirically determined. Use of a termination sequence is particularly beneficial when amplifying genomic DNA so as to provide a defined end of primer extension. When this feature is not desired, the isothermal linear amplification according to the methods of the invention can be carried out without a termination sequence. The isothermal linear amplification further utilizes two enzymes, a DNA polymerase and a ribonuclease such as RNase H. Schematic description of the linear isothermal nucleic acid amplification of the invention is shown in FIGS. 1A–C.

Similar to Methods 1 and 2 as described below, the linear amplification method is designed to amplify a single stranded DNA target. When the target to be amplified is ds DNA, the target is first denatured to produce single stranded target. Target denaturation may be carried out using methods known in the art, such as heat or alkali treatment. When the target is single stranded RNA, such as mRNA or viral RNA, the target is first transcribed to produce cDNA target by methods known in the art.

Figure 1B:
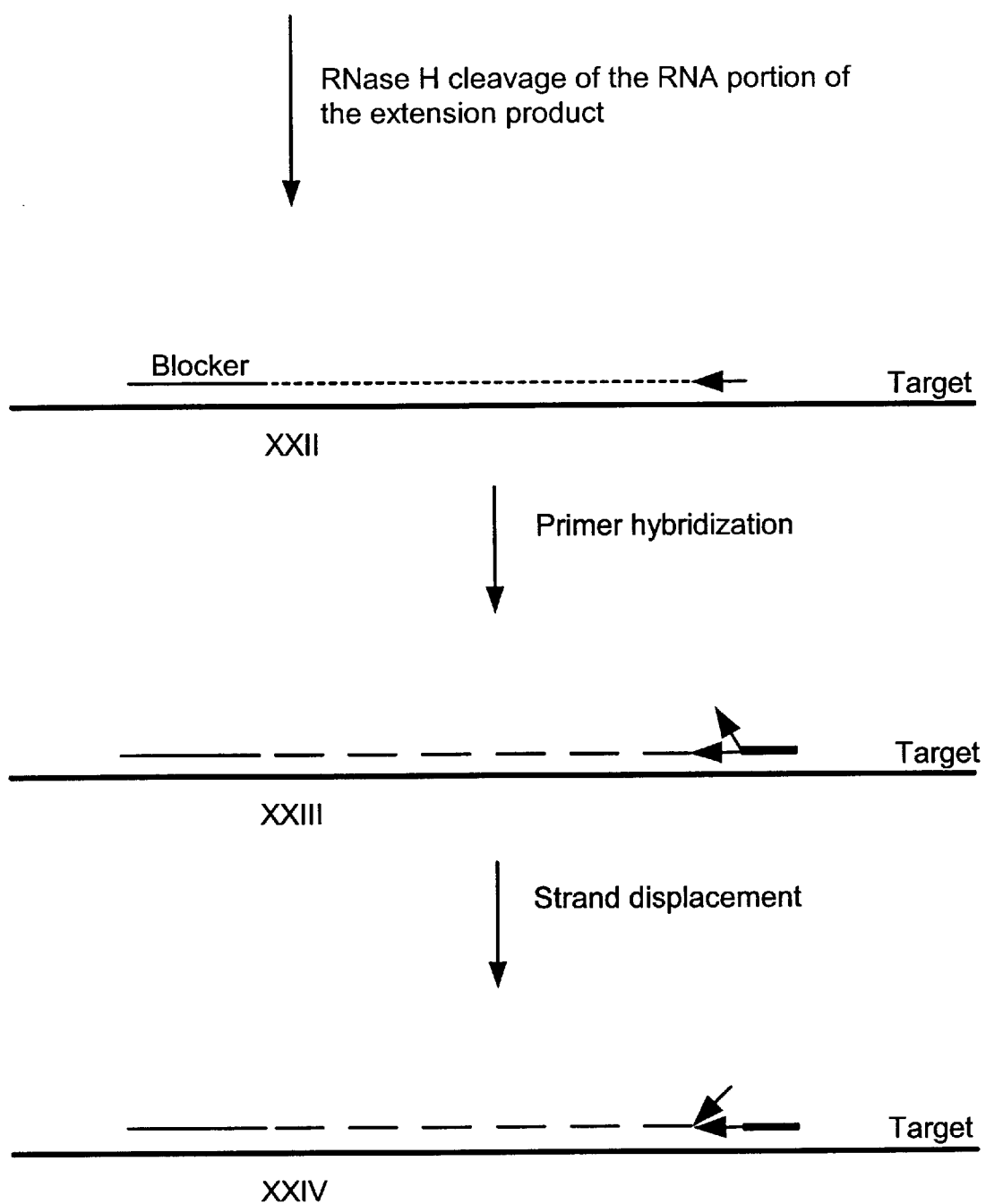
Figure 1C:
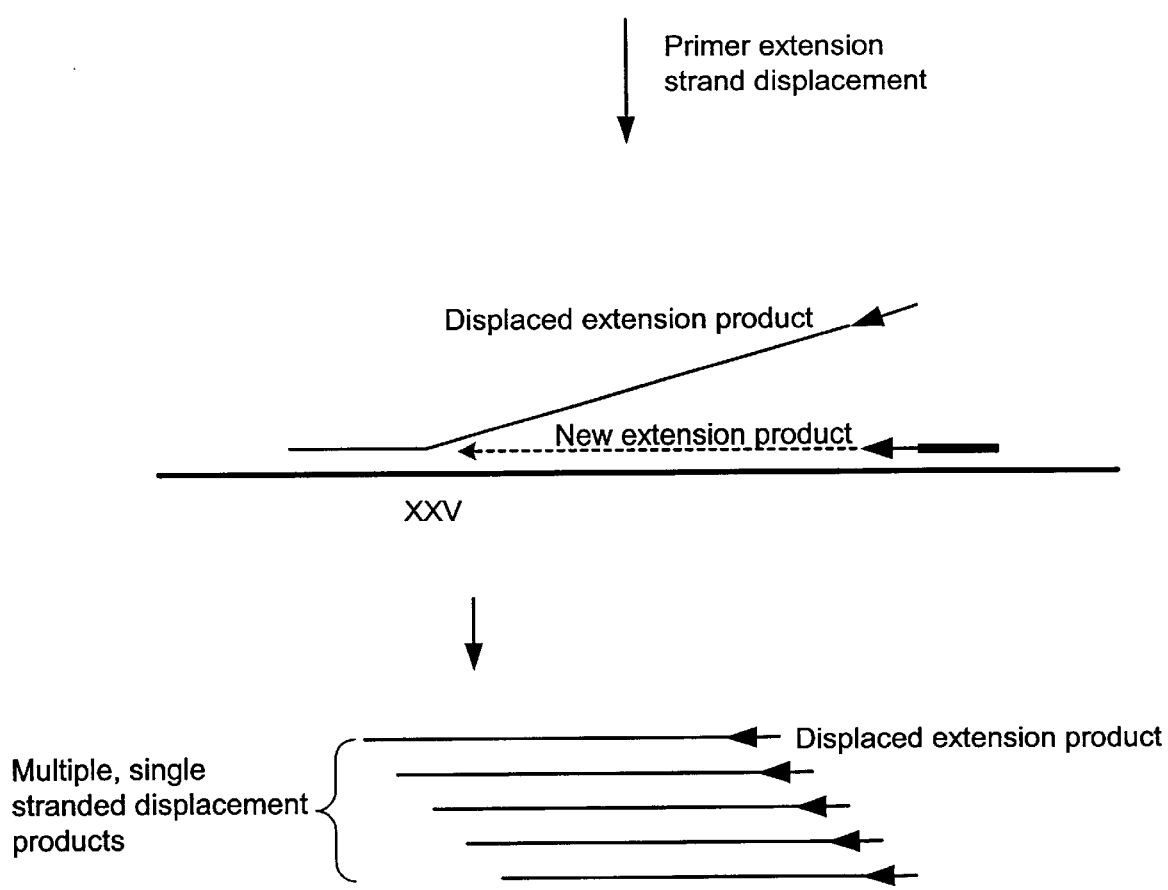

As shown in FIGS. 1A–C, the linear isothermal amplification method of the invention comprises steps similar to the initial steps of the enhanced linear amplification methods (Methods 1 and 2) described below and in FIGS. 2A–C and 3A–D. The target nucleic acid is combined with a composite primer, DNA polymerase, a ribonuclease such as RNase H and optionally a blocker sequence component or TSO, as described above. In one embodiment, each amplification reaction includes composite primers of one identical sequence. In another embodiment, each amplification reaction includes a mixture of composite primer variants, wherein the variants represent two or more homologous but non-identical sequences, and wherein all are capable of hybridizing to the same target nucleic acid sequence. The complementarity is preferably at least about 50%, more preferably at least about 75%, and most preferably at least about 90%. Advantages of this embodiment include the ability to introduce different sequences of interest into the primer extension products. In yet another embodiment, each amplification reaction includes a mixture of composite primers, wherein the primers represent two or more non-identical sequences that are of low or no homology, and wherein the primers preferentially hybridize to different target nucleic acid sequences or different sites along the same target nucleic acid strand. Advantages of this embodiment include multiplex detection and/or analysis of target nucleic acids through amplification of a plurality of target nucleic acid species in a single amplification reaction.

FIGS. 1A–C illustrates an embodiment that includes a termination sequence. The composite primer and the termination sequence (TSO or blocker sequence component) hybridize to the same strand of the target, to form a tri molecular complex, XX (FIGS. 1A–C). The 3'-end of the composite primer is extended along the target strand by the polymerase, up to the site of hybridizing of the TSO or blocker sequence component, to yield complex XXI (FIGS. 1A–C). A ribonuclease such as RNase H cleaves the RNA, generally the 5'-RNA, portion of the extended primer of complex XXI (FIGS. 1A–C) to produce complex XXII (FIGS. 1A–C). A second composite primer binds to complex XXII (FIGS. 1A–C) by hybridization of the RNA, generally the 5' RNA, portion to yield complex XXIII (FIGS. 1A–C). The free 3' portion of the bound composite primer then displaces the 5' end of the primer extension product and hybridizes to the target to form complex XXIV (FIGS. 1A–C). The hybridization of the 3' end of the composite primer to the target is generally favored over the hybridization of the 5' end of the primer extension product since the hybridized 3' end of the primer is a site of binding of the DNA polymerase which will then extend the 3' end of the primer along the target. Primer extension results in displacement of the first primer extension product to yield complex XXV (FIGS. 1A–C). The process is repeated to yield multiple single stranded DNA displacement products which are generally complementary to the target sequence.

The single stranded DNA (i.e., the displaced primer extension products) of the isothermal linear amplification method are readily detectable by any of many detection methods known in the art. Various homogeneous or heterogeneous detection methods suitable for the detection of single stranded nucleic acid molecules were previously described, including identification by size and/or migration properties in gel electrophoresis, or by hybridization to sequence-specific probes.

The detection of the amplification product is indicative of the presence of the target sequence. Quantitative analysis is also feasible. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the present invention can also be extended to analysis of sequence alterations and sequencing of the target nucleic acid.

The production of at least 1, at least 10, at least about 100, at least about 1000, at least about $10^5$, at least about $10^7$, at least about $10^9$, at least about $10^{12}$, complementary copies of each copy of template polynucleotide can be expected, thus leading to at least 1, at least 10, at least 100, at least 1000, at least about $10^5$, at least about $10^7$, at least about $10^9$, at least about $10^{12}$-fold enhancement with respect to each copy of template polynucleotide.

Enhanced Linear Amplification Resulting in Sense RNA Product

The present invention also provides methods for amplifying a target polynucleotide sequence wherein the amplified product is RNA containing the sense sequence (i.e., same sequence as target). Amplification of target nucleic acid according to Method 1, which results in the generation of a unique intermediate amplification product comprising target and template switch oligonucleotide (TSO)-related portions, provides for coupling of the linear amplification to transcription. The complex formed by the hybridization of the template switch oligonucleotide and the displaced primer extension product is a substrate for transcription by the RNA polymerase, which generates an RNA product of the same sense as the initial target sequence. Similarly, amplification of nucleic acid target according to Method 2 results in formation of a displaced primer extension product which when hybridized to the promoter template oligonucleotide forms a complex, which is a substrate for the RNA polymerase. As in Method 1, this process results in coupling of the linear amplification to transcription. The production of preferably at least about 1, more preferably at least about 50, even more preferably at least about 75, still more preferably at least about 100, and most preferably at least about 1000, RNA transcript products from each primer extension product is expected, thus leading to preferably at least about 1, more preferably at least about 50, even more preferably at least about 75, still more preferably at least about 100, and most preferably at least about 1000-fold enhancement with respect to the non-transcription linked methods of amplification.

Below are two exemplary methods.

Method 1—TSO-based enhanced linear nucleic acid amplification

In one embodiment, the TSO-based linear amplification method of the present invention is linked to transcription from the primer extension products to provide enhanced nucleic acid amplification. A schematic description of this novel amplification method, Method 1, is shown in FIGS. 2A–C.

The TSO-based nucleic acid amplification method of the invention employs a single composite primer, as described above. A second oligonucleotide used in the amplification method of the invention is a template switch oligonucleotide (TSO), also as described above. The amplification method of the invention employs the following enzymes: a DNA polymerase, a ribonuclease such as RNase H, and a DNA dependent RNA polymerase. The nucleic acid target to be amplified can be DNA or RNA. Amplification of an RNA target will require initial cDNA synthesis, as known in the art.

The new TSO-based enhanced linear amplification method of the present invention can produce multiple copies of an RNA product homologous (i.e., sense) to the target DNA sequence.

The single stranded target nucleic acid is combined with the composite primer, a TSO oligonucleotide, DNA polymerase, ribonuclease such as RNase H, a DNA dependent RNA polymerase, and nucleotides, such as deoxyribonucleoside triphosphates (dNTPs) and ribonuceoside triphosphates (rNTPs), in a reaction medium suitable for nucleic acid hybridization and amplification, as known in the art. Suitable reaction medium and conditions are as described above. In one embodiment, transcription is performed at a different temperature, generally lower, than that of the preceding steps. In another embodiment, all the steps of the methods are performed isothermally.

In one embodiment, each amplification reaction includes composite primers of one identical sequence. In another embodiment, each amplification reaction includes a mixture of composite primer variants, wherein the variants represent two or more homologous but non-identical sequences, and wherein all are capable of hybridizing to the same target nucleic acid sequence. The homology (sequence identity) is preferably at least about 50%, more preferably at least about 75%, and most preferably at least about 90%. Advantages of this embodiment include the ability to introduce different sequences of interest into the primer extension products. In yet another embodiment, each amplification reaction includes a mixture of composite primers, wherein the primers represent two or more non-identical sequences that are of low or no homology, and wherein the primers preferentially hybridize to different target nucleic acid sequences or different sites along the same target nucleic acid strand. Advantages of this embodiment include multiplex detection and/or analysis of target nucleic acids through amplification of a plurality of target nucleic acid species in a single amplification reaction.

In one embodiment, the TSO functions as a termination sequence and provides a propromoter sequence. In another embodiment, the TSO does not comprise a propromoter sequence. In this embodiment, a propromoter sequence is provided separately by another oligonucleotide, such as a PTO, that comprises a propromter sequence and is hybridizable to the 3' portion of the primer extension product such that transcription of the primer extension product can occur.

The single composite primer and the TSO then hybridize to the same strand of the nucleic acid to be amplified. The two oligonucleotides may be added to the sample suspected of containing the nucleic acid target prior to the target nucleic acid denaturation step. Hybridization of the two oligonucleotides to the target strand results in the formation of the tri molecular complex I (FIGS. 2A–C).

A DNA polymerase carries out primer extension. The primer is extended along the target nucleic acid strand of complex I (FIGS. 2A–C), up to the site of TSO hybridization. Template switching from the target strand to the 5' unhybridized portion of the TSO, and further primer extension along the TSO template results in the formation of the tri molecular complex II. The last comprises a target nucleic acid, the TSO and the first primer extension product. The first primer extension product is a unique DNA comprising both a target dependent portion (i.e., sequence complementary to the target nucleic acid) and a TSO dependent portion (i.e., sequence complementary to the unhybridized portion of the TSO).

Complex II (FIGS. 2A–C) is a substrate for both an RNA polymerase and a ribonuclease such as RNase H. The DNA dependent RNA polymerase binds to the functional ds promoter of complex II and transcribes the first primer extension product to produce a sense RNA product m (FIGS. 2A–C). A ribonuclease, such as RNase H, which is specific for degradation of the RNA strand of an RNA/DNA heteroduplex, degrades the 5' portion of the primer extension product in complex II to form the tri molecular complex IV.

Free composite primer hybridizes to the primer complementary site of the target nucleic acid in complex IV (FIGS. 2A–C). This hybridization results in formation of complex V (FIGS. 2A–C) in which only the RNA portion, generally the 5' RNA portion, of the primer is hybridized to the target strand. Displacement of the 5' most portion of the primer extension product by the 3' DNA portion of the partially hybridized primer will result in formation of complex VI (FIGS. 2A–C), which is a substrate for a DNA polymerase. Extension of the primer along the target strand (VII; FIGS. 2A–C) results in displacement of the first primer extension product from the complex. Repeated primer extensions and strand displacements result in generation of multiple copies of polynucleotides that are at least substantially complementary to the target nucleic acid.

The primer extension product generated as described above is used as a template for transcription in the embodiment wherein TSO that comprises a propromoter sequence is provided. The displaced primer extension product (VIII; FIGS. 2A–C) hybridizes to free TSO oligonucleotide to form the partial duplex IX (FIGS. 2A–C). Complex (duplex) IX comprises a double stranded portion at one end and two non-complementary single strands respectively derived from the primer extension product and the TSO. The double stranded portion of this partial duplex contains a fully functional double stranded promoter for the DNA dependent RNA polymerase. The last binds to the promoter of the partial duplex IX and transcribes the primer extension product to form multiple copies of a sense RNA product X (FIGS. 2A–C).

The products of the amplification described above can be detected by either homogenous or heterogeneous detection methods, including identification by size and/or migration properties in gel electrophoresis, or by hybridization to sequence-specific probes. The detection of the amplification product is indicative of the presence of the target nucleic acid. Quantitative analysis is also feasible. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. Further extension of the new amplification method to analysis of sequence alteration and sequencing of the target nucleic acid are also feasible, as described below.

Method 2—Blocker Sequence-Based Enhanced Nucleic Acid Amplification

In another embodiment, the blocker sequence-based linear amplification method of the present invention is linked to transcription from the primer extension products to provide enhanced nucleic acid amplification. This alternative enhanced linear amplification, Method 2, which does not involve a template switch step, is shown in FIGS. 3A–D.

Method 2 utilizes the single composite primer, as in Method 1, as described above, a blocker sequence component which is either an oligonucleotide or an oligonucleotide analog, which, as described above, is further able to hybridize to a sequence on the same target nucleic acid strand as the single primer, and a third oligonucleotide, the promoter template (PTO), which, as described above, comprises a 3'-portion which is able to hybridize (and is preferably complementary) to the 3'-end of the displaced extension product and a 5'-portion which includes at its 5' end a sequence of a promoter for a DNA dependent RNA polymerase. As in the TSO described above, the sequence immediately adjacent to the promoter sequence is designed to provide for preferably optimal transcriptional activity by the RNA polymerase used in the amplification according to the method of the invention. The blocker sequence component is designed to hybridize to the target sequence at a site which is located upstream, towards the 5' end of the target, relative to the site of hybridization of the single primer. Stated alternatively, and as described above, the blocker sequence hybridizes to a segment of target nucleic acid sequence 5' of the position in the target sequence that is complementary to the 3' end of the primer extension product. The blocker sequence binds with sufficiently high affinity so as to block primer extension at the site of blocker hybridization to the target. This feature provides a strong stop for primer extension by the polymerase and defines the 3'-end of the primer extension product.

As in Method 1, the target nucleic acid for amplification according to Method 2 is a single stranded DNA. When the target nucleic acid is a ds DNA, the target is first rendered single stranded by denaturation. The denaturation of the ds DNA target may be carried out by heating or any other known method known in the art, such as alkali treatment. When the target nucleic acid is RNA, such as mRNA, the target is first reverse transcribed by methods known in the art to produce a cDNA that is then amplified according to the method of the invention.

The single stranded nucleic acid target is combined with the single composite primer, the blocker component, the propromoter template (PTO), DNA polymerase, ribonuclease such as RNase H, a DNA dependent RNA polymerase, and nucleotides, such as NTPs (e.g., dNTPs and rNTPs), as was described for Method 1. Suitable reaction medium and conditions are as described above. In one embodiment, the transcription is performed at a different temperature, generally lower, than that of the preceding steps. In another embodiment, all the steps of the methods are performed isothermally.

In one embodiment, each amplification reaction includes composite primers of one identical sequence. In another embodiment, each amplification reaction includes a mixture of composite primer variants, wherein the variants represent two or more homologous but non-identical sequences, and wherein all are capable of hybridizing to the same target nucleic acid sequence. The homology (sequence identity) is preferably at least about 50%, more preferably at least about 75%, and most preferably at least about 90%. Advantages of this embodiment include the ability to introduce different sequences of interest into the primer extension products. In yet another embodiment, each amplification reaction includes a mixture of composite primers, wherein the primers represent two or more non-identical sequences that are of low or no homology, and wherein the primers preferentially hybridize to different target nucleic acid sequences or different sites along the same target nucleic acid strand. Advantages of this embodiment include multiplex detection and/or analysis of target nucleic acids through amplification of a plurality of target nucleic acid species in a single amplification reaction.

The single composite primer and the blocker sequence component hybridize to the same target strand to form a tri molecular complex. The primer is extended along the target up to the site of hybridization of the blocker sequence, to form complex XII (FIGS. 3A–D).

As in Method 1, a ribonuclease, such as RNase H, cleaves the RNA portion, generally the 5' RNA portion, of the single composite primer of complex XII to form complex xm (FIGS. 3A–D). As described above, the enzyme is specific for cleaving the RNA strand of an RNA/DNA hybrid, and does not digest single stranded RNA. Thus, the ribonuclease does not degrade the free composite primer. The following steps, as illustrated in FIGS. 3A–D, of primer hybridization (XIV), displacement of the 5' end of the primer extension product by the 3'-DNA portion of the composite primer (XV), primer extension and displacement of the first primer extension product (XVI), proceed as in Method 1, to yield multiple copies of the displaced extension product (XVII). Unlike the displacement product of Method 1, XVII is fully complementary to the target sequence and does not comprise a 3' end portion which is not complementary to the target. Repeated primer extensions and strand displacements result in generation of multiple copies of polynucleotides that are complementary to the target nucleic acid.

The promoter template oligonucleotide (PTO) binds to the displaced extension product to form complex XVIII (FIGS. 3A–D), by hybridization of the 3' end portion (A) of the propromoter template to the 3' end of the displaced primer extension product. As described above, the 3' end of the PTO may be blocked or not. When the 3' end of the propromoter template is not blocked, the template will be extended along the displaced primer extension product. The 3' end of the displaced product will be extended by the nucleotide (DNA) polymerase along the B portion (see FIGS. 3A–D) of the hybridized propromoter template to form complex XIX, which comprises at its one end a ds promoter sequence that can be utilized by the DNA dependent RNA polymerase. Complex XIX is depicted in FIGS. 3A–D as the product of hybridization of a promoter template in which the 3' end is blocked for extension by the polymerase. Alternatively, when the 3' end of the promoter template is not blocked extension of the 3' end along the displaced primer extension product results in formation of a fully double stranded complex. DNA-dependent RNA polymerase will transcribe the extended displaced primer extension product of complex XIX, in both forms (the choice of RNA polymerase must take into account its capability to transcribe from a ds and/or ss DNA template), that is to say either the partial duplex or the fully double stranded duplex forms of the complex. Multiple copies of a single stranded RNA products are produced by this transcription step.

The products of the amplification described above can be detected by either homogenous or heterogeneous detection methods, including identification by size and/or migration properties in gel electrophoresis, or by hybridization to sequence-specific probes. The detection of the amplification product is indicative of the presence of the target nucleic acid. Quantitative analysis is also feasible. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the present invention can also be extended to analysis of sequence alterations and sequencing of the target nucleic acid, as discussed below.

Methods Using the Amplification Methods and Compositions of the Invention

The methods and compositions of the present invention can be used for a variety of purposes. For purposes of illustration, methods of sequencing, genotyping (nucleic acid mutation detection), microarray preparation using the amplified nucleic acid products generated by the methods of the present invention, and characterizing nucleic acid sequences are described.

Isothermal Sequencing of Defined Nucleic Acid Targets Using the Linear Amplification Method of the Invention The linear isothermal amplification methods of the invention are useful, for example, for sequencing of a defined nucleic acid target sequence. The sequencing process is carried out as described for the amplification methods described herein. In addition to the nucleotides, such as natural deoxyribonucleotide tri phosphates (dNTPs), that are used for the amplification method according to the present invention, the sequencing reaction mixture also includes the appropriate nucleotide tri phosphate analogs, which may be labelled or unlabelled, that upon incorporation into a primer extension product effect termination of nucleotide polymerization. Such analogs are commonly used in other sequencing methods and are well known in the art, such as dideoxyribonucleotides. They may be labeled, e.g., with fluorochromes or radioisotopes. The labels may also be labels which are suitable for mass spectroscopy. The label may also be a small molecule which is a member of a specific binding pair, and can be detected following binding of the other member of the specific binding pair, such as biotin and streptavidin, respectively, with the last member of the binding pair conjugated to an enzyme that catalyzes the generation of a detectable signal that could be detected by methods such as colorimetry, fluorometry or chemiluminescence. All of the above examples are well known in the art. These are incorporated into the primer extension product by the polymerase and serve to stop further extension along the target sequence. The resulting truncated extension products are labeled. The accumulated multiple displaced primer extension products vary in length, according to the site of incorporation of each of the analogs, which represent the various sequence locations of a complementary nucleotide on the target sequence.

Analysis of the reaction products for elucidation of sequence information can be carried out using any of various methods known in the art. Such methods include gel electrophoresis and detection of the labeled bands using appropriate scanner, sequencing gel electrophoresis and detection of the radiolabeled band directly by phosphorescence such as Molecular Dynamics reader, capillary electrophoresis adapted with a detector specific for the labels used in the reaction, and the like. The label can also be a ligand for a binding protein which is used for detection of the label in combination with an enzyme conjugated to the binding protein, such as biotin-labeled chain terminator and streptavidin conjugated to an enzyme. The label is detected by the enzymatic activity of the enzyme, which generates a detectable signal. As with other sequencing methods known in the art, the sequencing reactions for the 4 nucleotide types (A, C, G, T) are carried out either in a single reaction vessel, or in separate reaction vessels (each representing 1 of the 4 nucleotide types). The choice of method to be used is dependent on practical considerations readily apparent to one skilled in the art, such as the nucleotide tri phosphate analogs and/or label used. Thus, for example, when each of the analogs is differentially labeled, the sequencing reaction can be carried out in a single vessel. The considerations for choice of reagent and reaction conditions for optimal performance of sequencing analysis according to the methods of the invention are similar to those for other previously described sequencing methods. The reagent and reaction conditions should be as described above for the linear nucleic acid amplification methods of the present invention.

Isothermal Sequencing of Defined Nucleic Acid Targets Using the Enhanced Linear Amplification Methods (Methods 1 and 2) of the Invention Transcription based sequencing was previously described in, for example, Sasaki et. al., PNAS, 95:3455–3460, 1998. The inclusion of rNTPs analogs, which may be labelled or unlabelled, that upon incorporation into an RNA transcript effects termination of rNTP polymerization in the reaction mixture for the enhanced linear amplification methods will result in production of truncated RNA products, which result from blocking of the RNA polymerase at sites of incorporation of the analogs. Suitable rNTP analogs are known in the art. The last are incorporated opposite the complementary nucleotide on the displaced extension product in the relevant complexes according to the method used (Method 1 or Method 2).

Analysis of the reaction products for the elucidation of sequence information is carried out using any one of a variety of methods as known in the art. Such methods include those described above for sequencing of defined nucleic acid targets using the (non-enhanced) linear amplification methods of the invention.

RNA Portion-Based Isothermal Mutation Detection Utilizing the Amplification Methods of the Invention The unique properties of the composite primer for use in the isothermal amplification methods of the invention provide the basis for an isothermal method for the detection of defined mutations, or polymorphic sites (such as SNPs), in a target nucleic acid sequence. The method is useful for genotyping, detection of mutation leading to drug resistance and the like. These methods are applicable to characterizing sequences in a region in the template strand which generally hybridize to the RNA portion of the composite primer— hence reference to 'defined" mutations, which are defined in terms of their location.

The target nucleic acid sequence suitable for the method of the invention is ss DNA. However, preparation of a ss DNA target from a ds DNA target or an RNA target can be carried out as described above and known in the art.

Figure 4A:
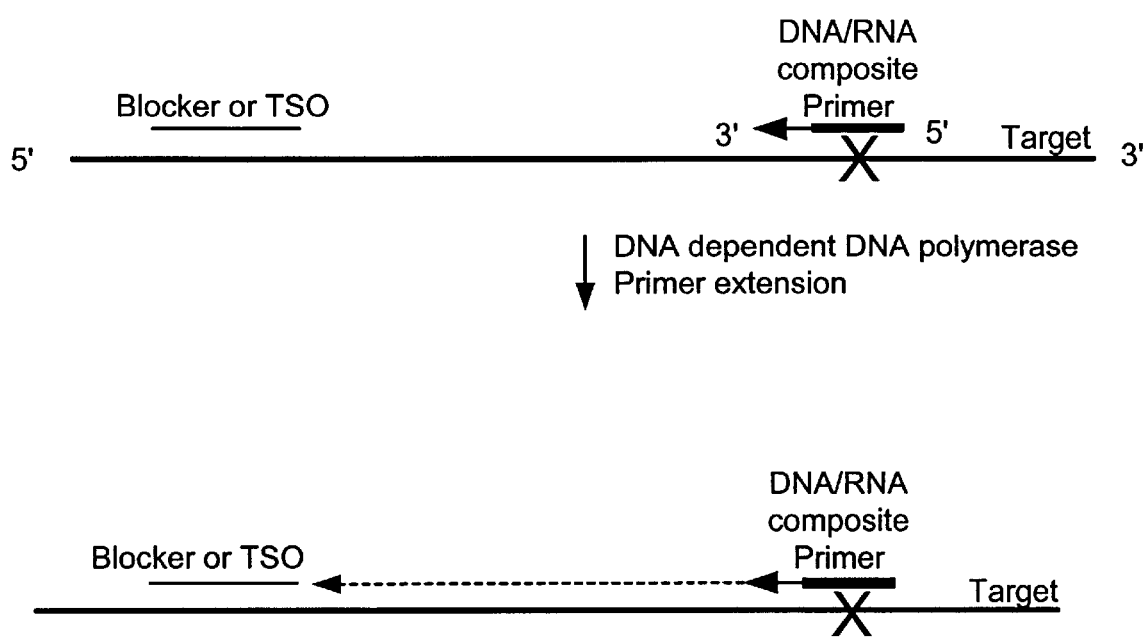
FIGS. 4A–4B is a diagrammatic representation of detection of a mutation in a template sequence using the single primer isothermal linear amplification process. "X" denotes a mutation on the target DNA at a site complementary to the RNA portion of the composite primer. As shown amplification of the target nucleic acid is blocked when a mutation is present.
Figure 4B:
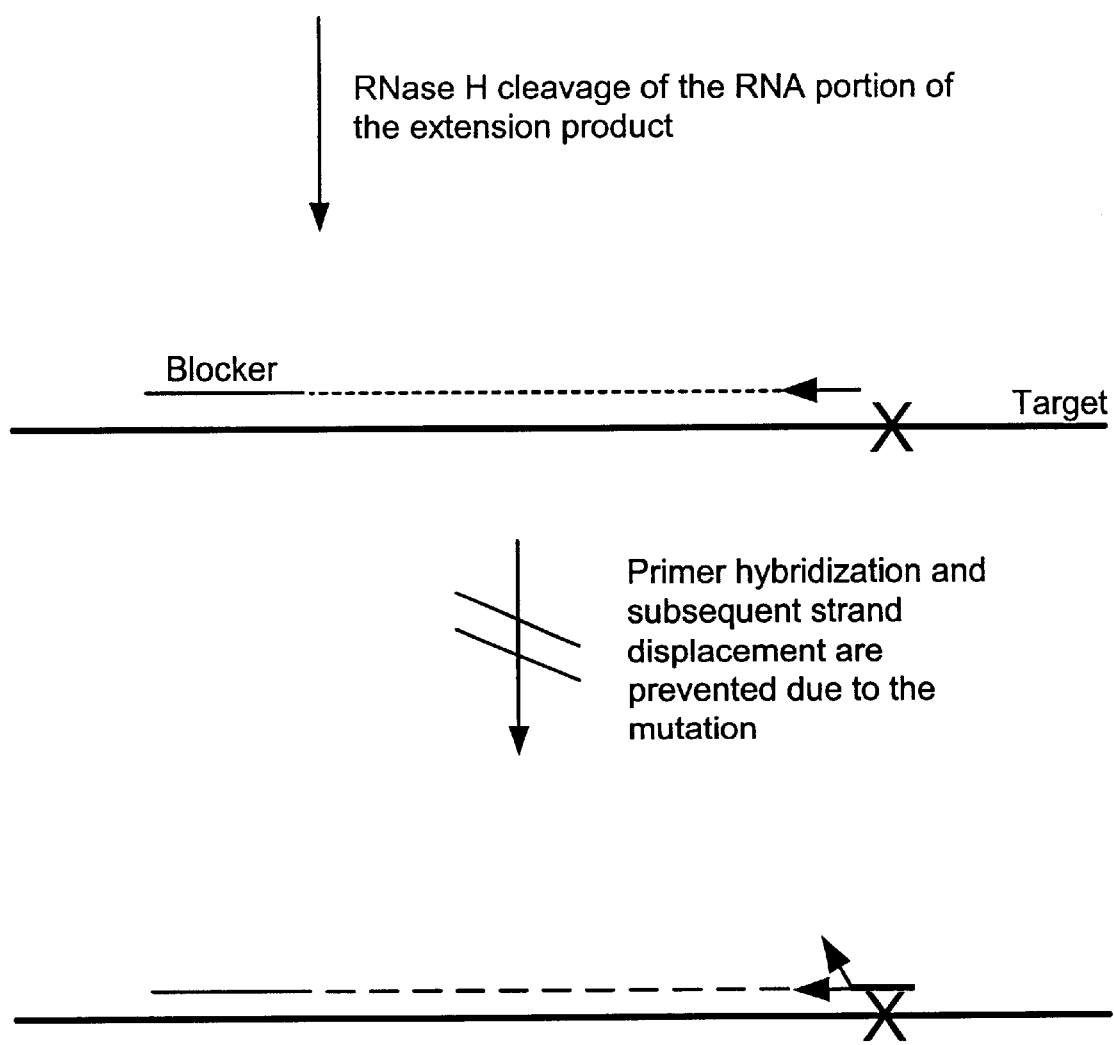

One embodiment of the method of the invention is schematically illustrated in FIG. 4. In this embodiment, the RNA portion(s) of the composite primer is designed to be complementary to the sequence of the test target nucleic acid in which the presence of a sequence alteration is suspected. Stated alternatively, the primer comprises an RNA portion(s)

that comprises a sequence that is complementary to the reference sequence (for example, a wild type sequence) against which the sequence in the test target nucleic acid is to be compared. In some embodiments, the altered sequence (i.e., the sequence comprising a sequence alteration) and the reference sequence are alleles. The sequence alteration may be a single nucleotide substitution, a deletion or insertion. The site of sequence alteration is schematically marked by X in FIG. 4.

In another embodiment, the RNA portion(s) of the composite primer is designed to be complementary to the altered sequence suspected to be present in the test target nucleic acid. Stated alternatively, the primer comprises an RNA portion(s) that comprises a sequence that is complementary to the test target nucleic, and thus is not complementary to the reference sequence (for example, a wild type sequence) against which the sequence in the test target nucleic acid is to be compared. In some embodiments, the altered sequence (i.e., the sequence comprising a sequence alteration) and the reference sequence are alleles.

The RNA portion, generally 5' RNA portion, of the composite primer comprises a sequence which is complementary to a known normal wild type sequence, or a known mutant or a polymorphic genotype. Generally, a suitable composite primer comprises an RNA portion that allows the primer to preferentially hybridize to a target nucleic acid if the target nucleic sequence comprises a sequence complementary to the RNA portion of the primer compared to if there is a mismatch (i.e., the primer has the mutated sequence and the target does not, or vice versa), wherein the target nucleic acid has a bound primer extension product and has had its 5'-RNA portion cleaved. As shown in FIG. 4, the presence of sequence alteration does not generally prevent the initial step of the amplification. The composite primer hybridizes to the target sequence, to form the first tri molecular complex, and is extended. A ribonuclease, such as RNase H, then cleaves the RNA portion of the extended primer of the complex. While it is likely that the presence of a mismatched base pair will affect the pattern of cleavage of the RNA/DNA hybrid, the cleavage is nonetheless likely to take place. The next step of binding of a composite primer to the complex by hybridization of the 5' RNA portion will be inhibited, preferably prevented, by a mismatch. This effect is dependent on factors such as the size of the hybridizing oligonucleotide and the stringency of the reaction condition. These factors are considered in the design of the composite primer, according to techniques well known and routine in the art. It is also possible that the mismatch will inhibit cleavage of the RNA portion(s) of the composite primer, thus preventing the amplification of the target sequence. Another possibility is that the mismatch will result in lower efficiency of cleavage of the RNA portion of the primer thus resulting in lower efficiency of amplification or production of less amplification product. The inability of the composite primer to hybridize to the target at this step of the amplification prevents further steps of primer extension strand displacement and production of multiple copies of the amplification products. It is understood that the detection of mutation by the methods of the present invention can be based on absence or presence of a primer extension product, or quantitative comparisons of amount of accumulated primer extension product. For example, when the composite primer comprises the reference sequence (for example, wild type), the presence of a mutation in a target strand may lead to no detectable amplification products; alternatively, it may lead to detectable products, but less than those produced from a template strand without the mutation.

When the composite primer comprises an RNA portion, generally a 5' RNA portion, that is fully complementary to a mutant genotype, amplification of a sequence which is of the normal genotype will be prevented, while a mutant genotype target will be amplified. Thus, in this case the detection and/or quantitative determination of multiple copies of the amplification product will be indicative of the presence of a target sequence of the mutant genotype. For example, parallel reactions that include either the nucleic acid sample of interest or reference sample of target nucleic with a wild type sequence could be run. Accumulation of more primer extension products in the former compared to the latter reaction would be indicative of the presence of a mutant genotype in the sample of interest. Alternatively, when the composite primer comprises a 5' RNA sequence that is fully complementary to a normal genotype sequence of the test target, amplification of a target sequence of the mutant genotype is prevented, and the detection and/or quantitative determination of amplification products is indicative of a normal genotype.

Any of the amplification methods of the present invention are suitable for detection of mutation as described above.

3'-Nucleotide-Based Isothermal Mutation Detection Utilizing the Amplification Methods of the Invention In this method, the complementarity of the 3' most nucleotide of a composite primer is used to characterize the presence or absence of a mutated sequence. Hybridization of the 3' most nucleotide of the composite primer to a target nucleic acid is required for primer extension. Therefore, product amplification indicates that the target nucleic acid contains the sequence defined by the 3' most nucleotide of the composite primer. Reduction or absence of product amplification, on the other hand, indicates that the target nucleic acid contains a sequence alteration that includes at least the base complementary to the 3' most nucleotide of the composite primer. The lack of the sequence can be due to point mutation, single nucleotide polymorphism, insertion or deletion of a sequence segment encompassing the sequence defined by the 3' most nucleotide.

In one embodiment, genotype-specific primers, designed to have the 3' most nucleotide correspond to the various sequences at the variant nucleotide position (such as due to allelism), are used for amplification according to the methods of the invention. The presence of amplification products would indicate that the target nucleic acid comprises the sequence defined by the 3' most nucleotide of the particular primer used. The absence or lack (in comparison to a reference nucleic acid having the sequence defined by the 3' most nucleotide of the particular primer used) of amplification products would indicate that the target nucleic acid does not comprise the sequence defined by the 3' most nucleotide of the particular primer used.

Mutation Detection Based on Single Stranded Conformation Polymorphism Utilizing the Amplification Methods of the Invention The DNA or RNA amplification products generated according to the methods of the present invention are also suitable for analysis for the detection of any alteration in the target nucleic acid sequence, as compared to a reference nucleic acid sequence which is identical to the target nucleic acid sequence other than the sequence alteration, as will be discussed in the following.

The products of the linear nucleic acid amplification methods (DNA) and the enhanced linear amplification methods (RNA) described previously are suitable for single stranded conformation polymorphism (SSCP or rSSCP) based mutation detection. Insofar as the RNA product of the new amplification methods is not a substrate for further amplification, sequence amplification according to the new methods does not require the presence of agents which reduce secondary structures in the single stranded product. Transcription-based amplification methods described by others are carried out in the presence of agents which reduce secondary structures, such as DMSO. Thus, it is anticipated that the enhanced linear amplification methods of the present invention can be directly linked to appropriate means for detecting single stranded conformation polymorphism, such as an electrophoretic separation method for the identification of specific mobility pattern of the single stranded RNA products for the elucidation of the presence of specific sequence features, or the presence of any difference in a test nucleic acid as compared to a reference nucleic acid.

Methods based on gel electrophoresis or capillary electrophoresis can be used for the detection and analysis of the various single stranded conformational isomers. Alternatively, it is also likely that cleavage of the single stranded DNA or RNA product using nucleases which recognize sequence dependent secondary structures, may be useful for the determination of sequence specific conformation polymorphism. Such nucleases are known in the art, such as the Cleavase assay (Third Wave). The electrophoretic methods are potentially more suitable for high throughput mutation, or genotyping, detection methods.

The determination of sequence specific electrophoretic pattern for a given nucleic acid sequence is useful for the detection of specific alleles of a test sequence. Furthermore, it is expected that an electrophoretic mobility pattern for the various alleles could be well differentiated, thus allowing the detection of two alleles in a single genomic DNA sample, as required for heterozygous genotype, or multiple alleles. Any alteration in the test nucleic acid sequence, such as base substitution, insertions or deletion, could be detected using this method. The method is expected to be useful for detection of specific single base polymorphism, SNP, and the discovery of new SNPs.

Method of Preparing Microarrays of Nucleic Acids

The single stranded nature of the products of the linear nucleic acid amplification methods (DNA) and the enhanced linear amplification methods (RNA) described previously are particularly suitable for preparing microarrays comprising the amplification products.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplified product is then contacted with a solid substrate, such as a glass slide, which is coated with an aldehyde or another reactive group which will form a covalent link with the reactive group that is on the amplified product and become covalently attached to the glass slide. Other methods, such as those using amino propryl silican surface chemistry are also known in the art, as disclosed at http://www.cmt.corning.com and http://cmgm.standord.ecu/pbrown1.

Attachment of groups to the primer which could be later converted to reactive groups is also possible using methods known in the art. Any attachment to nucleotides of the composite primer will become part of the single stranded DNA product of the linear amplifcation methods, which could then be attached to the solid surface of the microarray.

The amplification products of the methods of the present invention can be further modified, such as through cleavage into fragments or by attachment of detectable labels, prior to or following attachment to the solid substrate, as required and/or permitted by the techniques used.

Characterization of Nucleic Acids

The amplification products obtained by the methods of the invention are particularly amenable to further characterization, in part because the products are single stranded. The amplified products, either DNA or RNA, can analyzed using probe hybridization techniques known in the art, such as Southern and Northern blotting. The amplified products can also be analyzed by contacting them with microarrays comprising oligonucleotide probes. The identity of the probes provides characterization of the sequence identity of the amplified products, and thus by extrapolation the identity of the template nucleic acid present in a sample suspected of containing said template nucleic acid.

Compositions and Kits of the Invention

The invention also provides compositions and kits used in the methods described herein. The compositions may be any component(s), reaction mixture and/or intermediate described herein, as well as any combination. For example, the invention provides a composition comprising a composite primer, wherein the composite primer comprises an RNA portion and a 3' DNA portion. In another example, the invention provides a composition comprising a composite primer, wherein the composite primer comprises a 5'-RNA portion and a 3'-DNA portion. In one embodiment, the RNA portion is adjacent to the DNA portion. i another example, the invention provides a composition comprising a composite primer, wherein the composite primer comprises 5'- and 3'-DNA portions with at least one intervening RNA portion. In other examples, the invention provides a composition comprising a composite primer that is further derivatized by attachment of a moiety capable of effecting attachment of a polynucleotide comprising the composite primer to a solid substrate used in preparing nucleic acid microarrays. In some embodiments, the composite primer is further derivatized by attachment of a positively charged moiety such as an amine. In other embodiments, the invention provides a composition comprising a TSO (i.e., any of the TSO embodiments described herein, including TSOs containing one or more modifications which enhance binding to template). In some embodiments, the compositions comprise a composite primer and a termination sequence. In some embodiments, the invention provides a composition comprising a polynucleotide comprising a propromoter sequence, such as a TSO or PTO (i.e., any of those embodiments described herein), and may further comprise a composite primer and/or a blocker sequence. In some embodiments, the invention provides a composition comprising a blocker sequence (i.e., any of the embodiments described herein, including blocker sequences with modifications).

In other embodiments, the invention provides compositions comprising (a) a composite primer, wherein the composite primer comprises an RNA portion and a 3' DNA portion (in some embodiments, the RNA portion is adjacent to the DNA portion); and (b) a termination sequence. In some embodiments, the termination sequence is a TSO. In other embodiments, the termination sequence is a blocking sequence. In some embodiments, the composite primer comprises a 5'-RNA portion and a 3'-DNA portion (in certain embodiments, the RNA portion is adjacent to the DNA portion). In other embodiments, the composite primer comprises 5'- and 3'-DNA portions with at least one intervening RNA portion. In some embodiments, the composition comprises (a) a composite primer; (b) a polynucleotide comprising a termination sequence; (c) a polynucleotide comprising a propromoter sequence. In some embodiments, the propromoter sequence is provided by a PTO. In other embodiments, the propromoter sequence is provided by a TSO. Any of the above compositions may further comprise template (which comprises a target sequence) and/or any of the enzymes described herein (such as DNA polymerase, RNaseH, and/or RNA polymerase). The compositions are generally in aqueous form, preferably in a suitable buffer.

The invention also provides compositions comprising the amplification products described herein. Accordingly, the invention provides a population of DNA (anti-sense) or RNA (sense) molecules which are copies of a target sequence, which are produced by any of the methods described herein.

The compositions are generally in a suitable medium, although they can be in lyophilized form. Suitable media include, but are not limited to, aqueous media (such as pure water or buffers).

The invention provides kits for carrying out the methods of the invention. Accordingly, a variety of kits are provided in suitable packaging. The kits may be used for any one or more of the uses described herein, and, accordingly, may contain instructions for any one or more of the following uses: amplifying a nucleotide sequence; sequencing of amplified polynucleotides; and detection of sequence mutation in amplified polynucleotides.

The kits of the invention comprise one or more containers comprising any combination of the components described herein, and the following are examples of such kits. A kit may comprise any of the composite primers described herein. In some embodiments, a kit comprises two or more composite primers, which may or may not be separately packaged. In other embodiments, a kit comprises a composite primer and a termination sequence (any of those described herein). A kit may comprise a composite primer, a polynucleotide comprising a termination sequence, and a polynucleotide comprising a propromoter sequence (which may be a PTO or TSO). The composite primer may be labelled or unlabeled. Kits may also optionally include any of one or more of the enzymes described herein, as well as deoxynucleoside triphosphates and/or ribonucleoside triphosphates. Kits may also include one or more suitable buffers (as described herein). Kits useful for nucleic acid sequencing may optionally include labeled or unlabelled nucleotide analogs that upon incorporation into a primer extension product effect termination of nucleotide polymerization. One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the present invention for the intended nucleic acid amplification, and/or, as appropriate, for using the amplification products for purposes such as nucleic acid sequencing and detection of sequence mutation. The instructions included with the kit generally include information as to reagents (whether included or not in the kit) necessary for practicing the methods of the presentation invention, instructions on how to use the kit, and/or appropriate reaction conditions.

The component(s) of the kit may be packaged in any convenient, appropriate packaging. The components may be packaged separately, or in one or multiple combinations.

Where kits are provided for practicing the enhanced linear amplifications methods of the present invention, the RNA polymerase (if included) is preferably provided separately from the components used in the steps prior to the transcription steps.

The relative amounts of the various components in the kits can be varied widely to provide for concentrations of the reagents that substantially optimize the reactions that need to occur to practice the methods disclosed herein and/or to further optimize the sensitivity of any assay.

The invention also provides systems for effecting the methods described herein. These systems comprise various combinations of the components discussed above. For example, in some embodiments, the invention provides a system suitable for producing target polynucleotide sequence (or amplifying target polynucleotide sequence) comprising (a) a composite primer (any of those described herein), (b) DNA polymerase; and (c) ribonuclease. In some embodiments, the system further comprises a polynucleotide comprising a termination sequence (any of those described herein). In some embodiments, the system further comprises a polynucleotide comprising a propromoter sequence (which may be a PTO or TSO) and a DNA-dependent RNA polymerase. Any of the systems embodiments may also comprise a template (target) sequence, as described herein.

The invention also provides reaction mixtures (or compositions comprising reaction mixtures) which contain various combinations of components described herein. In some embodiments, the invention provides reaction mixtures comprising (a) a polynucleotide template; (b) a composite primer comprising a 3' DNA portion and an RNA portion; and (c) DNA polymerase. As described herein, any of the composite primers may be in the reaction mixture (or a plurality of composite primers), including a composite primer comprises a 5' RNA portion which is adjacent to the 3' DNA portion. The reaction mixture could also further comprise an enzyme which cleaves RNA from an RNA/DNA hybrid, such as RNase H. A reaction mixture of the invention can also comprise any of the polynucleotides comprising termination sequences described herein. Another example of a reaction mixture is (a) a displaced primer extension product (and, as such, contains at its 5' end sequence complementary to the 3' DNA portion of the composite primer, but not sequences complementary to the RNA portion of the composite primer); (b) a polynucleotide comprising a propromoter sequence (for example, a PTO); and (c) RNA polymerase. Other reaction mixtures are described herein and are encompassed by the invention.

The invention also includes compositions comprising any of the complexes (which are intermediates in the methods described herein) described herein. The complexes are schematically depicted in FIGS. 14. As an example, one complex of the invention is a complex comprising: (a) a template strand; and (b) a composite primer, said composite primer comprising a 3' DNA portion and an RNA portion. The composite primer may have an RNA portion which is 5' and adjacent to the 3' DNA portion. The complex may further comprise a polynucleotide comprising a termination sequence (such as a TSO or blocker sequence). The complex may also comprise a polynucleotide comprising a propromoter, such as a PTO.

The following Examples are provided to illustrate, but not limit, the invention.

EXAMPLES

Example 1

General Methods

The general methods that are described in this example are also utilized in other examples provided herein.

Buffers

Buffers that were used throughout the examples are made with the following materials.

TE Buffer: 10 mM Tris-HCl, pH 8.0, 1 mM EDTA

TBE Buffer: 89 mM Tris base, 89 mM boric acid, 2 mM EDTA, pH 8.3

FX Buffer: 20 mM Tris-SO$_4$, pH 9.0, 20 mM (NH$_4$)$_2$SO$_4$, 0.1% NP-40

Isothermal Linear Amplification Using a Single Chimera Primer, DNA Polymerase and Rnase H Sequence amplification was performed in 15 ul reactions containing 20 mM Tris-HCl, pH 8.5,6.0 mM MgCl$_2$, 1.0 mM dATP, 1.0 mM dCTP, 1.0 mM dTTP, 0.8 mM dGTP, 0.2 mM dITP (dNTP's from Amersham), 0–6% DMSO, 0–8% glycerol, 0–100 ug/ml acetylated BSA (Ambion, Austin, Tex.), 0.6 Units/ul recombinant ribonuclease inhibitor (rRNasin, Promega, Madison, Wis.), 0.5–5 uM composite primer IA005, and 100–200 nM promoter-template oligonucleotide (PTO) IA015C. Composite primer IA005 is a 20-mer primer with the sequence of: ACGGAUGCGGU-CUCCAGTGT (SEQ ID NO: 1). Promoter-template oligonucleotide (PTO) IA015C is a 55-mer oligonucleotide with the sequence of: ggAATTCTAATACgACTCACTATAgg-gAgAgCggTACgCTgATCAAAgATCCgT g-biotin (SEQ ID NO:12).

Reactions were assembled with all components except the two enzymes. After heating to 70° C. or 99° C. for 10 sec. in a programmable thermal cycler (GeneAmp 9600, Perkin Elmer), the reaction mixtures were cooled down to 55° C., 60° C. or 65° C., as described in the individual examples. Upon attaining the lower temperature, 0.05–0.24 Unit of RNase H (diluted from the 5 U/ul stock solution using a diluent/storage solution: 10 mM Tris-HCl, pH 8.5, 30% glycerol; Hybridase thermostable RNase H, Epicentre Technologies, Madison, Wis. and 1.0–5.0 Units Bca DNA polymerase (2 U/ul; Panvera, Madison, Wis.) were added. The reactions were incubated at 55° C.–65° C. for 30 minutes At the end of the incubation, reactions were cooled to 4° C. Reactions can remain at 4° C. until RNA transcription step is desired.

Enhanced Linear Amplification by RNA Transcription of the Linear Amplification ssDNA Product RNA transcription was performed at 37° C. for 3 hours in 10 ul reactions containing 2.5 ul of the linear amplification reaction mixtures above, and 40 mM Tris-HCl, pH 8.5, 70 mM KCl, 5.0 mM DTT, 12 mM MgCl$_2$, 110 ug/ml BSA, 3 mM each rNTP (ATP, UTP, CTP, GTP, Amersham), 7.5% DMSO, 1 Unit/ul rRNasin (Promega, Madison, Wis.), and 20 Units T7 RNA polymerase (Ambion, Austin, Tex.).

DNA Templates

A sequence from the J-gene region of *E. coli* K12 was chosen as a DNA template for several of the following Examples. Three DNA templates were used for these experiments: a synthetic DNA target (IA013), a primarily single-stranded DNA (351 bases) template produced by PCR amplification, and genomic DNA from the K12 strain of *E. coli* (preparation described in Example 4). Synthetic DNA target IA013 comprises:

Spacer 18

Spacer 18CGGTACGCTGATCAAAGATCCGTGCAA-CAAATGTCA

TGGTCATGGTCGTGTTGAGCGCAG-CAAAACGCTGTCCGTTAAAATCCCGG

CAGGGGTGGACACTGGAGACCGCATCCGT (SEQ ID NO:18). Spacer 18 refers to polyoxyethylene spacers. These were added to the oligo in order to retard its mobility with respect to the 100-bp ssDNA product. The sequence of the aforementioned primarily single-stranded DNA (351 bases) template produced by PCR amplification is:

<u>CGGTACGCTGATCAAAGATCCGTGCAACAAATGTC ATGGTCATGGTCGT</u> GTTGAGCGCAG-CAAAACGCTGTCCGTTAAAATCCCG-GCAGGGGTGGACA CTGGAGACCGCATCCGTCT-TGCGGGCGAAGGTGAAGCGGGCGAGCATGG CGCACCGGCAGGCGATCTGTACGTTCAG-GTTCAGGTTAAACAGCACCCGA TTTTCGAGCGT-GAAGGCAACAACCTGTATTGCGAAGTC-CCGATCAACTTC GCTATGGCGGCCGCTGGGTGGCGAAATC-GAAGTACCGACCCTTGATGGTCG CGTCAAACT-GAAAGTGCCTGGCGAAACCC AGACCGGTAAGCTATTCCGTATGCG (SEQ ID NO:17) wherein the PCR primers are bolded and underlined and the composite primers are bolded, with RNA portion in italics.

Preparation of ssDNA Target from PCR Amplification Product

Single-stranded DNA template for isothermal linear amplification was prepared by PCR amplification of a 351-bp segment of the *E. coli* J gene using the primers IA006 and IA004. Primer IA006 is a 23-mer with the sequence of: CGGTACGCTGATCAAAGATCCGT (SEQ ID NO:16). Primer IA004 is a 26-mer with the sequence of: CGCAT-ACGGAATAGCTTACCGGTCT (SEQ ID NO:15).

PCR was performed in 100 ul reactions containing 20 mM Tris-SO$_4$, pH 9.0, 20 mM (NH$_4$)$_2$SO$_4$, 0.1% NP-40, 2.0 mM MgCl$_2$, 300 uM each dNTP (dATP, dTTP, dCTP, dGTP), 5 Units Taq DNA polymerase, 400 nM primer IA006, 400 nM 5'-phosphate-primer IA004, and 0.2 ul of a crude lysate of *E. coli* K12 strain. A modified "touchdown PCR" protocol was used with the following parameters: 95° C. for 5 seconds, 68° C. for 1 minute for 5 cycles; 94° C. for 5 seconds, 60° C. for 30 seconds, 72° C. for 1 minute for 5 cycles; 94° C. for 5 seconds, 55° C. for 30 seconds, 72° C. for 1 minute for 40 cycles; 72° C. for 15 minutes and then held indefinitely at 4° C. Primer IA004 was synthesized with a 5'-phosphate to protect the sense-strand from digestion by lambda exonuclease (Strandase kit, Novagen, Madison, Wis.). The Strandase digestion was performed according to the manufacturer's recommendation. Briefly, PCR product prepared as described above, was precipitated from the reaction mixture by the addition of 1/10 volume 3M sodium acetate, pH 5.2 and 0.6 volumes isopropanol, cooling to −20° C. for 1 hour, and centrifuged at maximum speed in a microcentrifuge for 30 minutes. The DNA pellet was washed once with 75% ethanol, then air-dried briefly before resuspension in 80 ul water. Concentration was estimated from O.D. at 260 nm, and 60 Units of lambda exonuclease (Strandase, Novagen) was added. Digestion was allowed to proceed at 37° C. for 20 minutes, reactions were then heated to 75° C. for 10 minutes, and cooled to 4° C. Incubations were performed in a programmable thermal cycler (GeneAmp 9600, Perkin Elmer). Remaining DNA was purified using QiaQuick Nucleotide Removal Columns (Qiagen, Valencia, Calif.) following the manufacturer's recommended procedure and using the buffers provided with the kit (Qiagen, Valencia Calif.). Briefly, 10 volumes of Buffer PN (Qiagen) were added to the sample. The entire volume was then applied to a Qiagen spin column and centrifuged (6000 rpm 1 minute in a microcentrifuge). The filtrate was discarded, and the column was washed twice with 500 ul of Buffer PE (Qiagen). The column was then dried thoroughly by centrifugation at maximum speed for 3 minutes. The DNA was eluted in 50 ul Buffer EB (10 mM Tris-HCl, pH 8.5 )(Qiagen). The concentration was estimated to be about $2.5 \times 10^{12}$ copies/5ul from OD at 260 nm. Gel analysis revealed that significant dsDNA (less than half the total) remained, but the error in concentration was less than 2-fold. The DNA was diluted to $10^{10}$ copies/5ul in TE Buffer. Serial dilutions were prepared from the $10^{10}$ copy stock solution as needed. Concentration based on O.D. measurement was confirmed by limiting dilution PCR analysis.

Gel Electrophoresis

Amplification products were electrophoretically separated on Novex pre-cast 4–20% polyacrylamide gradient gels (Invitrogen, Carlsbad, Calif.; part no. EC62255) in 1×TBE Buffer (89 mM Tris base, 89 mM boric acid, 2 mM EDTA, pH 8.3) in a Novex electrophoresis apparatus (EI9001-XCell II Mini Cell, Novex). Reaction mixtures (5 ul) from linear amplification or transcription (enhanced linear amplification) were mixed with 1 ul of 6×Gel Loading Solution (40% sucrose, 0.25% bromophenol blue, 0.25% xylene cyanole), and the entire sample was immediately loaded into each well. Gels were subjected to 250V for approximately 5 minutes, until all samples. had entered the gel, and the voltage was lowered to 175V for 45 minutes. Gels were removed from between the plastic plates and stained in 0.5 ug/ml ethidium bromide in IX TBE Buffer (89 mM Tris base, 89 mM boric acid, 2 mM EDTA, pH 8.3). A dsDNA molecular size marker (Hi-Lo DNA Marker, Bionexus, San Leandro, Calif.) was included in one lane of each gel run. This marker contains 16 fragments of the following sizes: 50, 100, 200, 300, 400, 500, 750, 1000, 1400, 1550,2000, 3000,4000,6000, 8000, and 10000 bp. Typically, 50–2000 bp could be resolved on the gels used.

Hybridization

Oligonucleotide probes for hybridization examples (IA010 for ssDNA products; IA014 for ssRNA products) were 5'-end-labelled using T4 polynucleotide kinase (New England Biolabs, Beverly, Mass.) and $\gamma$-$^{32}$P-ATP (adenosine 5'[$\gamma$-$^{32}$P] triphosphate, triethylammonium salt, Amersham, Piscataway, N.J.; PB10218, >5000 Ci/mmol, 10 mCi/ml). Primer IA010 is a 21-mer with the sequence of: ATGT-CATGGTCATGGTCGTGT (SEQ ID NO:13). Primer IA014 is a 31-mer with the sequence of: CTCAACACGAC-CATGACCATGACATTTGTTG (SEQ ID NO:14). Labelling reactions (50 ul total volume) contained 70 mM Tris-HCl, pH 7.6, 10 MM MgCl$_2$, 5 mM DTT, 1 ug oligo (147 pmol for primer IA010; 101 pmol for primer IA014), 250 uCi $\gamma$-$^{32}$P-ATP, and 30 Units T4 polynucleotide kinase. Incubation was at 37° C. for 30 minutes, followed by removal of unincorporated nucleotide using QIAquick Nucleotide Removal Kit (Qiagen, Valencia, Calif.). The decay rate (cpm) was determined in a Packard Minaxi Tri-Carb 4000 Series liquid scintillation counter by Cherenkov counting of 1 ul of the labelled oligo.

Hybridization was performed in 30 ul reactions. Product DNA (or RNA) (10 ul) was added to 20 ul of probe mix. Reactions contained 100 mM NaCl and 106 cpm of probe (correcting for decay using a half-life of 14.3 days). After heating to 65° C. 15 seconds, hybridization was allowed to proceed at 42° C. for 30 minutes, followed by cooling to 4° C. These steps were performed in a programmable thermal cycler with a heated cover (GeneAmp 9600, Perkin Elmer). The entire volume of hybridization reaction was electrophoresed in 10% polyacrylamide gels in 1×TBE Buffer (89 mM Tris base, 89 mM boric acid, 2 mM EDTA, pH 8.3) at 150V for 3 hours. Gels were removed from the glass plates, wrapped in plastic wrap, and exposed to autoradiography film (BioMax MR, Kodak) at −20° C. overnight (~16 hours) with two intensifying screens.

Example 2

Isothermal Linear Amplification

Isothermal linear amplification using a single composite primer, DNA polymerase, RNase H, and TSO or blocker was performed. Reaction mixtures containing all reaction components, as described above, as well as reaction mixtures without one of the key reagents such as composite primer, RNase H, or Bca DNA polymerase (Panvera, Madison, Wis.) were spiked with $10^{10}$ copies of synthetic ssDNA target (IA010—sequence listed in Example 1). A negative control reaction containing all the reagents and no target ssDNA, was also included. The isothermal linear amplification of target DNA sequence was carried out as described above. Target denaturation was carried out at 70° C. and the isothermal amplification was carried out at 65° C.

Figure 5:
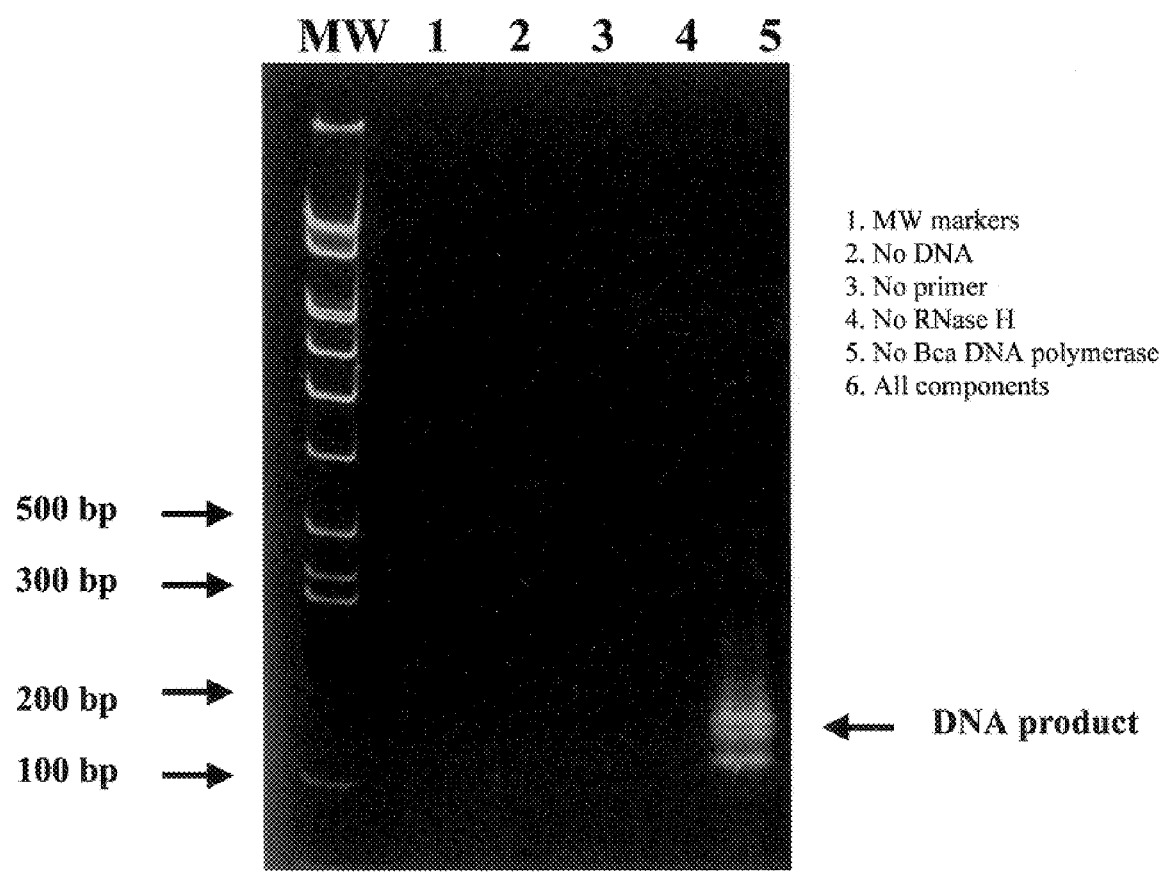
FIG. 5 depicts an ethidium bromide stained PAGE gel of linear isothermal amplification products of a synthetic DNA target.

The amplification products were resolved by gel electrophoresis (FIG. 5) (First lane: molecular weight ladder; lanes #1–4: no DNA, no primer, no RNase H, no Bca DNA polymerase, respectively; lane 5: contains all components). No amplification products were detected in reaction mixtures without primer, RNase H or Bca DNA polymerase.

Figure 6:
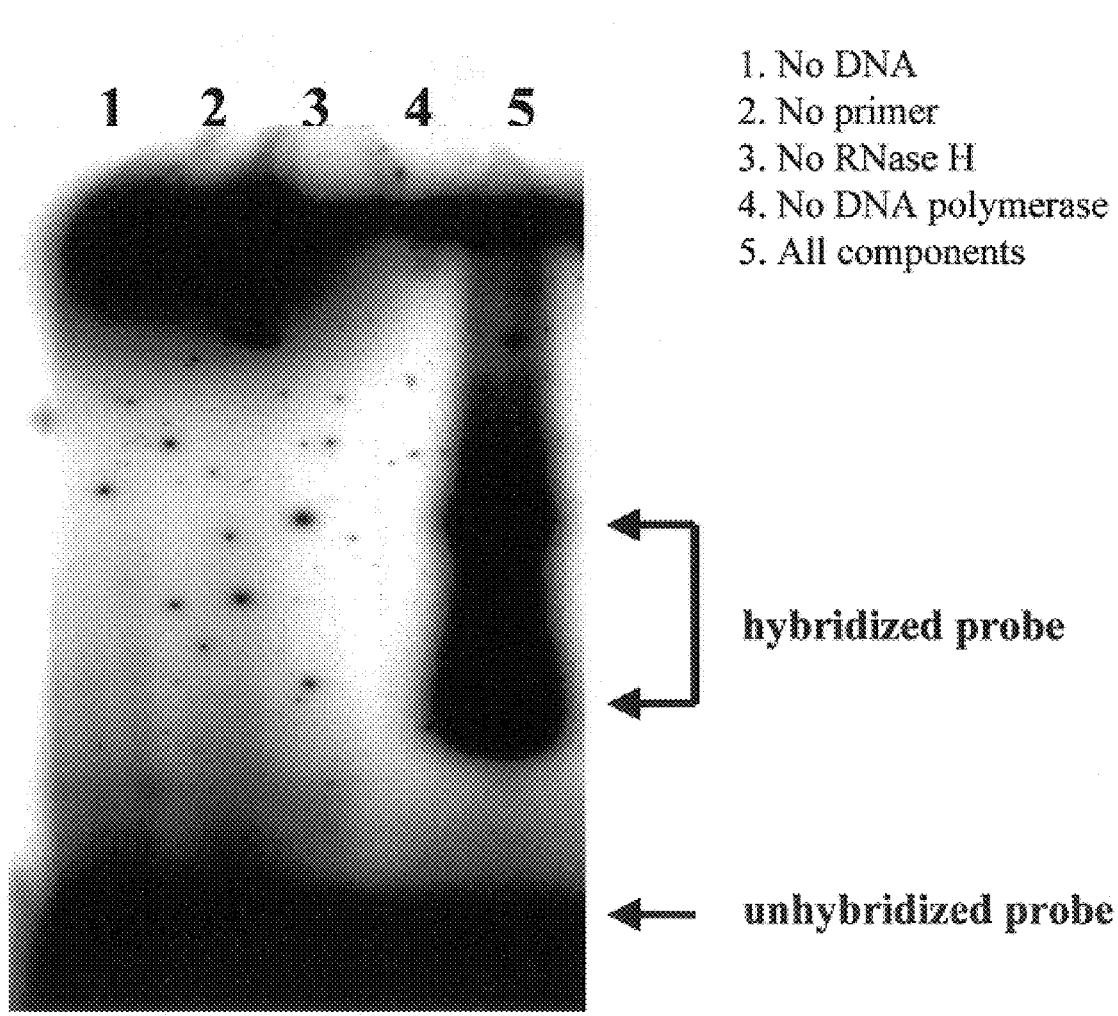
FIG. 6 depicts an autoradiogram of PAGE analysis of hybridization of DNA amplification products to a specific probe.

Probe IA010 hybridization and autoradiography to the ssDNA product of the linear amplification method, as shown in FIG. 6 (Lanes 1–4: no DNA, no primer, no RNase H, no DNA polymerase, respectively; lane 5: contains all components), verified the identity of the amplification product. The linear amplification of the synthetic oligonucleotide target in this experiment was done using a non blocked promoter-template oligonucleotide (IA015b). Promoter-template oligonucleotide IA015b is a 55-mer with a sequence of:

GGAATTCTAATACGACTCACTATAGG-GAGAGCGGTACGCTGATCAAAGAT CCGTG (SEQ ID NO:11). The amplification reaction standard reaction components used for this amplification reaction are as given above. The initial denaturation step was performed at 70° C. for 10 seconds. The reactions were cooled down to 65° C., and further incubated at this temperature for 30 minutes following the addition of Bca polymerase and RNase H. No hybridization was detected in the control reactions (no DNA, no primer, no RNase H, no Bca).

Example 3

Promoter-Template Oligonucleotide Coupled Isothermal Linear Amplification and Transcription The promoter-template oligonucleotide (PTO) contains two essential sequence motifs: a T7 promoter sequence (5'-TAATACGACTCACTATAGGGAgGAG (SEQ ID NO:20)) and a sequence complementary to the ssDNA template. Four versions of a PTO were designed (IA012, IA012b, IA015, IA015b). IA012 PTO is a 67-mer and has a sequence of:

GGAATTC<u>TAATACGACTCACTATAGGGAGAG</u>ATCGAGTAGC-TC <u>CGGTACGCTGATCAAAGATCCGTG (SEQ ID NO: 8).</u> IA012 PTO contains two sequences in addition to the core T7 promoter: a 5'-extension (5'-GGAATTC (SEQ ID NO:21)) and a spacer (5'-ATCGAGTAGCTC (SEQ ID NO:22)) between the promoter and the target DNA-complementary sequence. IA015 is the shorter PTO (48-mer), lacking both the 5'-extension and the spacer. IA015 PTO has the sequence of:

TAATACGACTCACTATAGGGAGAGCGG-TACGCTGATCAAAGATCCGTG (SEQ ID NO:10). IA012b PTO is a 60-mer which contains the spacer, but not the extension. IA012b PTO has the sequence: TAATACGACTCACTATAGGGAGAGATC-GAGTAGCTCCGGTACGCTGATCA AAGATCCGTG (SEQ ID NO:9). IA015b contains the extension, but not the spacer. The sequence of IA015b is disclosed in Example 2. All primers other than the chimeric oligonucleotides IA005, IA019, and IA020 were synthesized by Keystone (Division of BioSource International, Camarillo, Calif.) and were PAGE purified.

A general schematic for this amplification method is illustrated in FIGS. 2A–C. The ability of IA012, IA012b, IA015, and IA015b to convert the ssDNA template into a substrate for T7 RNA polymerase was assessed by comparing the amount of RNA produced after transcription of overlap-extension products formed between a synthetic oligo product (IA009) and each of the PTO's. Synthetic oligo product IA009 is a I 00-mer with the sequence of: AGTGTCCACCCCTGCCGGGATTTTAACGGACAGCG TTTTGCTGCGCTCAACACGACCATGAC-CATGACATTTGTTGCACGGATCTT TGATCAGCG-TACCG (SEQ ID NO:19). Overlap-extension was performed in 15 ul reactions containing 20 mM Tris-HCl, pH 8.5, 6 mM MgCl$_2$, I mM each dNTP (dATP, dTTP, dCTP, dGTP), 100 nM IA009, 100 nM PTO, and 1 Unit Bca DNA polymerase. Reactions were constituted without Bca DNA polymerase, heated to 95° C. then cooled over 10 minutes to 60° C. After addition of DNA polymerase, reactions were incubated at 60° C. for 30 minutes. A portion (2.5 ul) of the reaction mixture was added to the standard RNA transcription reaction mixture and the transcription reactions were assessed by gel electrophoresis.

Figure 7:
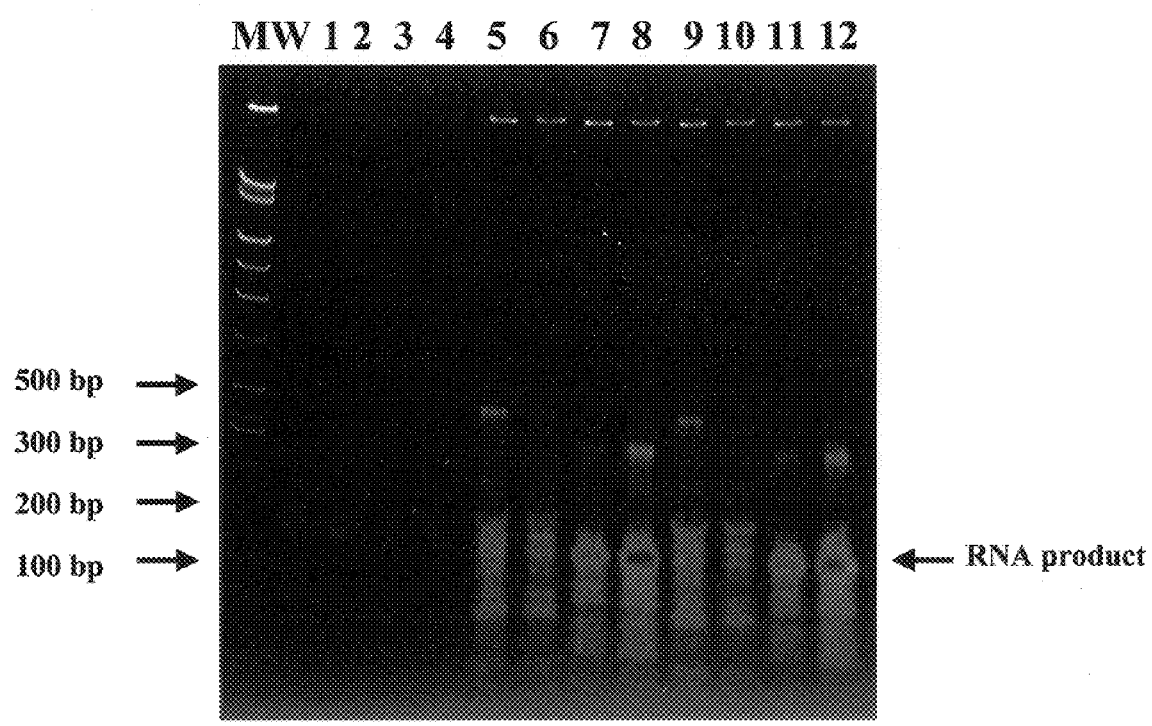
FIG. 7 depicts an ethidium bromide stained PAGE gel comparing the efficiency of ssRNA transcription products generated from overlap extension.
Figure 8:
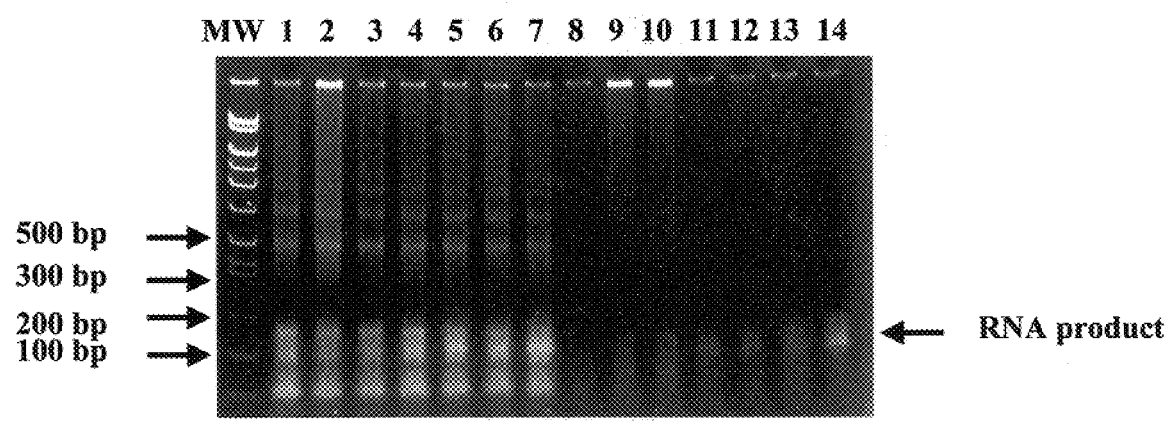
FIG. 8 depicts an ethidium bromide stained PAGE gel comparison of isothermal linear amplification with and without a 3'-blocked PTO.

As shown in FIG. 7 (Lane 1: molecular weight ladder; lanes 2–5: overlap extension product from IA012, IA012b, IA015, IA015b, respectively; lanes 6–13: RNA from IA012, IA012b, IA015, IA015b, IA012, IA012b, IA015, IA015b, respectively) significantly more RNA was produced by the transcription substrate produced with the shorter PTO's (IA015, IA015b) than by either of IA012 or IA012b. The PTO containing the 5'-extension but not the spacer (IA015b) produced demonstrably higher yields of RNA. In all cases, however, multiple products appeared in addition to the major RNA band. A fifth PTO was designed having the same sequence as IA015b, but with a 3'-blocking group (biotin) to eliminated the free 3'-OH, to demonstrate the improved performance of a 3'-blocked PTO. Blocking the free 3'-OH of the PTO eliminates its ability to initiate non-specific incorporation of a functional promoter sequence to the amplifiction products leading to non-specific generation of transcription products. The performance of 3-blocked and unblocked PTO in the enhanced isothermal linear amplification was assessed from amplification of a synthetic oligonucleotide target, using the standard conditions. The 3'-blocked PTO (IA015c) produced comparable yields of specific RNA as IA015b, but with significantly less background, as shown in FIG. 8 (Lane 1: molecular weight ladder; lanes 2, 9: no DNA, 30 minutes; lanes 3, 10: no DNA, 1 h; lanes 4, 11: no DNA, 2h; lanes 5, 12: $10^{10}$ copies IA013, 30 min; lanes 6, 13: $10^{10}$ copies IA013, 1h; lanes 7, 14: $10^{10}$ copies IA013, 2h; lanes 8, 15: $10^{11}$ copies IA013, 30 min; reactions 1-7 were not blocked (IA015b), reactions 8–15 were blocked (IA015c)). Negative control reactions (no DNA template) and reactions containing $10^{10}$ copies of oligo target (IA013) were amplified by strand displacement for 30 minutes, 1 hour, or 2 hours at 55 C, with either IA015b or IA015c included in the strand-displacement reaction. When the 3'-OH was not blocked, non-specific RNA was produced in all reactions and obscured identification of the specific RNA band. In contrast, the blocked PTO produced primarily a single RNA product.

Example 4

Amplification of a J Gene Sequence of *E. coli* Genomic DNA by the Isothermal Enhanced Linear Amplification DNA was isolated from 25 ml of *E. coli* K12 (ATCC 10798) grown overnight in Tryptone-NaCl medium. Genomic DNA was isolated by lysozyme digestion and solubilization in a chaotropic lysis solution (Bactozol Kit, Molecular Research Center, Cincinnati, Ohio) following the manufacturer's recommended procedure. Briefly, bacteria were collected by centrifugation at 6000×g for 5 minutes. Cell pellets were resuspended in Bactozyme digestion buffer and incubated at 50° C. for 30 minutes. The resulting lysate was clear at the end of the digestion, without any visible clumps of undigested cells. The lysate was mixed with 4 volumes of DNazol reagent (Molecular Research Center, Cincinnati, OH) and incubated for 15 minutes at room temperature. DNA was precipitated from the solution by addition of 0.6 volume ice-cold ethanol. After incubation for 5 minutes at room temperature, the precipitated DNA was collected by centrifugation for 5 minutes at maximum speed in a micro-centrifuge. The DNA pellet was washed with 75% ethanol, centrifuged again, and resuspended in 1.5 ml TE Buffer (10 mM Tris-HCl, pH 8.0, 1 mM EDTA) by heating at 50°–55° C. for 30 minutes, with frequent agitation. The resulting solution was passed repeatedly through a 22 gauge syringe needle to shear the DNA and reduce the viscosity of the solution. DNA was precipitated again (EPI005-35) by the addition of $\frac{1}{10}$ volume of 5M ammonium acetate and 3 volumes ice-cold ethanol. After incubation at −20° C. for 1 hr, the DNA was collected by centrifugation at maximum speed in a micro-centrifuge. The pellet was washed with 75% ethanol, centrifuged again, and resuspended in 150 ul TE Buffer. Two dilutions in TE Buffer were prepared for O.D. measurement (Beckman DU640 spectrophotometer), from which DNA concentration was calculated by assuming 50 ug/ml dsDNA produces an O.D. at 260 nm of 1. DNA concentrations of the two dilutions were 24.2 ug/10 ul and 24.6 ug/10 ul. The average of these two measurements (24.4 ug/10 ul) corresponds to approximately $2.5 \times 10^9$ genome copies/5 ul (5 fg of *E. coli* genomic DNA=1 copy).

Isothermal Enhanced Linear Amplification

DNA was serially diluted in TE Buffer to $10^9$, $10^8$, or $10^7$ copies/5 ul, and denatured by heating to 95° C. for 5 minutes followed by rapid cooling on ice. Single-stranded template DNA also was diluted to $10^9$ copies/5 ul. Reactions were assembled to contain no DNA, $10^7$, $10^8$, $10^9$, or $2.5 \times 10^9$ copies of genomic DNA.

Amplification was performed in 15 ul reactions containing 20 mM Tris-HCl, pH 8.5, 6.0 mM MgCl$_2$, 1.0 mM dATP, 1.0 mM dCTP, 1.0 mM dTTP, 0.8 mM dGTP, 0.2 mM dITP (dNTP's from Amersham), 6% DMSO, 8% glycerol, 100 ug/ml acetylated BSA (Ambion, Austin, Tex.), 0.6 Units/ul recombinant ribonuclease inhibitor (rRNasin, Promega, Madison, Wis.), 5 uM composite primer IA005 (sequence disclosed in Example 1), 200 nM promoter-template oligonucleotide (PTO) IA015C (sequence disclosed in Example 1). Reactions were assembled with all components except the two enzymes. After heating to 99° C. for 10 seconds in a programmable thermal cycler (GeneAmp 9600, Perkin Elmer), reactions were incubated at 60° C. for 30 minutes Upon attaining 60° C., 0.6 ul of RNase H (0.05 Units diluted from the 5 U/ul stock solution in 10 mM Tris-HCl, pH 8.5, 30% glycerol), Hybridase, Epicentre Technologies, Madison, Wis.) and 1.0 ul Bca DNA polymerase (2.0 Units, Panvera, Madison, Wis.) were added. At the end of the 60° C. incubation, reactions were cooled to 4° C. A volume of 5.0 ul of strand-displacement product was added to each RNA transcription reaction (total volume 20 ul). RNA transcription was performed using the standard conditions and scaling up the reaction volume to 20 ul to provide sufficient material for direct gel analysis (5 ul) and probe hybridization (10 ul).

Unlike the amplification of defined single stranded synthetic target, the amplification of genomic DNA according to the method of the invention requires the formation of a defined stop for the formation of a ssDNA product with a defined 3'-end. The formation of a defined stop for primer extension can be achieved by a blocker, which hybridizes to defined site on the target strand and can not be displaced by the polymerase. Alternatively, as in the present example, a GC rich sequence up stream of the primer site, provided a stop point for primer extension, thus leading to the formation of a ssDNA product with defined 3-end.

Figure 9:
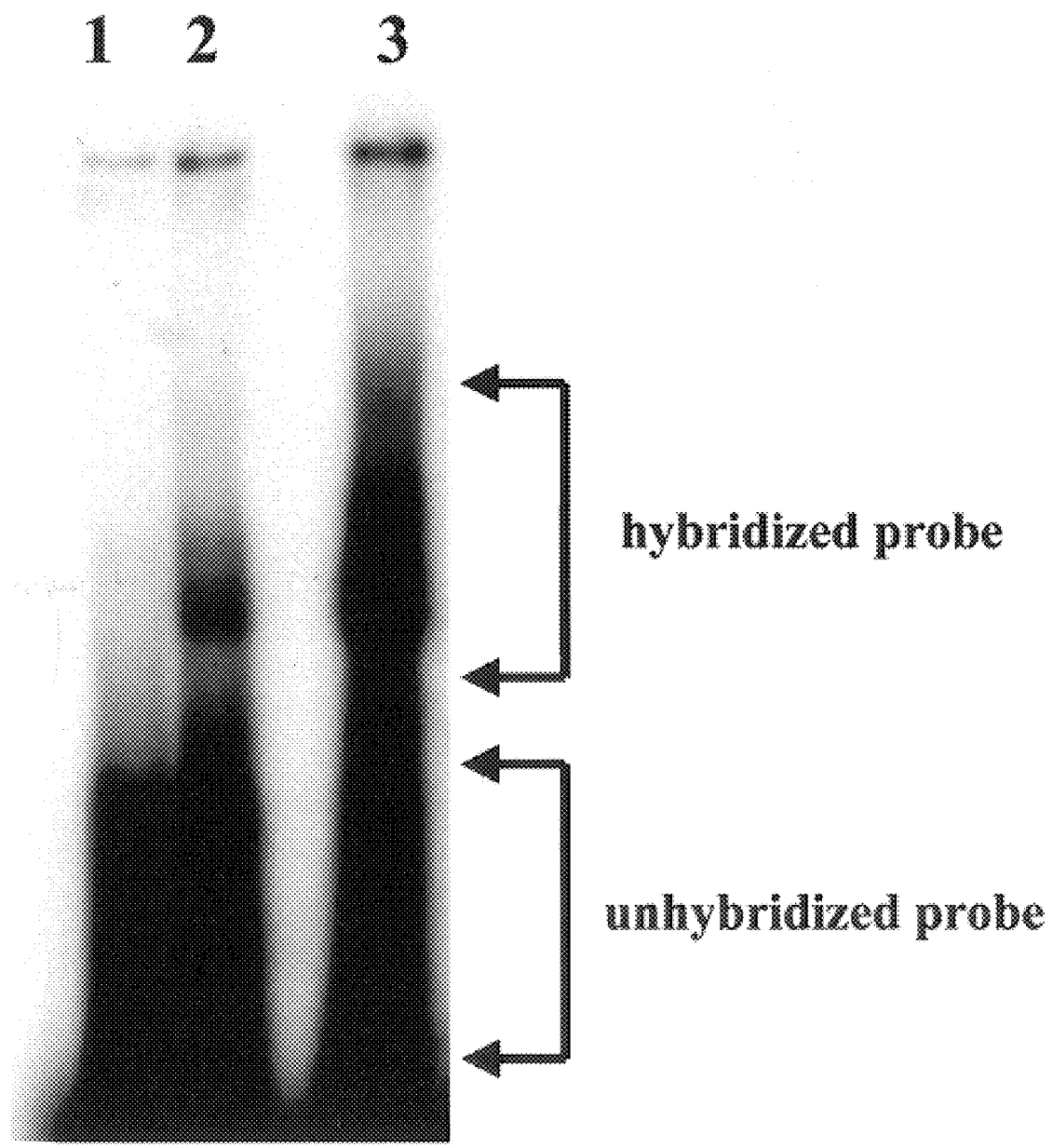
FIG. 9 depicts an autoradiogram of probe hybridized to amplification products generated by isothermal linear amplification of a J gene sequence from *E. coli* genomic DNA.

Successful amplification of a defined sequence of genomic DNA by the enhanced isothermal linear amplification method of the invention is shown in FIG. 9 (Lane 1: no DNA; lane 2: $10^7$ copies *E. coli* genomic DNA; lane 3: empty; lane 4: $10^8$ copies *E. coli* genomic DNA). The ssRNA product is shown to hybridize to a specific oligonucleotide probe.

Example 5
Evaluation of the Effect of Primer Design on the Performance of Enhanced Isothermal Linear Amplification The performance of each of the three composite primers in the amplification methods of the invention was assessed. The isothermal linear amplification was performed in 15 ul reactions containing 20 mM Tris-HCl, pH 8.5, 6.0 mM $MgCl_2$, 1.0 mM dATP, 1.0 mM dCTP, 1.0 mM dTTP, 0.8 mM dGTP, 0.2 mM dITP (dNTP's from Amersham), 6% DMSO, 8% glycerol, 100 ug/ml acetylated BSA (Ambion, Austin, Tex.), 0.6 Units/ul recombinant ribonuclease inhibitor (rRNasin, Promega, Madison, Wis.), 5 uM composite primer, 200 nM promoter-template oligonucleotide (PTO) IA015C. The sequence of PTO IA015C is disclosed in Example 1. The sequence of composite primers IA005 (20-mer) is disclosed in Example 1. Other composite primer sequences with alphanumerical names are as follows:

IA019 (20-mer) ACGGAUGCGGUCUCCAGTGT (SEQ ID NO:2)
IA020 (21-mer) GACGGAUGCGGUCUCCAGTGT (SEQ ID NO:3)

Four other composite primer sequence were used that did not have alphanumerical names. Their sequences are, respectively:

(1) GCAAGACGGAUGCGGUCUCCAGTGT (SEQ ID NO:4)
(2) GACGATGCGUCTCCAGTGT (SEQ ID NO:5)
(3) GACGGATGCGGUCTCCAGUGT (SEQ ID NO:6)
(4) GACGGATGCGGUCTCCAGUGUCCA (SEQ ID NO:7)

These composite primers were synthesized by Dharmacon Research, Inc. (Boulder, Colo.). The RNA portion of the oligonucleotide was synthesized using a 5'-silyl protecting group in conjunction with an acid-labile 2'-orthoester protecting group (2'-bis(acetoxyethoxy)-methyl ether or "2'-ACE" (Scaringe, S. A., et al. *J. Am. Chem. Soc.* 120:11820–11821 (1998) and Scaringe, S. A. Advanced 5'-silyl-2'-orthoester approach to RNA oligonucleotide synthesis. Methods in Enzymology (in press)). Primers were PAGE purified.

Reactions were assembled with all components except the two enzymes. After heating to 70° C. for 10 seconds in a programmable thermal cycler (GeneAmp 9600, Perkin Elmer), reactions were cooled to 55° C.–65° C. Upon attaining the lower temperature, 0.05 Unit of RNase H (diluted from the 5 U/ul stock solution using a diluent/ storage solution: 10 mM Tris-HCl, pH 8.5, 30% glycerol; Hybridase thermostable RNase H, Epicentre Technologies, Madison, Wis.) and 2.0 Units Bca DNA polymerase (2 U/ul; Panvera, Madison, Wis.) were added. The reactions were incubated at 55° C–65° C. for 30 minutes. At the end of the incubation, reactions were cooled to 4° C. until RNA transcription. RNA transcription was performed at 37° C. for 3 hours in 10 ul reactions containing 2.5 ul of linear amplification reaction above, and 40 mM Tris-HCl, pH 8.5, 70 mM KCl, 5.0 mM DTT, 12 mM $MgCl_2$, 110 ug/ml BSA, 3 mM each rNTP (ATP, UTP, CTP, GTP, Amersham), 7.5% DMSO, 1 Unit/ul rRNasin (Promega, Madison, Wis.), and 20 Units T7 RNA polymerase (Novagen, Madison, Wis.).

Figure 10:
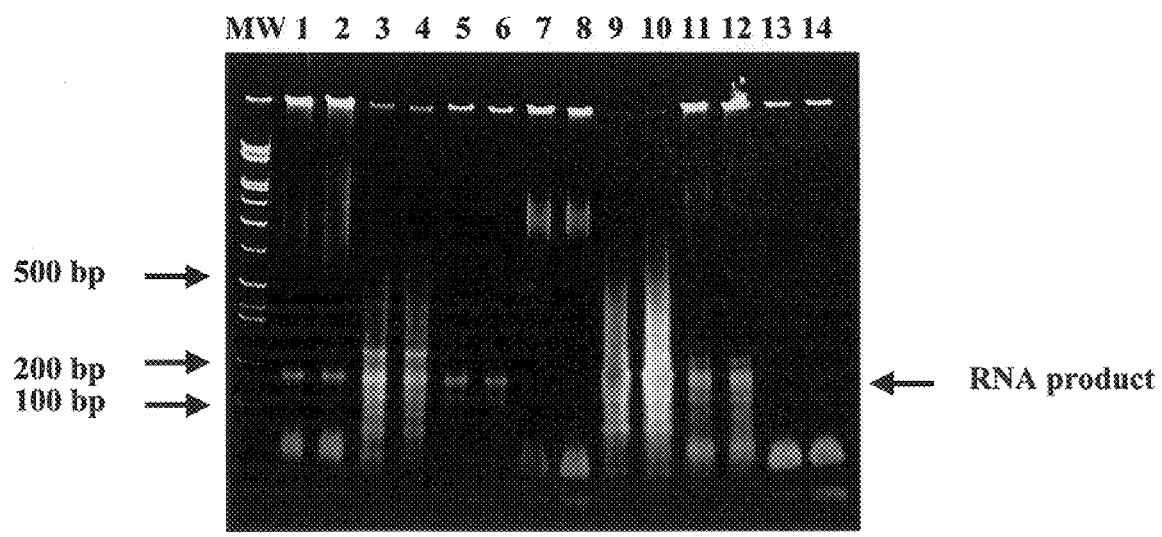
FIG. 10 depicts an ethidium bromide stained PAGE gel of linear isothermal amplification RNA products generated using three different designs of the composite primer.

The products of the enhanced linear amplification generated with each of the composite primers were resolved by gel electrophoresis as shown in FIG. 10 (Lane 1: molecular weight ladder; lanes 1,2: IA015, 60° C.; lanes 3,4: IA019, 55° C.; lanes 5,6: IA019, 60° C.; lanes 7,8: IA019, 65° C.; lanes 9,10: IA020, 55° C.; lanes 11, 12: IA020, 60° C.; lanes 13,14: IA020, 65° C.). The composite primers were designed to hybridize at the same site on the target strand, and differed by the number of deoxynucleotides at the 3'-end. The highest yield of RNA product was produced with primer IA020, followed by IA005 and IA019 equally. The other four composite primers yielded less RNA products. The optimal temperature for the isothermal linear amplification step was different for the different primers, as expected.

Example 6
Isothermal Sequencing of Nucleic Acid Targets Using the Linear Amplification Methods Nucleic acid sequences to be analyzed are first isolated from their sources. Non-limiting examples of sources used in this example are animal, plant, bacteria, viruses, yeast, or fungi. If the source of nucleic acids (DNA or RNA) is from animal tissues, then the tissue is homogenized or sonicated or subjected to some force that enables single cells to become separated from the connective tissue. Caution is exercised to prevent degradation of DNA and RNA, especially mRNA, and, to prevent shearing of genomic DNA during the handling of the tissue. Animal cells can also be obtained from commercial sources, i.e. Gibco BRL, or from non-profit sources, i.e. American Tissue Type Culture (ATCC). Depending on the form of nucleic acid desired, genomic DNA, total RNA, or mRNA can be isolated by following standard protocols found in Sambrook et al. supra. Protocols for isolating nucleic acid from plant cells can also be found in Current Protocols in Molecular Biology supra. If the source of nucleic acid is from non-mammalian sources, for example, bacteria, yeast, fungi, or viruses, slightly different protocols are used to isolate nucleic acid. These protocols can be found in Sambrook et al. or Current Protocols in Molecular Biology for bacteria, yeast, fungi, and viruses.

Amplification of the defined target nucleic acid sequence is carried out as described for isothermal linear amplification, as described herein. About $10^2$ to $10^{12}$ copies is used for template. In addition to the natural deoxyribonucleotide triphosphates (dNTPs) that are used for the amplification method, the sequencing reaction mixture includes the labeled triphosphate analogs. If each analog is uniquely labeled, all four can be added in the same reaction tube. Otherwise, if each nucleotide analog is labeled with the same label, the sequencing reactions are carried in four different reaction tubes in which each reaction mixture contains one of the nucleotide analogs. These analogs are incorporated to the primer extension product by the polymerase and serve to stop further extension along the target sequence. The resulting truncated extension products are labeled. The accumulated multiple displaced primer extension products vary in length, according to the site of incorporation of each of the analogs, which represent the various sequence locations of a complementary nucleotide on the target sequence. Analysis of the reaction products for elucidation of sequence information can be carried out by running the products on a gel. Alternatively, other methods of anlysis can be used as well. As with other sequencing methods, the sequencing reactions are carried out either in a single reaction vessel, or in separate reaction vessels. The choice of method to be used is dependent on the nucleotide triphosphate analogs used. Thus when each of the analogs is differentially labeled, the sequencing reaction can be carried out in a single vessel. The considerations for choice of reagent and reaction conditions for optimal performance of sequencing analysis according to the method of the invention are similar to those for other previously described methods.

The plurality of primer extension products which differ in size in accordance with the specific incorporation of elongation terminator, are size separated using any of a variety of methods known in the art. The profile of the plurality of primer extension products produced with each of the terminator analog is indicative of the nucleotide sequence of the test nucleic acid sequence.

Example 7
Sequencing of Nucleic Acid Targets Using Enhanced Amplification

Amplification of the defined target nucleic acid sequence is carried out as described for isothermal linear amplification, which involves transcription, as described herein. Either use of TSO's or PTO's may be used to append the protopromoter sequence to the product of the isothermal linear amplification. In addition to the natural ribonucleotide triphosphates (rRTPs) that are used for the enhanced linear amplification method according to the present invention, the sequencing reaction mixture also includes the appropriate labeled triphosphate analogs, which are commonly used in other sequencing methods known in the art. These are incorporated to the extension product by the RNA polymerase and serve to stop further extension along the target sequence. The resulting truncated extension products are labeled. The accumulated multiple displaced extension products vary in length, according to the site of incorporation of each of the analogs, which represent the various sequence locations of a complementary nucleotide on the target sequence. Analysis of the reaction products for elucidation of sequence information can be carried out as stated in the above sequencing example.

Example 8
Genotyping using Isothermal Enhanced Linear Amplification and Genotype Specific Composite Primer Genomic DNA is isolated from test cells using methods described in previous examples or by other mean known to the skilled artisan. Different organisms including, but not limited to, bacteria, viruses, fungi, yeast, plants, and animals are genotyped. Genotype specific primers are designed either to comprise a 3'-end nucleotide which hybridizes to one genotype of a specific nucleic acid sequence, or hybridize to the counterpart genotype. The sequence variation determining specific genotypes may be point mutation, single nucleotide polymorphism .(SNP), insertions deletions and the like.

Amplification of the defined target nucleic acid sequence is carried out as described for amplification of genomic *E. coli* sequence, in the above example. Using the genotype specific primer and DNA polymerase which is devoid of proof reading activity, the generation of amplification product indicates the presence of target sequence of the defined genotype. Sequence variation that prevents hybridization of the 3'-end of the primer to the target nucleic acid sequence will prevent amplification. The amplification product is detected by any one of various methods for detection of single stranded nucleic acid sequence, which is known in the art. For example, the hybridization of specific labeled oligonucleotide probes to the amplification product is detected by gel electrophoresis.

In cases where the genotyping of diploid cells is required, such as the determination of homozygote or heterozygote genotype, it is feasible to carry out the amplification of the specific nucleic acid target sequence using specific primers which are designed for either the wild type and mutant genotype, or one genotype and the other genotype. The amplification reactions using the specific primers are carried out in separate reaction vessels. The detection of amplification product in only one reaction tube or less amplification product is indicative of a homozygote genotype, i.e. either wild type or mutant homozygote. The detection of amplification product in both amplification reactions indicates a heterozygote genotype.

Example 9
RNA Portion-Based Isothermal Mutation Detection Utilizing Amplification Methods The isothermal amplification methods disclosed herein are used for the detection of defined mutations, or polymorphic sites (such as SNPs), in a target nucleic acid sequence. The methods are used for genotyping or detection of mutation leading to drug resistance. The target nucleic acid sequence is single-stranded (ss) DNA. Single-stranded DNA target is prepared from a double-stranded DNA target or an RNA target using isothermal amplification methods described herein.

As shown in FIG. 4, a composite primer which is complementary to a wild type DNA sequence is used in combination with a ss DNA target that has or is suspected to have a mutation within the allele under scrutiny. About $10^2$ to about $10^{12}$ copies of the ssDNA target and about 0.05–5 $\mu$M of composite primer is used. The presence of sequence alteration does not prevent the initial step of the amplification whereby the composite primer hybridizes to the target sequence to form the first tri-molecular complex, and an extension product is made. A ribonuclease, RNase H, then cleaves the RNA portion of the extended primer of the complex. The cleavage of the RNA portion of the composite primer, or the primer extension product, by RNase H is affected by the presence of a mismatch. This may prevent cleavage, alter cleavage patern, or reduce the efficiency of the cleavage. The next step of binding of a composite primer to the complex by hybridization of the 5' RNA portion is inhibited by a mismatch for the reason described above. The inability of the composite primer to hybridize to the target prevents further steps of primer extension strand displacement and production of multiple copies of the amplification products. The amplification products, or lack thereof, is visualized by gel electrophoresis or other equivalent means.

Factors which contribute to the inhibition of primer hybridization include the size of the hybridizing oligonucleotide and the stringency of the reaction condition. These factors are considered in the design of the composite primer, according to techniques well known and routine in the art.

A composite primer that is complementary to a mutated DNA sequence is also used in combination with a wild type ssDNA target in isothermal amplification method described above. In this case, the primer binds to the target DNA and undergoes extension. However, after treatment with RNase H, more primer cannot bind to the wild type DNA because of nucleotide mismatch and thus, little to no amplification product is made. The amplification products, or lack thereof, is visualized by gel electrophoresis or other equivalent means.

Parallel reactions are also run that include either the nucleic acid sample of interest or reference sample of target nucleic with a wild type sequence. Accumulation of more primer extension products in the former compared to the latter reaction is indicative of the presence of a mutant genotype in the sample of interest. Alternatively, when the composite primer comprises a 5' RNA sequence that is fully complementary to a normal genotype sequence of the test target, amplification of a target sequence of the mutant genotype is prevented, and the detection and/or quantitative determination of amplification products is indicative of a normal genotype.

Example 10
Genotyping Using Isothermal Amplification Methods and Genotype Specific Probe Hybridization Methods for sequencing by hybridization are described in previous examples. Determination of sequence identity by hybridization of specific probe is particularly advantageous using the isothermal method of the invention insofar as the amplification product generated by the method of the invention is single stranded and readily available to be used in hybridization of specific probes. Probes specific for a defined genotype are designed using methods known in the art. It is possible to determine hybridization criteria which will support selective probe hybridization to amplification products generated by amplification of one genotype and not the other. Sequence variation as small as a single nucleotide can prevent probe hybridization. The following factors are taken into consideration for hybridization criteria: probe length, temperature of the hybridization reaction, and buffer composition, in particular divalent ion concentration. The probes used for the ananlysis may be in solution, or may be attached to a solid surface. Further, the probes may be directly labeled or attached to a member of a specific binding pair and thus, able to specifically bind to another member of the specific binding pair which may be directly or indirectly labeled.

Genomic DNA is isolated from test samples by methods known in the art or as described in the above example. Test DNA is combined with the described amplification components, target-specific chimera primer, and propromoter sequence (such as PTO). The combination is subjected to incubation conditions as described herein to generate single stranded RNA amplification product. Hybridization of the amplification product to genotype specific probes is carried out in solution or solid phase with attached genotype specific probes. Since the products of enhanced isothermal linear amplification methods are single stranded, the products are ideally suited to be attached to a solid phase, such as glass slide, to generate an array of spatially resolved specific probes (i.e., gene chip). Alternatively, the solid phase comprises particles to which specific probes are attached. The detection of probe hybridization to the amplification products is carried out by various methods known in the art, for example, disclosed in Sambrook et al. supra. The specific probes is labeled, and the change in label spectral properties due to hybridization is detected and recorded by computer algorithms.

Particle association due to hybridization of specific probes to amplification products is also used for the detection of probe hybridization. Labeled amplification products are generated and product hybridization to probes immobilized on solid surfaces is detected and recorded by computer algorithms. The generation of labeled amplification product is carried out by incorporation of labeled rNTPs during the transcription step by substituting of one of the four rNTPs by a rNTP analog, which is labeled. The label is a dye, or a small molecule such as biotin, which is then detected by binding to specific binding entity, such as labeled streptavidin. Methods for detecting probe hybridization on solid surfaces are known in the art.

Example 11

Genotyping by rSSCP (RNA Single Stranded Conformation Polymorphism)

Genotyping is carried out by amplification of the specific target nucleic acid sequence using the methods described herein and by determination of the electrophoretic band pattern of the single stranded RNA product, which reflects the single stranded conformation. The use of SSCP for detection of sequence alteration is widely used. Genotype specific single stranded conformation is determined by subjecting samples to gel or capillary electrophoresis. The generation of single stranded product by amplification of target nucleic acid sequence according to the method of the invention, renders this method particularly suitable for genotype determination by combining the amplification method with rSSCP analysis.

Purified test genomic DNA is combined with components of the amplification method of the invention, as described above, and target specific composite primer and propromoter sequence, such as PTO. The combination is subjected to conditions for isothermal amplification of the target sequence. The reaction mixture containing the amplification product is subjected to either gel electrophoresis or capillary electrophoresis, using instrument and conditions known in the art. The electrophoretic band pattern of the amplification product is determined. The visualization of the oligonucleotide product is achieved by inclusion of a dye intercalator. The electrophoretic pattern of the amplification product is compared to that of amplification products generated by amplification of target nucleic acid sequence obtained from cells of known genotype. Any change in the electrophoretic mobility pattern is indicative of sequence variability. The combination of the amplification method of the invention and rSSCP provides a simple method for both the discovery of sequence polymorphism of defined target sequences, and detection of previously defined genotypes. The electrophoretic pattern of known nucleic acid sequences, or defined genotypes, can be predetermined, and the pattern generated by products of amplification of test DNA will be compared to known pattern for genotype determination.

What is claimed is:

1. A method for amplifying a polynucleotide sequence complementary to a target polynucleotide sequence comprising:
   (a) hybridizing a single stranded DNA template comprising the target sequence with a composite primer, said composite primer comprising an RNA portion and a 3' DNA portion;
   (b) optionally hybridizing a polynucleotide comprising a termination polynucleotide sequence to a region of the template which is 5' with respect to hybridization of the composite primer to the template;
   (c) extending the composite primer with DNA polymerase;
   (d) cleaving the RNA portion of the annealed composite with an enzyme that cleaves RNA from an RNA/DNA hybrid such that another composite primer hybridizes to the template and repeats primer extension by strand displacement,
   whereby multiple copies of the complementary sequence of the target sequence are produced.

2. A method for amplifying a target polynucleotide sequence comprising:
   (a) hybridizing a single stranded DNA template comprising the target sequence with a composite primer, said composite primer comprising an RNA portion and a 3' DNA portion;
   (b) optionally hybridizing a polynucleotide comprising a termination polynucleotide sequence to a region of the template which is 5' with respect to hybridization of the composite primer to the template;
   (c) extending the composite primer with DNA polymerase;
   (d) cleaving the RNA portion of the annealed composite primer with an enzyme that cleaves RNA from an RNA/DNA hybrid such that another composite primer hybridizes to the template and repeats primer extension by strand displacement to produce displaced primer extension product;
   (e) hybridizing a polynucleotide comprising a propromoter and a region which hybridizes to the displaced primer extension product under conditions which allow transcription to occur by RNA polymerase, such that RNA transcripts are produced comprising sequences complementary to the displaced primer extension products,
   whereby multiple copies of the target sequence are produced.

3. The method of claim 1 or 2, wherein the RNA portion of the composite primer is 5' with respect to the 3' DNA portion.

4. The method of claim 3, wherein the 5' RNA portion is adjacent to the 3' DNA portion.

5. The method of claim 1 or 2, wherein a plurality of composite primers are used.

6. The method of claim 1 or 2, wherein the polynucleotide comprising a termination polynucleotide sequence is a template switch oligonucleotide (TSO).

7. The method of claim 6, wherein the TSO comprises a modification in the region which hybridizes to the template, wherein, under a given set of conditions, the TSO binds more tightly to the region as compared to a TSO without the modification.

8. The method of claim 1 or 2, wherein the polynucleotide comprising a termination polynucleotide sequence is a blocking sequence.

9. The method of claim 8, wherein the blocking sequence comprises a modification in the region which hybridizes to the template, wherein, under a given set of conditions, the blocking sequence binds more tightly to the region as compared to a blocking sequence without the modification.

10. The method of claim 1 or 2, wherein the enzyme that cleaves RNA is RNaseH.

11. The method of claim 2, wherein the polynucleotide comprising a propromoter and region which hybridizes to the displaced primer extension product is a template switch oligonucleotide (TSO).

12. The method of claim 2, wherein the polynucleotide comprising the propromoter comprises a region at the 3' end which hybridizes to the displaced primer extension product, whereby DNA polymerase extension of displaced primer extension product produces a double stranded promoter from which transcription occurs.

13. The method of claim 12, wherein the polynucleotide comprising the propromoter is a propromoter template oligonucleotide (PTO).

14. The method of claim 1 or 2, wherein steps (a) and (b) are performed in either order.

15. The method of claim 1 or 2, wherein steps (a) and (b) are performed simultaneously.

16. The method of claim 1 or 2, wherein steps (a), (b) and (c) are performed simultaneously.

17. The method of claim 1 or 2, wherein steps (a) and (b) are performed before step (c).

18. The method of claim 1 or 2, wherein all steps are performed simultaneously.

19. A method of sequencing a target nucleotide sequence comprising:
  (a) hybridizing a single stranded DNA template comprising the target sequence with a composite primer, said composite primer comprising an RNA portion and a 3' DNA portion;
  (b) optionally hybridizing a polynucleotide comprising a termination polynucleotide sequence to a region of the template which is 5' with respect to hybridization of the composite primer to the template;
  (c) extending the composite primer with DNA polymerase and a mixture of dNTPs and dNTP analogs, such that primer extension is terminated upon incorporation of a dNTP analog;
  (d) cleaving the RNA portion of the annealed composite primer with an enzyme that cleaves RNA from an RNA/DNA hybrid such that another composite primer hybridizes to the template and repeats primer extension by strand displacement, whereby multiple copies of the complementary sequence of the target sequence are produced of varying lengths;
  (e) analyzing the product of steps (a) through (d) to determine sequence.

20. A method of sequencing a target nucleotide sequence comprising
  (a) hybridizing a single stranded DNA template comprising the target sequence with a composite primer, said composite primer comprising an RNA portion and a 3' DNA portion;
  (b) optionally hybridizing a polynucleotide comprising a termination polynucleotide sequence to a region of the template which is 5' with respect to hybridization of the composite primer to the template;
  (c) extending the composite primer with DNA polymerase;
  (d) cleaving the RNA portion of the annealed composite primer with an enzyme that cleaves RNA from an RNA/DNA hybrid such that another composite primer hybridizes to the template and repeats primer extension by strand displacement to produce displaced primer extension product;
  (e) hybridizing a polynucleotide comprising a propromoter and a region which hybridizes to the displaced primer extension product under conditions such that transcription occurs from the extension product by RNA polymerase, using a mixture of rNTPs and rNTP analogs, such that RNA transcripts are produced comprising sequences complementary to the displaced primer extension products, and such that transcription is terminated upon incorporation of an rNTP analog, whereby multiple copies of the target sequence are produced of varying lengths;
  (f) analyzing the product of steps (a) through (e) to determine sequence.

21. The method of claim 19 or 20, wherein the RNA portion of the composite primer is 5' with respect to the 3' DNA portion.

22. The method of claim 21, wherein the 5' RNA portion is adjacent to the 3' DNA portion.

23. A method of characterizing a sequence of interest in a target polynucleotide, said method comprising
  (i) amplifying a template polynucleotide sequence containing the sequence of interest by the method of claim 1 or 2, wherein the sequence of the RNA portion of the composite primer is known, and
  (ii) comparing the amplification products if any from step (i) with the amount of amplification products from a reference template
  wherein
  (1) production of detectably fewer amplification products from the template as compared to the amount of amplification products from the reference template which comprises a region complementary to the RNA portion of the composite primer indicates that the target polynucleotide does not comprise a sequence complementary to the RNA portion of the composite primer and is a sequence variant with respect to the sequence complementary to the RNA portion of the composite primer; or
  (2) production of detectably more amplification products from the template as compared to the amount of amplification products from the reference template which does not comprise a region which is complementary to the RNA portion of the composite primer indicates that the target polynucleotide comprises a sequence complementary to the RNA portion of the composite primer and is not a sequence variant with respect to the sequence complementary to the RNA portion of the composite primer.

24. The method of claim 23, wherein the sequence of the RNA portion of the composite primer comprises a sequence complementary to a wild type sequence, and the sequence of interest is characterized in determining the presence or absence of the wild type sequence.

25. The method of claim 23, wherein the sequence of the RNA portion of the composite primer comprises a sequence complementary to a mutant sequence, and the sequence of interest is characterized in determining the presence or absence of the mutant sequence.

26. The method of claim 23, wherein the sequence of the RNA portion of the composite primer comprises a sequence complementary to an allelic sequence, and the sequence of interest is characterized in determining the presence or absence of the allelic sequence.

27. A method of detecting a mutation in a target polynucleotide by single stranded conformation polymorphism, comprising (i) amplifying the target polynucleotide by the method of claim 1 or 2; and (ii) analyzing the amplification products for single stranded conformation, wherein a difference in conformation as compared to a reference single stranded polynucleotide indicates a mutation in the target polynucleotide.

28. The method of claim 23, wherein the RNA portion of the composite primer is 5' with respect to the 3' DNA portion.

29. The method of claim 28, wherein the 5' RNA portion is adjacent to the 3' DNA portion.

30. A method of producing a microarray, comprising (i) amplifying a polynucleotide sequence by the method of claim 1 or 2; and (ii) attaching the amplified products onto a solid substrate to make a microarray of the amplified products.

31. A composition comprising (a) a composite primer, said composite primer comprising a 3' DNA portion and a 5' RNA portion, and (b) a polynucleotide comprising a termination polynucleotide sequence, wherein the termination polynucleotide sequence effects cessation of DNA replication of a template by DNA polymerase.

32. The composition of claim 31, wherein the 5' RNA portion is adjacent to the 3' DNA portion.

33. The composition of claim 31, wherein the 5' RNA portion is about 5 to about 20 nucleotides and the 3' DNA portion is about 5 to about 15 nucleotides.

34. The composition of claim 31, wherein the polynucleotide comprising a termination polynucleotide sequence is a TSO.

35. The composition of claim 34, wherein the TSO comprises a modification in the region which hybridizes to the template, wherein, under a given set of conditions, the TSO binds more tightly to the region as compared to a TSO without the modification.

36. The composition of claim 31 wherein the termination polynucleotide sequence is a blocking sequence.

37. The composition of claim 31, further comprising a propromoter template oligonucleotide (PTO).

38. A composition comprising a complex of (a) a template strand; (b) a composite primer, said composite primer comprising a 3' DNA portion and an RNA portion; and (c) a polynucleotide comprising a termination polynucleotide sequence, wherein the termination polynucleotide sequence effects cessation of DNA replication of a template by DNA polymerase.

39. The composition of claim 38, wherein the RNA portion is 5' and adjacent to the 3' DNA portion.

40. The composition of claim 38, wherein the polynucleotide comprising a termination polynucleotide sequence is a TSO.

41. The composition of claim 38 wherein the polynucleotide comprising a termination polynucleotide sequence is a blocking sequence.

42. A reaction mixture comprising (a) a polynucleotide template; (b) a composite primer comprising a 3' DNA portion and an RNA portion; (c) a DNA polymerase; and (d) a polynucleotide comprising a termination polynucleotide sequence, wherein the termination polynucleotide sequence effects cessation of DNA replication of a template by DNA polymerase.

43. The reaction mixture of claim 42, wherein the composite primer comprises a 5' RNA portion which is adjacent to the 3' DNA portion.

44. The reaction mixture of claim 43, further comprising an enzyme which cleaves RNA from an RNA/DNA hybrid.

45. The reaction mixture of claim 44, wherein the enzyme is RNaseH.

46. The reaction mixture of claim 42, further comprising a polynucleotide comprising a propromoter.

47. The reaction mixture of claim 46, wherein the polynucleotide comprising a propromoter is a TSO.

48. The reaction mixture of claim 46, wherein the polynucleotide comprising a propromoter is a propromoter template oligonucleotide (PTO).

49. A kit for amplification of a target polynucleotide sequence, comprising (a) a composite primer comprising a 3' DNA portion and an RNA portion, and (b) a polynucleotide comprising a termination polynucleotide sequence, wherein the termination polynucleotide sequence effects cessation of DNA replication of a template by DNA polymerase.

50. The kit of claim 49, wherein the RNA portion is 5' with respect to the 3' DNA portion.

51. The kit of claim 50, wherein the 5' RNA portion is adjacent to the 3' DNA portion.

52. The kit of claim 49, wherein the polynucleotide comprising a termination polynucleotide sequence is a TSO.

53. The kit of claim 49, wherein the polynucleotide comprising a termination polynucleotide sequence is a blocker sequence.

54. The kit of claim 49, further comprising a polynucleotide comprising a propromoter.

55. The kit of claim 54, wherein the polynucleotide comprising a propromoter is a TSO.

56. The kit of claim 54, wherein the polynucleotide comprising a propromoter is a PTO.

57. The kit of claim 49, further comprising an enzyme which cleaves RNA from an RNA/DNA hybrid.

58. The kit of claim 57, wherein the enzyme is RNaseH.

59. The method of claim 19 or 20, wherein the polynucleotide comprising a termination polynucleotide sequence is a template switch oligonucleotide (TSO).

60. The method of claim 59, wherein the TSO comprises a modification in the region which hybridizes to the template, wherein, under a given set of conditions, the TSO binds more tightly to the region as compared to a TSO without the modification.

61. The method of claim 19 or 20, wherein the polynucleotide comprising a termination polynucleotide sequence is a blocking sequence.

62. The method of claim 61, wherein the blocking sequence comprises a modification in the region which hybridizes to the template, wherein, under a given set of conditions, the blocking sequence binds more tightly to the region as compared to a blocking sequence without the modification.

63. The method of claim 19 or 20, wherein the enzyme that cleaves RNA is RNaseH.

64. The method of claim 20, wherein the polynucleotide comprising a propromoter and region which hybridizes to the displaced primer extension product is a template switch oligonucleotide (TSO).

65. The method of claim 20, wherein the polynucleotide comprising the propromoter comprises a region at the 3' end which hybridizes to the displaced primer extension product, whereby DNA polymerase extension of displaced primer extension product produces a double stranded promoter from which transcription occurs.

66. The method of claim 65, wherein the polynucleotide comprising the propromoter is a propromoter template oligonucleotide (PTO).

67. The method of claim 19 or 20, wherein steps (a) and (b) are performed in either order.

68. The method of claim 19 or 20, wherein steps (a) and (b) are performed simultaneously.

69. The method of claim 19 or 20, wherein steps (a), (b) and (c) are performed simultaneously.

70. The method of claim 19 or 20, wherein steps (a) and (b) are performed before step (c).

71. The method of claim 19 or 20, wherein all steps except the step of analyzing the product are performed simultaneously.

72. The method of claim 23, wherein the RNA portion of the composite primer is 5' with respect to the 3' DNA portion.

73. The method of claim 72, wherein the 5' RNA portion is adjacent to the 3' DNA portion.

74. The method of claim 23, wherein the polynucleotide comprising a termination polynucleotide sequence is a template switch oliognucleotide (TSO).

75. The method of claim 74, wherein the TSO comprises a modification in the region which hybridizes to the template, wherein, under a given set of conditions, the TSO binds more tightly to the region as compared to a TSO without the modification.

76. The method of claim 23, wherein the polynucleotide comprising a termination polynucleotide sequence is a blocking sequence.

77. The method of claim 76, wherein the blocking sequence comprises a modification in the region which hybridizes to the template, wherein, under a given set of conditions, the blocking sequence binds more tightly to the region as compared to a blocking sequence without the modification.

78. The method of claim 23, wherein the enzyme that cleaves RNA is RNaseH.

79. A method of characterizing a sequence of interest in a target polynucleotide, said method comprising
 (i) amplifying a template polynucleotide sequence containing the sequence of interest by the method of claim 2, wherein the sequence of the RNA portion of the composite primer is known, and
 (ii) comparing the amplification products if any from step (i) with the amount of amplification products from a reference template
 wherein (1) production of detectably fewer amplification products from the template as compared to the amount of amplification products from the reference template which comprises a region complementary to the RNA portion of the composite primer indicates that the target polynucleotide does not comprise a sequence complementary to the RNA portion of the composite primer and is a sequence variant with respect to the sequence complementary to the RNA portion of the composite primer; or
 (2) production of detectably more amplification products from the template as compared to the amount of amplification products from the reference template which does not comprise a region which is complementary to the RNA portion of the composite primer indicates that the target polynucleotide comprises a sequence complementary to the RNA portion of the composite primer and is not a sequence variant with respect to the sequence complementary to the RNA portion of the composite primer.
 and wherein the polynucleotide comprising a propromoter and region which hybridizes to the displaced primer extension product is a template switch oligonucleotide (TSO).

80. The method of claim 23, wherein the polynucleotide comprising the propromoter comprises a region at the 3' end which hybridizes to the displaced primer extension product, whereby DNA polymerase extension of displaced primer extension product produces a double stranded promoter from which transcription occurs.

81. The method of claim 80, wherein the polynucleotide comprising the propromoter is a propromoter template oligonucleotide (PTO).

82. The method of claim 23, wherein steps (a) and (b) are performed in either order.

83. The method of claim 23, wherein steps (a) and (b) are performed simultaneously.

84. The method of claim 23, wherein steps (a), (b) and (c) are performed simultaneously.

85. The method of claim 23, wherein steps (a) and (b) are performed before step (c).

86. The method of claim 23, wherein all steps except the step of comparing the amplification products are performed simultaneously.

87. The method of claim 27, wherein the polynucleotide comprising a termination polynucleotide sequence is a template switch oliognucleotide (TSO).

88. The method of claim 87, wherein the TSO comprises a modification in the region which hybridizes to the template, wherein, under a given set of conditions, the TSO binds more tightly to the region as compared to a TSO without the modification.

89. The method of claim 27, wherein the polynucleotide comprising a termination polynucleotide sequence is a blocking sequence.

90. The method of claim 89, wherein the blocking sequence comprises a modification in the region which hybridizes to the template, wherein, under a given set of conditions, the blocking sequence binds more tightly to the region as compared to a blocking sequence without the modification.

91. The method of claim 27, wherein the enzyme that cleaves RNA is RNaseH.

92. A method of detecting a mutation in a target polynucleotide by single stranded conformation polymorphism comprising (i) amplifying the target polynucleotide by the method of claim 2 and (ii) analyzing the amplification products for single stranded conformation, wherein a difference in conformation as compared to a reference single stranded polynucleotide indicates a mutation in the target polynucleotide
 and wherein the polynucleotide comprising a propromoter and region which hybridizes to the displaced primer extension product is a template switch oligonucleotide (TSO).

93. The method of claim 27, wherein the polynucleotide comprising the propromoter comprises a region at the 3' end which hybridizes to the displaced primer extension product, whereby DNA polymerase extension of displaced primer extension product produces a double stranded promoter from which transcription occurs.

94. The method of claim 93, wherein the polynucleotide comprising the propromoter is a propromoter template oligonucleotide (PTO).

95. The method of claim 27, wherein steps (a) and (b) are performed in either order.

96. The method of claim 27, wherein steps(a) and (b) are performed simultaneously.

97. The method of claim 27, wherein steps (a), (b) and (c) are performed simultaneously.

98. The method of claim 27, wherein steps (a) and (b) are performed before step (c).

99. The method of claim 27, wherein all steps except the step of analyzing the amplification products are performed simultaneously.

100. The method of claim 27, wherein the mutation is selected from the group consisting of a base substitution, a base insertion, a base deletion and a single nucleotide polymorphism.

101. The method of claim 27, wherein said step of analyzing the amplification products comprises a method selected from the group consisting of gel electrophoresis, capillary electrophoresis and cleavage of the amplification products using nucleases which recognize sequence dependent secondary structures.

102. The method of claim 30, wherein the polynucleotide comprising a termination polynucleotide sequence is a template switch oliognucleotide (TSO).

103. The method of claim 102, wherein the TSO comprises a modification in the region which hybridizes to the template, wherein, under a given set of conditions, the TSO binds more tightly to the region as compared to a TSO without the modification.

104. The method of claim 30, wherein the polynucleotide comprising a termination polynucleotide sequence is a blocking sequence.

105. The method of claim 104, wherein the blocking sequence comprise a modification in the region which hybridizes to the template, wherein, under a given set of conditions, the blocking sequence binds more tightly to the region as compared to a blocking sequence without the modification.

106. The method of claim 30, wherein the enzyme that cleaves RNA is RNaseH.

107. The method of claim 30, wherein the polynucleotide comprising a propromoter and region which hybridizes to the displaced primer extension product is a template switch oligonucleotide (TSO).

108. A method of producing a microarrray, comprising (i) amplifying a polynucleotide sequence by the method of claim 2; and (ii) attaching the amplified products onto a solid substrate to make a microarray of the amplified products and wherein the polynucleotide comprising the propromoter comprises a region at the 3' end which hybridizes to the displaced primer on product, whereby DNA polymerase extension of displaced primer extension product produces a double stranded promoter from which transcription occurs.

109. The method of claim 108, wherein the polynucleotide comprising the propromoter is a propromoter template oligonucleotide (PTO).

110. The method of claim 30, wherein steps (a) and (b) are performed in either order.

111. The method of claim 30, wherein steps (a) and (b) are performed simultaneously.

112. The method of claim 30, wherein steps (a), (b) and (c) are performed simultaneously.

113. The method of claim 30, wherein steps (a) and (b) are performed before step (c).

114. The method of claim 30, wherein all steps except the step of attaching the amplified products are performed simultaneously.

115. The reaction mixture of claim 42, wherein the polynucleotide comprising a termination polynucleotide sequence is a template switch oligonucleotide.

116. The reaction mixture of claim 42, wherein the polynucleotide comprising a termination polynucleotide sequence is a blocking sequence.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Synthetic primer
<220> FEATURE:
<223> OTHER INFORMATION: Chimeric DNA/RNA primer.
      IA005

<400> SEQUENCE: 1
acggaugcgg ucuccagtgt                                                    20

<210> SEQ ID NO 2
<211> LENGTH: 20
<212> TYPE: DNA
<213> ORGANISM: Synthetic primer
<220> FEATURE:
<223> OTHER INFORMATION: Chimeric DNA/RNA primer.
      IA019

<400> SEQUENCE: 2
acggaugcgg ucuccagtgt                                                    20

<210> SEQ ID NO 3
<211> LENGTH: 21
<212> TYPE: DNA
<213> ORGANISM: Synthetic primer
<220> FEATURE:
<223> OTHER INFORMATION: Chimeric DNA/RNA primer.
      IA020

<400> SEQUENCE: 3
gacggaugcg gucuccagtg t                                                  21

<210> SEQ ID NO 4
<211> LENGTH: 25
<212> TYPE: DNA
<213> ORGANISM: Synthetic primer
<220> FEATURE:
<223> OTHER INFORMATION: Chimeric DNA/RNA primer

<400> SEQUENCE: 4
gcaagacgga ugcggucucc agtgt                                              25

<210> SEQ ID NO 5
<211> LENGTH: 21
<212> TYPE: DNA
<213> ORGANISM: Synthetic primer
<220> FEATURE:
<223> OTHER INFORMATION: Chimeric DNA/RNA primer

<400> SEQUENCE: 5
gacggatgcg guctccagtg t                                                  21

<210> SEQ ID NO 6
<211> LENGTH: 21
<212> TYPE: DNA
<213> ORGANISM: Synthetic primer
<220> FEATURE:
<223> OTHER INFORMATION: Chimeric DNA/RNA primer

<400> SEQUENCE: 6
gacggatgcg guctccagug t                                                  21

-continued

```
<210> SEQ ID NO 7
<211> LENGTH: 24
<212> TYPE: DNA
<213> ORGANISM: Synthetic primer
<220> FEATURE:
<223> OTHER INFORMATION: Chimeric DNA/RNA primer

<400> SEQUENCE: 7
gacggatgcg guctccagug ucca                                          24

<210> SEQ ID NO 8
<211> LENGTH: 67
<212> TYPE: DNA
<213> ORGANISM: Synthetic primer
<220> FEATURE:
<223> OTHER INFORMATION: IA012

<400> SEQUENCE: 8
ggaattctaa tacgactcac tatagggaga gatcgagtag ctccggtacg ctgatcaaag   60
atccgtg                                                            67

<210> SEQ ID NO 9
<211> LENGTH: 60
<212> TYPE: DNA
<213> ORGANISM: Synthetic primer
<220> FEATURE:
<223> OTHER INFORMATION: IA012b

<400> SEQUENCE: 9
taatacgact cactataggg agagatcgag tagctccggt acgctgatca aagatccgtg   60

<210> SEQ ID NO 10
<211> LENGTH: 48
<212> TYPE: DNA
<213> ORGANISM: Synthetic primer
<220> FEATURE:
<223> OTHER INFORMATION: IA015

<400> SEQUENCE: 10
taatacgact cactataggg agagcggtac gctgatcaaa gatccgtg                48

<210> SEQ ID NO 11
<211> LENGTH: 55
<212> TYPE: DNA
<213> ORGANISM: Synthetic primer
<220> FEATURE:
<223> OTHER INFORMATION: IA015b

<400> SEQUENCE: 11
ggaattctaa tacgactcac tatagggaga gcggtacgct gatcaaagat ccgtg        55

<210> SEQ ID NO 12
<211> LENGTH: 55
<212> TYPE: DNA
<213> ORGANISM: Synthetic primer
<220> FEATURE:
<223> OTHER INFORMATION: Guanine has biotin molecule attached.
      IA015c

<400> SEQUENCE: 12
ggaattctaa tacgactcac tatagggaga gcggtacgct gatcaaagat ccgtg        55

<210> SEQ ID NO 13
<211> LENGTH: 21
<212> TYPE: DNA
```

```
<213> ORGANISM: Synthetic primer
<220> FEATURE:
<223> OTHER INFORMATION: IA010

<400> SEQUENCE: 13
atgtcatggt catggtcgtg t                                                  21

<210> SEQ ID NO 14
<211> LENGTH: 31
<212> TYPE: DNA
<213> ORGANISM: Synthetic primer
<220> FEATURE:
<223> OTHER INFORMATION: IA014

<400> SEQUENCE: 14
ctcaacacga ccatgaccat gacatttgtt g                                       31

<210> SEQ ID NO 15
<211> LENGTH: 25
<212> TYPE: DNA
<213> ORGANISM: Synthetic primer
<220> FEATURE:
<223> OTHER INFORMATION: IA004

<400> SEQUENCE: 15
cgcatacgga atagcttacc ggtct                                              25

<210> SEQ ID NO 16
<211> LENGTH: 23
<212> TYPE: DNA
<213> ORGANISM: Synthetic primer
<220> FEATURE:
<223> OTHER INFORMATION: IA006

<400> SEQUENCE: 16
cggtacgctg atcaaagatc cgt                                                23

<210> SEQ ID NO 17
<211> LENGTH: 351
<212> TYPE: DNA
<213> ORGANISM: Synthetic primer

<400> SEQUENCE: 17
cggtacgctg atcaaagatc cgtgcaacaa atgtcatggt catggtcgtg ttgagcgcag        60
caaaacgctg tccgttaaaa tcccggcagg ggtggacact ggagaccgca tccgtcttgc       120
gggcgaaggt gaagcgggcg agcatggcgc accggcaggc gatctgtacg ttcaggttca       180
ggttaaacag cacccgattt tcgagcgtga aggcaacaac ctgtattgcg aagtcccgat       240
caacttcgct atgcggcgc tgggtggcga aatcgaagta ccgacccttg atggtcgcgt        300
caaactgaaa gtgcctggcg aaacccagac cggtaagcta ttccgtatgc g                351

<210> SEQ ID NO 18
<211> LENGTH: 115
<212> TYPE: DNA
<213> ORGANISM: Synthetic primer
<220> FEATURE:
<223> OTHER INFORMATION: IA013

<400> SEQUENCE: 18
cggtacgctg atcaaagatc cgtgcaacaa atgtcatggt catggtcgtg ttgagcgcag        60
caaaacgctg tccgttaaaa tcccggcagg ggtggacact ggagaccgca tccgt           115
```

-continued

```
<210> SEQ ID NO 19
<211> LENGTH: 100
<212> TYPE: DNA
<213> ORGANISM: Synthetic primer
<220> FEATURE:
<221> NAME/KEY: allele
<222> LOCATION: (0)...(0)
<223> OTHER INFORMATION: IA009

<400> SEQUENCE: 19
agtgtccacc cctgccggga ttttaacgga cagcgttttg ctgcgctcaa cacgaccatg      60
accatgacat ttgttgcacg gatctttgat cagcgtaccg                          100

<210> SEQ ID NO 20
<211> LENGTH: 24
<212> TYPE: DNA
<213> ORGANISM: Bacteriophage

<400> SEQUENCE: 20
taatacgact cactataggg agag                                            24

<210> SEQ ID NO 21
<211> LENGTH: 7
<212> TYPE: DNA
<213> ORGANISM: Synthetic primer

<400> SEQUENCE: 21 ggaattc                                                               7

<210> SEQ ID NO 22
<211> LENGTH: 12
<212> TYPE: DNA
<213> ORGANISM: Synthetic primer

<400> SEQUENCE: 22
atcgagtagc tc                                                        12
```